(12) United States Patent
Greene et al.

(10) Patent No.: US 6,372,884 B1
(45) Date of Patent: *Apr. 16, 2002

(54) BIOLOGICALLY ACTIVE COMPOUNDS AND METHODS OF CONSTRUCTING AND USING THE SAME

(75) Inventors: Mark I. Greene, Penn Valley; William V. Williams, Havertown; David B. Weiner, Merion, all of PA (US); Jeffrey A. Cohen, Solon, OH (US); Thomas Kieber-Emmons, Newtown Square, PA (US); Robert M. Williams, Fort Collins, CO (US)

(73) Assignee: The Trustees of the University of Pennsylvania, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/752,816

(22) Filed: Nov. 21, 1996

Related U.S. Application Data

(63) Continuation of application No. 07/940,654, filed on Sep. 3, 1992, now Pat. No. 5,637,677, which is a continuation-in-part of application No. 07/702,833, filed on May 20, 1991, now abandoned, which is a continuation of application No. 07/326,328, filed on Mar. 21, 1989, now abandoned, which is a continuation-in-part of application No. 07/074,264, filed on Jul. 16, 1987, now abandoned, which is a continuation-in-part of application No. 07/462,542, filed on Jan. 9, 1990, now abandoned, which is a division of application No. 07/074,264, filed on Jul. 16, 1987, now abandoned, which is a continuation-in-part of application No. 07/648,303, filed on Jan. 25, 1991, now abandoned, which is a continuation of application No. 07/074,264, filed on Jul. 16, 1987, now abandoned, which is a continuation-in-part of application No. 07/685,881, filed on Apr. 15, 1991, now abandoned, which is a continuation of application No. 07/574,391, filed on Aug. 27, 1990, now abandoned, which is a continuation of application No. 07/194,026, filed on May 13, 1988, now Pat. No. 4,962,510, which is a continuation-in-part of application No. 07/074,264, filed on Jul. 16, 1987, now abandoned, which is a continuation-in-part of application No. 07/583,626, filed on Sep. 14, 1990, now abandoned.

(51) Int. Cl.[7] .................. C07K 7/00; C07K 14/14

(52) U.S. Cl. ............ 530/333; 530/300; 530/350; 530/387.2; 530/388.27; 530/388.3; 530/388.35; 424/185.1; 424/184.1; 424/193.1; 424/215.1; 435/7.1; 514/2; 514/12; 514/13; 514/14

(58) Field of Search ................... 530/300, 333, 530/350, 387.2, 388.27, 388.3, 388.35; 424/185.1, 184.1, 193.1, 215.1; 435/7.1; 514/2, 12, 13, 14

(56) References Cited

U.S. PATENT DOCUMENTS

| | | | |
|---|---|---|---|
| 1,092,960 A | | 4/1914 | Taylor et al. |
| 4,490,358 A | | 12/1984 | Greene et al. |
| 4,683,295 A | | 7/1987 | Carson |
| 4,761,371 A | | 8/1988 | Bell et al. |
| 5,637,677 A | * | 6/1997 | Greene et al. ............ 530/333 |

FOREIGN PATENT DOCUMENTS

| | | |
|---|---|---|
| EP | 0 328 403 | 8/1989 |
| WO | WO 89/03222 | 4/1989 |
| WO | WO 89/10939 | 11/1989 |
| WO | WO 91/04273 | 4/1991 |
| WO | WO 91/17177 | 11/1991 |

OTHER PUBLICATIONS

Williams, et al., "Development of biologically active peptides based on antibody structure", *Proc. Natl. Acad. Sci. USA,* 86, 1989, 5537–5541.

Williams, et al., "Determination of the Neutralizing/Cell–Attachment Epitope of Reovirus Type $3^{1}$", Symposia on Molecular and Cellular Biology, New Series, vol. 84, *Technological Advances in Vaccine Development,* Genentech, Ortho, Smith Kline and French—UCLA Symposium, Utah, Jan. 30 through Feb. 6, 1988, pp. 577–586, Alan R. Liss, Inc.

Williams, et al., "Sequences of the cell–attachment sites of reovirus type 3 and its anti–idiotypic/antireceptor antibody: modeling of their three–dimensional structures":, *Proc. Natl. Acad. Sci., USA,* 85, 1988, 6488–6492.

Mazza, et al., "A structural basis for the internal image in the idiotypic network: antibodies against synthetic Ab2–D regions cross–react with the original antigen", *Ann. Inst. Pasteur Immunol.,* vol. 136, D, 1985, 259–269, Elsevier, Paris, FR.

Bruck, C. et al., "Nucleic acid sequence of an internal image–bearing monoclonal anti–idiotype and its comparison to the sequence of the external antigen", *Proc. Natl. Acad. Sci. USA* 1986, 83, 6578–6582.

Smith, et al., "Generation of Idiotypic ad Anti–idiotypic Antibodies by Immunization with Peptides Encoded by Complementary RNA: A Possible Molecular Basis for the Network Theory", *J. of Immunol.,* 138, 1987, 7–9.

(List continued on next page.)

Primary Examiner—Julie Burke
(74) Attorney, Agent, or Firm—Woodcock Washburn Kurtz Mackiewicz & Norris LLP

(57) ABSTRACT

A method of constructing biologically active compounds which mimic the biological activity of the biologically active protein block the activity of the biologically active protein is disclosed. A method of identifying specific and discrete portions of pathogen antigens which either serve as epitopes for neutralizing antibodies or which are involved in pathogen binding to host cell receptors is disclosed. A method of constructing biologically active compounds which compete with cellular receptors for binding to either biologically active proteins or pathogen antigens is disclosed.

2 Claims, 43 Drawing Sheets

OTHER PUBLICATIONS

Williams, et al. "Sequences of Cell Attachment Sites" PNAS 85: 6488–6492 (1985).

Gaulton, et al. "Inhibition of Cellular DNA Synthesis" J. of Exp. Med. 169:197–212 (1989).

Sun, et al. "Generation and Characterization of Monoclonal . . ." J. of Virology 63(9):3579–3585 (1989).

Cantor and Schimmel Biophysical Chemistry Part 1, pp. 35–126 (1989).

Burstein, et al., "Evidence For Functional Domains On The Reovirus Type 3 Hemagglutinin", Virology, 117:146–155 (1982).

Bruck, et al., "Nucleic Acid Sequence Of An Internal Image–Bearing Monoclonal Anti–Idiotype And Its Comparison To The Sequence Of The External Antigen", Proc. Natl. Acad. Scit. USA, 83:6578–6582, Sep. 1986.

Bassel–Duby, "Sequence Of Reovirus Hemagglutinin Predicts A Coiled–Coil Structure", Nature, 315:421–423 (1985).

Gaulton, et al., "Idiotypic Mimcry Of Biological Receptors", Ann. Rev. Immunol. 1986 4:253–280.

Gaulton, et al., "Anti–Idiotypic Antibody Identifies The Cellular Receptor Of Reovirus Type3", Journal of Cellular Biochemistry, 28:69–78 (1985).

Gaulton, et al., "Syngeneic Monoclonal Internal Image Anti–Idiotopes As Prophylactic Vaccines", The Journal of Immunology, 137, 2930–2936 (Nov. 1, 1986).

Monroe, et al., "Anti–Idiotypic Antibodies And Disease", Immunological Investigations, 15(3) 263–286 (1986).

Smith, et al., Cancer Research, vol. 45, pp. 6119–6123 (Dec. 1985).

Thanaval, et al., J. Exp. Med., vol. 164, pp. 227–236 (Jul. 1986).

Chanh, et al., Proc. Natl. Acad. Sci. USA, vol. 84, pp. 3891–3895 (Jun. 1987).

Fritz, et al., Journal of Immunology, vol. 128, pp. 247–250 (Jan. 1982).

Seiden, et al., Journal of Immunology, vol. 136, pp. 582–587 (Jan. 1986).

Budisavljevic, et al., Journal of Immunologuy, vol. 140, pp. 3059–3065 (May 1988).

Wo, A. 8702990 Schering–Biotech Co. May 21, 1987 (Dialog Database File 351, WPI Acc. No. 87–150613/21 XRAM Acc. No: C87–062883).

Wo, A. 8807374 Hiver, Oct. 6, 1988 (Dialog Database File: 357, WPI Acc. No. 88–292708).

Wo, A, 8809181 Tanox Biosystems In. Dec. 1, 1988. (Dialog Database File: 351, WPI Acc. No. 88–353807/49. XRAM Acc. No. C88–156503).

EP, A, 241139 Merck and Co Inc. Oct. 14, 1987. (Dialog Database File: 351, WPI Acc. No. 87–285998/41, XRAM Acc. No. C87–121247).

Molecular and Cellular Biochemistry, vol. 65, pp. 5–21 Nov. 1984, C. N. Gaulton, et al., "Anti–Iiotypic Antibodies As Probes of Cell Surface Receptors." (Dialog Database File 155, Acc. No. 85110880).

R. Arnon (editor), *Synthetic Vaccines,* vol. 1, 1987, CRC Press, Boca Raton, Florida (Dialog Database File 5, Biosis No. 35080391).

Lerner, R.A. et al. (editors), *Vaccines 85,* Cold Spring Harbor Laboratory, New York, 11724, published 1985, pp. 151–156.

London, et al., "Gut Mucosal Immunization With Reovirus Serotype I/L Stimulates Viral Specific Cytotoxic T Cell Precursors As Well As IgA Memory Cells In Peyer's Patches", (1987).

Rubin, et al., "Reovirus Serotype 1 Intestinal Infection: A Novel Replicative cycle With Ilead Disease", J. Virol., 53: 391–397 (1985).

Schneerson, et al., "Preparation, Characterization And Immunogenicity Of Hemophilus Influenzae Type b Polysaccaharide Protein Conjugates", J. Exp. Med. 152: 361 (1980).

Noseworthy, et al., "Cell Receptors For The Mammalian Reovirus. I. Syngeneic Monoclonal Anti–Idiotypic Antibody Identifies A Cell Surface Receptor For Reovirus", J. Immunol. 131: 2533–2538 (1983).

Goulton, et al., "Isolation And Biochemical Characterization Of The Mammalism Reovirus Type 3 Cell–Surface–Receptor", Proc. Nat'l Acad. Sci. USA, 82: 1494–1498 (1985).

Spriggs, et al., "Topological Analysis Of The Reovirus Type 3 Hemagglutinin", Virology 127: 220–224 (1983).

Manemitsu, et al., "Biosynthesis Of Reovirus–Specified Polypeptides. Molecular cDNA Cloning and Nucleotide Sequence Of The Reovirus Serotype 1 Long Strain Bicistronic S1m RNA Which Encodes The Minor Capsid Polypeptide /a And The Nonstructural Polypeptide 16 NS", Biochem. Biophys. Res. Commun., 140: 501–510 (1986).

Weiss, et al., "Delayed Type Hypersensitivity To Mice Infected With Reovirus. Identification Of Host And Viral Gene Products Responsible For the Immune Response", J. Immunol., 125: 278–282 (1980).

Bassel–Duby, et al., "Identification Of Attenuating Mutations On The Reovirus Type 3 S1 Double–Stranded RNA Segment With A Rapid Sequencing Technique", J. Virol., 60: 64–67 (1986).

Kaye, et al., "Genetic Basis For Altered Pathogenesis Of An Immune–Selected Antigenic Variant Of Reovirus Type 3 (Dearing)", J. Virol., 59: 90–97 (1986).

Spriggs, et al., "Annenuated Reovirus Type 3 Strains Generated By Selection of Hemagglutinin Antigenic Variants", Nature (London) 297: 68–70 (1982).

Chou, et al., "Conformational Parameters For Amino Acids In Helical, Beta Sheet, And Random Coil Regions Calculated From Proteins", Biochemistry, 13(2): 211 (1974).

Institute of Medicine, "Vaccine Supply And Innovation", Nat'l Acad. Press (1985).

Jerne, "Towards A Network Theory Of The Immune System", Ann. Immunol. (Paris) 125: 337–389 (1974).

Sharpe, et al., "Synogenic Monoclonal Antiidiotype Can Induce Cellular Immunity To Reovirus", J. Exp. Med., 160: 195 205 (1984).

Kauffman, et al., "Cell Receptors For Mammalian Reovirus II Monoclonal Anti–Idiotypic Antibody Blocks Viral Binding To Cells," J. Immunol. 131: 2539–2541 (1983).

Ertl, et al., "Sendai Virus Specific T Cell Clones: Induction Of Cytolytic T Cells By An Anti–Idiotypic Antibody Directed Against A Helper T Cell Clone," Proc. Nat'l Acad. Sci. USA 81: 2850–2854 (1984).

Reagen, et al., "Anti–Idiotypic Antibodies Induce Neutralizing Antibodies To Rabies Virus Glycoproteins", J. Virol., 48: 660–666 (1983).

Uydeltaag, et al., "Induction Of Neutralizing Antibody In Mice Against Polio Virus Type II With Monoclonal Antiidiotypic Antibody," J. Immunol., 134: 1225–1229 (1985).

Elder, et al., "Localization Of Neutralizing Regions Of The Envelope Gene Of Feline Leukemia Virus By Using Anti-Synthetic Peptide Antibodies",J. Virol.,61:8–15 (1987).

Lasky, L. et al., Science 233:209–212, Neutralization of the AIDS retrovirus by antibodies to a recombinant envelope glycoprotein, Jul. 11, 1997.

Geysen et al PNAS 81:3998, Jul. 1984.*

Schwartz et al PNAS 84:6408, Sep. 1987.*

Lin et al Biochemistry 14(8):1559, 1975.*

Lazar et al Mol Cell Biol 8(3):1247, Mar. 1988.*

Burgess et al J Cell Biol 111:2129, Nov. 1990.*

Lewin Science 237:1570, 1987.*

Reeck et al Cell 50:667, 1987.*

George et al Current Methods in Sequence Comparison and Analysis in Macromolecular Sequencing and Synthesis, Selected Methods and Applications. 127–149, 1988.*

Barton et al Protein Sequence Alignment and Database Scanning In Protein Structure Prediction, A Practical Approach. IRL Press pp. 31–63, 1996.*

Creighton Protein: Structure and Molecular Properties. WH Freeman and Co NY 108–109 and 132–133, 1993.*

Creighton Proteins: Structure and Molecular Principles, WH Freeman and Co NY 93–94, 1983.*

Creighton Prog Biophys Molec Biol 33:231–233, 1975.*

* cited by examiner

INHIBITOR
○ TYPE 3 VIRUS
● 3 HA1 VIRUS

PERCENT INHIBITION vs VIRUS CONCENTRATION (PARTICLES/ml)

*Fig. 2A*

- CONTROL PEPTIDE IMMUNE
○ $V_L$-CSA IMMUNE
△ $V_H + V_L$-CSA IMMUNE
▲ REO PEPTIDE IMMUNE

TYPE 1 VIRUS

Fig. 13A

- CONTROL PEPTIDE IMMUNE
- ○ $V_L$-CSA IMMUNE
- △ $V_H + V_L$-CSA IMMUNE
- ▲ REO PEPTIDE IMMUNE

TYPE 1 VIRUS

*Fig. 14B*

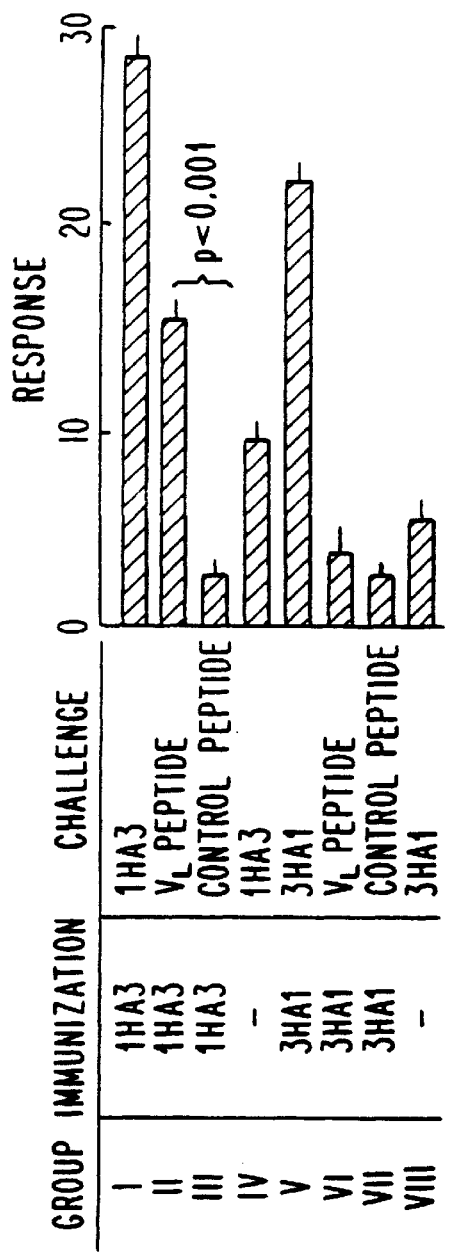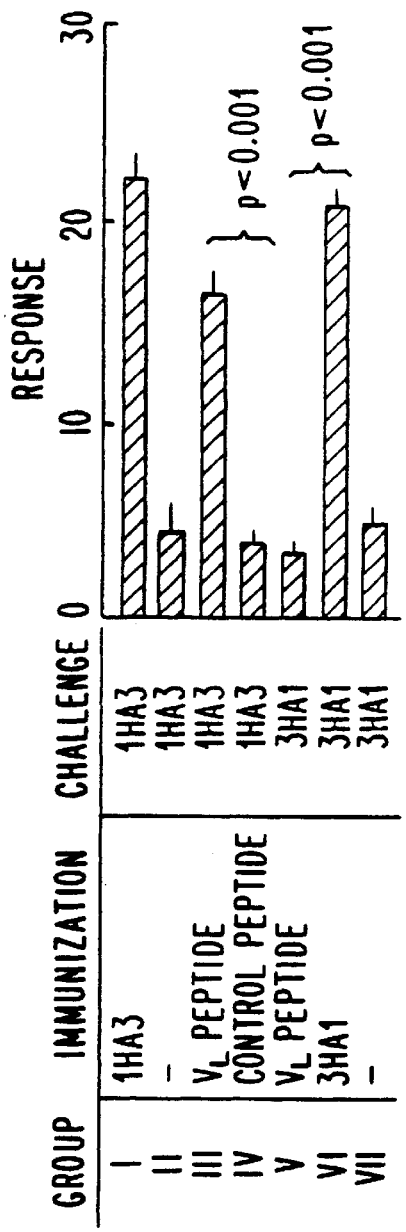
Fig. 15A
Fig. 15B

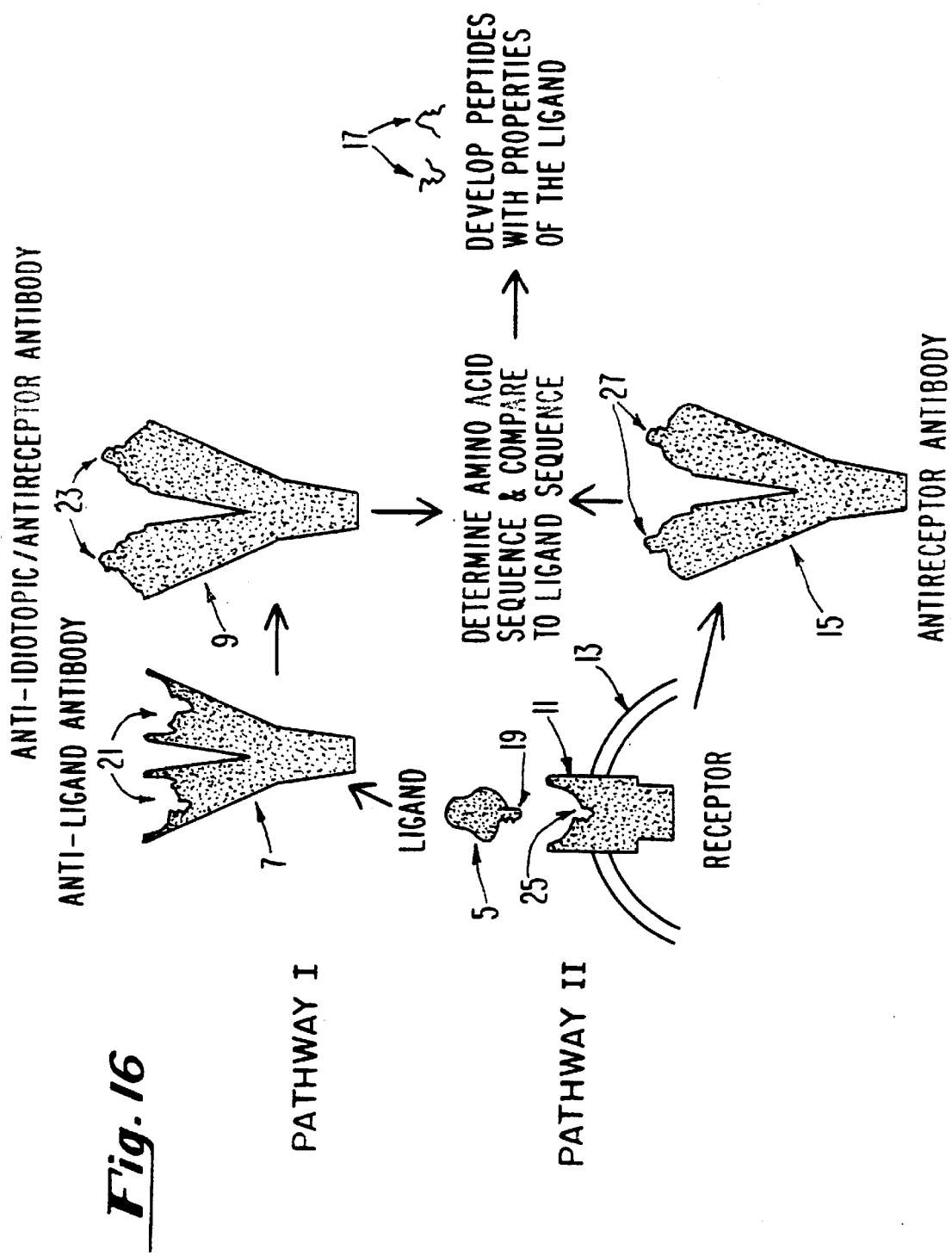

BIOLOGICALLY ACTIVE COMPOUNDS AND METHODS OF CONSTRUCTING AND USING THE SAME

CROSS REFERENCE TO RELATED APPLICATIONS

This Application is a continuation of U.S. Ser. No. 07/940,654 filed Sep. 3, 1992, allowed as U.S. Pat. No. 5,637,677, which is a Continuation-In-Part Application of U.S. patent application Ser. No. 07/702,833, filed May 20, 1991, abandoned, which is a Continuation Application of U.S. patent application Ser. No. 07/326,328, filed Mar. 21, 1989, abandoned, which was a Continuation-In-Part Application of U.S. patent application Ser. No. 07/074,264, filed Jul. 16, 1987, abandoned. This Application is a Continuation-In-Part Application of U.S. patent application Ser. No. 07/462,542, filed Jan. 9, 1990, abandoned, which is a Divisional Application of U.S. patent application Ser. No. 07/074,264, filed Jul. 16, 1987, abandoned. This Application is a Continuation-In-Part Application of U.S. patent application Ser. No. 07/648,303, filed Jan. 25, 1991, abondoned, which is a File Wrapper Continuation Application of U.S. patent application Ser. No. 07/074,264, filed Jul. 16, 1987, abandoned. This Application is a Continuation-In-Part Application of U.S. patent application Ser. No. 07/685,881, filed Apr. 15, 1991, abandoned, which is a Continuation Application of U.S. patent application Ser. No. 07/574,391, filed Aug. 27, 1990, abandoned which was a File Wrapper Continuation Application of U.S. patent application Ser. No. 07/194,026 filed May 13, 1988, allowed as U.S. Pat. No. 4,962,510 which was a Continuation-In-Part Application of U.S. patent application Ser. No. 07/074,264, filed Jul. 16, 1987, abandoned. This Application is a Continuation-In-Part Application of U.S. patent application Ser. No. 07/583,626, filed Sep. 14, 1990, abandoned. Each of the above listed patent applications is incorporated herein by reference.

ACKNOWLEDGMENT OF GOVERNMENT RIGHTS

This invention was made with Government support under grant 5R01EY08191 awarded by the National Institutes of Health. The Government has certain rights in this invention.

FIELD OF THE INVENTION

The present invention relates to methods of identifying portions of proteins involved in protein-protein interactions, to methods of constructing biologically active peptides involved in protein-protein interactions, and to biologically active peptides.

BACKGROUND OF THE INVENTION

Protein binding or protein-protein interactions can be broadly defined as the discrete interaction of the surface of one protein with the surface of another protein. Such discrete interaction arises when residues of one protein are proximally located to residues of another protein and attractive forces between the residues such as vander Waals forces, ionic bonds and hydrogen bonds exist. Specific protein-protein interactions which occur in higher living organisms include but are not limited to those in which involve: a receptor-binding protein binding to a receptor; a pathogen antigen binding to a host cell receptor; protein interactions at cellular attachment sites; and, adhesion proteins interactions.

Examples of receptor-binding proteins, hereinafter also referred to as ligands, include cytokines, hormones and growth factors. These proteins bind to receptors on cells and cause changes in cellular activity or function. For example, cytokines are a variety of proteins which are cellular messengers, each cytokine having a specific effect upon a cell. Likewise, hormones and growth factors are also messengers which affect the function and activity of cells.

Pathogens are infectious organisms, such as bacteria, fungi, parasites, and viruses and, additionally, neoplasms, all of which express specific antigens. Such typically, there are specific sites on antigens, hereinafter referred to as binding epitopes or epitopes, which bind to a complementary portion of a cellular protein called a receptor site.

A great deal of effort has been expended in search of compounds which specifically either simulate, that is mimic, or block protein-protein interactions in cells.

With respect to cytokines, hormones and growth factors, a great deal of effort has been made to purify the natural proteins from natural sources or to synthetically produce them by chemical means or using recombinant DNA technology. While some success has been achieved, these molecules are quite large, difficult to handle and expensive to obtain. A great deal of effort is also directed at discovering synthetic ligands which either mimic the activity of natural proteins or which block the activity of natural proteins. Blocking natural protein activity can be achieved by either competing for the receptor with an inactive ligand (antagonist) or by having an agent bind to the natural protein and thereby prevent it from binding to the receptor.

There is a need for synthetic peptides and/proteins which mimic the activity of the natural biologically active proteins which interact with receptors. Such mimicking molecules would be useful as agents to affect the cells in the same way as the natural protein. Likewise, the discovery of antagonists, that is, molecules which block the receptor without having an effect on cellular function or activity would be useful. Furthermore, the discovery of agents which specifically interact with biologically active proteins and thereby render them unable to bind to receptors is also desirable. Molecules that prevent binding by a natural biologically active protein to its receptor in cases where the natural protein is believed to an agent associated with a disease condition or disorder are useful as drugs for preventing or treating such disease conditions or disorders. A great deal of knowledge has been developed in the field of immunology, including at the molecular level.

Advances in molecular biology have indicated that immunoglobulins, major histocompatibility complex antigens and T-cell receptors are all members of a family of molecules referred to as the immunoglobulin superfamily. During evolution, it is likely that a single, useful gene duplicated, and its copies diverged to create related molecules with distinct functions. Accordingly, immunoglobulins, which are agents of humoral immunity; T-cell receptors, which are associated with humoral as well as cellular immunity; and major histocompatibility complex molecules, involved in antigen presentation and the discrimination between self and nonself, all share homologies inherited from their common ancestor and exhibit related biological functions.

Of the members of the superfamily, the structure and function of immunoglobulins is best understood.

Immunoglobulin molecules consist of a constant region and a variable region. The constant region is associated with cellular effector functions whereas the variable region participates in antigen recognition and binding.

Immunoglobulins of the most common class, IgG, consist of two heavy chains and two light chains linked together by noncovalent associations and also by covalent disulfide bonds. Each of the chains possesses a constant as well as a variable region. In the immunoglobulin molecule, the variable region is subdivided into framework regions, which are similar in structure among immunoglobulins, and hypervariable, complementarity determining regions (CDRs) which participate directly in antigen binding in the immunoglobulin active site.

X-ray crystallographic studies of purified immunoglobulin molecules have indicated that the active site is a crevice formed by the heavy and light chain variable regions, and that the dimensions of the active sites vary among immunoglobulin molecules consequent to amino acid sequence variations (Hood et al., 1978, in "Immunology," The Benjamin/Cummings publishing Co., Inc., Menlo Park, p. 208). Amino acid sequence, crystallographic structure, and specially designed hapten probes have been used in conjunction with computer analysis to elucidate the relationship between an immunoglobulin and the antigen which it recognizes.

Pathogens generally express antigens which are recognized by host immune systems as foreign and become the target of an immunological response to eliminate the infectious pathogen. Pathogen antigens often bind to cellular receptors on a host's cells as part of the process of infection of the host by the pathogen. In order to immunize the host and reduce the effectiveness of the pathogen to mount a challenge to the host, a number of vaccination strategies have been devised.

Several strategies have been employed to develop safe, effective vaccines against viral and bacterial pathogens. At present most vaccines in use consist of live attenuated pathogens, killed pathogens, components of a pathogen, or modified toxins (toxoids). See Institute of Medicine, "Vaccine Supply and Innovation", Washington, D.C.: National Academy Press (1985). While these preparations have been successfully used for many infectious diseases, many pathogens exist where these approaches have not worked or have not been applicable. Certain pathogens are potentially too dangerous to contemplate the use of attenuated or even inactivated preparations. The risk of developing cancer from immunization with certain retroviruses, or of developing acquired immunodeficiency syndrome (AIDS) from immunization with human immunodeficiency virus (HIV) underscores the drawbacks associated with the use of whole virus preparations for vaccination. In addition many pathogens display a marked antigenic heterogeneity that makes effective vaccination difficult. These considerations have led us to seek alternative method for effective immunization.

The idiotype network theory of N. K. Jerne, Ann. Immunol. (Paris) 125:337–389, (1974), implies that an anti-idiotypic antibody raised against a neutralizing antibody specific for a pathogen would mimic that pathogen immunologically. Immunization with the anti-idiotype should result in the development of a significant anti-pathogen response with the elicitation of neutralizing antibodies and cell-mediated immunity. In recent years there have been several examples where this strategy has been effective, including reovirus type 3. See Sharpe, A. H., et al., J. Exp. Med. 160:195–205 (1984); Kauffman, R. S., et al., J. Immunol., 131:2539–2541, (1983); and Gaulton, G. N., et al., J. Immunol. 137:2930–2936. With respect to Sendai virus, see Ertl, H. C. and Finberg, R. W., Proc. Natl. Acad. Sci. USA 81:2850–2854 (1984). For report relating to rabies see Reagen, K. J. et al., J. Virol. 48:660–666 (1983). This approach has been discussed in connection with polio virus in Uydeltaag, F.G.C.M. and Osterhaus, A.D.M.E., J. Immunol. 134:1225–1229 (1985).

One of the key aspects of this approach is that a portion of the anti-idiotype mimics a portion of the pathogen antigen and induces a neutralizing response. Thus a potent anti-idiotype vaccine would seem to be an ideal immunogen in cases where intact pathogen could not be used or where irrelevant non-neutralizing epitopes dominate the immune response. However, the practical application of anti-idiotypes as vaccine has been limited by the difficulties in making human monoclonal antibodies and in the danger of producing serum sickness by using xenogeneic antibodies.

Another method currently under intensive investigation is the use of synthetic peptides corresponding to segments of the proteins from pathogenic microorganisms against which an immune response is directed. This approach has been successful in several instances including feline leukemia virus (Elder, J. H. et al., J. Virol. 61:8–15, 1987), hepatitis B (Gerin, J. L., et al., Proc. Natl. Acad. Sci. USA, 80:2365–2369 1983), Plasmodium falciparum (Cheung, A., et al., Proc. Natl. Acad. Sci. USA 83:8328–8332, 1986), cholera toxin (Jacob, C. O., et al., Eur. J. Immunol. 16:1057–1062, 1986) and others. When these peptides are capable of eliciting a neutralizing immune response they appear to be ideal immunogens. They elicit a specific response and typically do not lead to deleterious effects on the host. However, it can be difficult to predict which peptide fragments will be immunogenic and lead to the development of a neutralizing response.

It would be desirable to develop immunogens that elicit a response to specific neutralizing epitopes without causing responses to extraneous epitopes that could "dilute" the specific response or lead to harmful immune complex formation.

The present invention relates to a method of identifying specific linear and constrained discrete portions of a biologically active proteins involved in protein-protein interactions. By identifying such specific and discrete portions, biologically active peptides can be constructed which mimic the biological activity of the biologically active protein or which block the activity of the biologically active protein. Thus, biologically active peptides can be constructed which act as ligands that act on mammalian cells by binding to the receptor sites of those cells to alter or affect their function or behavior, or to prevent the binding of the natural biologically active protein to the cellular receptor, thereby preventing the biologically active protein from affecting the cell.

The present invention relates to a method of identifying specific linear and constrained discrete portions of pathogen antigens which either serve as epitopes for neutralizing antibodies or which are involved in pathogen binding to host cell receptors. By identifying discrete portions of pathogen antigens which are neutralizing epitopes, biologically active peptides can be constructed which are useful as components of vaccines against the pathogen. An effective neutralizing immune response will be elicited in a vaccinated individual. By identifying discrete portions of pathogen antigens which are involved in pathogen binding to host cell receptors, biologically active peptides can be constructed which are useful as agents which block pathogen attachment to cellular receptors. Additionally, by identifying discrete portions of pathogen antigens which are involved in pathogen binding to host cell receptors, biologically active peptides can be constructed which mimic pathogen antigens and act on mammalian cells by binding to the receptor sites of those cells to alter or affect their function or behavior, or which prevent or alter the effect which pathogen antigens would otherwise have upon those cells.

The present invention relates to the field of biologically active peptides which have some shared and/or similar amino acid sequences to the amino acid sequences of cellular receptor sites and thereby compete with such cellular receptors for binding to either biologically active proteins or pathogen antigens. In addition, the invention relates to the field of biologically active peptides which have some shared and/or similar amino acid sequences to the amino acid sequences of the ligand surface that attaches to a cellular receptor site. The ligand mimetic peptide can be used as a stimulant or inhibitor of that receptor. Where the biologically active peptide competes in pathogen/receptor binding, the biologically active peptides are useful to prevent pathogen attachment and thereby prevent infection. Where the biologically active peptide competes in biologically active protein/receptor binding, the biologically active peptides are useful to prevent ligand/receptor binding and thereby prevent the effect on cellular function or behavior normally associated with the biologically active protein/receptor binding.

SUMMARY OF THE INVENTION

One embodiment of the invention relates to a method of constructing a peptide capable of eliciting a neutralizing immune response against a pathogen in a mammal. A method of the invention comprises the steps of identifying a neutralizing epitope of a pathogen antigen by first generating a neutralizing antibody specific for a pathogen, then generating an anti-idiotypic antibody specific for the neutralizing antibody and then identifying the CDR amino acid sequence of the anti-idiotypic antibody that corresponds to an amino acid sequence of a pathogen antigen. Using that information, a peptide is synthesized that corresponds to or is identical to the portions of the antibody and antigen that correspond to each other.

Another embodiment of the invention relates to a method of immunizing a host mammal against infection by a pathogen that comprises such an antigen by inoculating a mammal with a peptide that corresponds to the neutralizing epitope of a pathogen antigen.

Another embodiment of the invention is a method of constructing a peptide capable of preventing a pathogen or a biologically active protein from binding to a cellular receptor. A method of the invention comprises identifying an amino acid sequence of a portion of a pathogen antigen or a biologically active protein which binds to the cellular receptor by first generating an anti-receptor antibody capable of preventing a pathogen or a biologically active protein from binding to the cellular receptor and then identifying an amino acid sequence of the anti-receptor antibody that corresponds to an amino acid sequence of the pathogen antigen or the biologically active protein. Using that information, a peptide is synthesized that corresponds to or is identical to the portions of the antibody and antigen that correspond to each other.

Another embodiment of the invention relates to a method of treating a host mammal to prevent or reduce the severity of an infection by a pathogen by constructing a peptide capable of preventing a pathogen from binding to cellular receptor and administering the synthetic peptide to a mammal in an amount effective to prevent or reduce the likelihood that the pathogen will infect cells of the host.

Another embodiment of the invention relates to a method of constructing a peptide capable of preventing a pathogen or a biologically active protein from binding to a cellular receptor. A method of the invention comprises identifying an amino acid sequence of a cellular receptor which directly interacts with an amino acid sequence of a pathogen antigen or a biologically active protein during receptor binding by first generating an antibody specific for the pathogen or the biologically active protein which is capable of preventing the pathogen or the biologically active protein form binding to the cellular receptor and then identifying an amino acid sequence of the CDR of the antibody which corresponds to an amino acid sequence of the cellular receptor. Using that information, a peptide is synthesized that corresponds to or is identical to the portions of the antibody and antigen that correspond to each other.

Another aspect of the invention relates to a method of constructing a biologically active peptide comprising the steps of identifying an amino acid sequence of a biologically active portion of a biologically active protein which directly interacts with a cellular receptor when the biologically active protein binds to the cellular receptor, wherein such binding causing an effect on an activity or function of cell. The amino acid sequence of the biologically active portion of the biologically active protein identified by first generating an anti-receptor antibody against a cellular receptor, the anti-receptor antibody being capable of effecting an activity or function of a cell and then identifying an amino acid sequence of the CDR of the anti-receptor antibody that corresponds to an amino acid sequence of the biologically active protein. Using that information, a peptide is synthesized that is corresponds to or is identical to the portions of the antibody and antigen that correspond to each other.

Another embodiment of the invention relates to a method of effecting or altering activity or function of a mammalian by contacting a cell with an amount of such a biologically active peptide sufficient to effect or alter activity or function of the cell.

The invention relates to synthetic biologically active peptides comprising or consisting essentially of amino acid sequence that correspond to an amino acid sequence of an antigen or biologically active protein and an amino acid sequence of an anti-idiotypic antibody or an anti-receptor antibody.

BRIEF SUMMARY OF THE FIGURES

FIG. 1 illustrates the specific binding of 9BG5 to peptides, determined by radioimmunoassay as noted in the experimental procedures described hereinafter; CPM of 9BG5 bound to blank wells was subtracted from CPM of 9BG5 bound to peptide coated wells; non-specific binding to peptides was corrected for by subtracting from the value a similar value determined for an isotype-matched control monoclonal antibody UPC10; specific CPM of 9BG5 bound to peptide coated wells is shown using the amount of 9BG5 added to each well in a final volume of 50 $\mu$l.; mean ±SD for duplicate wells is shown.

FIG. 2A and 2B illustrate the binding of $V_L$-BSA to type 3 reovirus receptor as determined by its ability to compete for binding with anti-reovirus type 3 receptor antibody 87.92.6.; R1.1 cells ($10^7$/ml) were incubated in 1% BSA in the presence or absence of 200 $\mu$g/ml $V_L$-BSA or $V_H$-BSA as indicated for 45 minutes; monoclonal antibodies were added at the concentrations noted for an additional 30 minutes; the cells were washed twice and a 1:200 dilution of FITC-goat anti-mouse Fab was added for 30 minutes; the cells were washed twice and analyzed for fluorescence intensity on a FACS analyzer; percent maximal cell staining was determined as the ratio of the percent of the cells positive on FACS analysis at the antibody concentration noted to the maximal percent of cells judged positive at saturating doses of monoclonal antibody in the absence of competitors ([% positive at concentration divided by maximal % positive] ×100); the maximal percent positive values were as follows: 2a - 15.3%, 2b - 97%, 2c - 24%.

FIGS. 5A–D show modulation of reovirus type 3 receptor by peptides.

Figure 6:
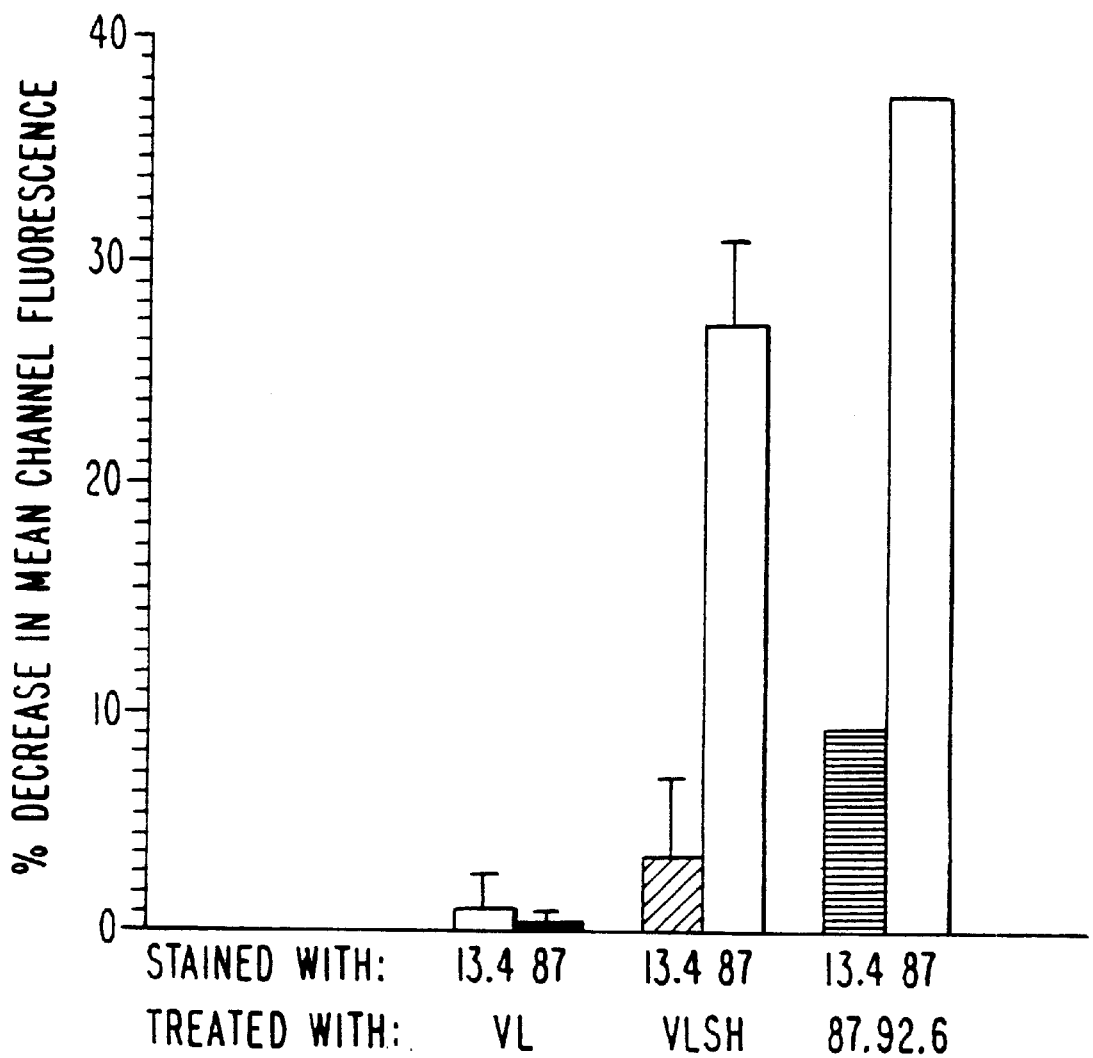

FIG. 6 shows modulation of the reovirus type 3 receptor by peptides and antibody.

Figure 7A:
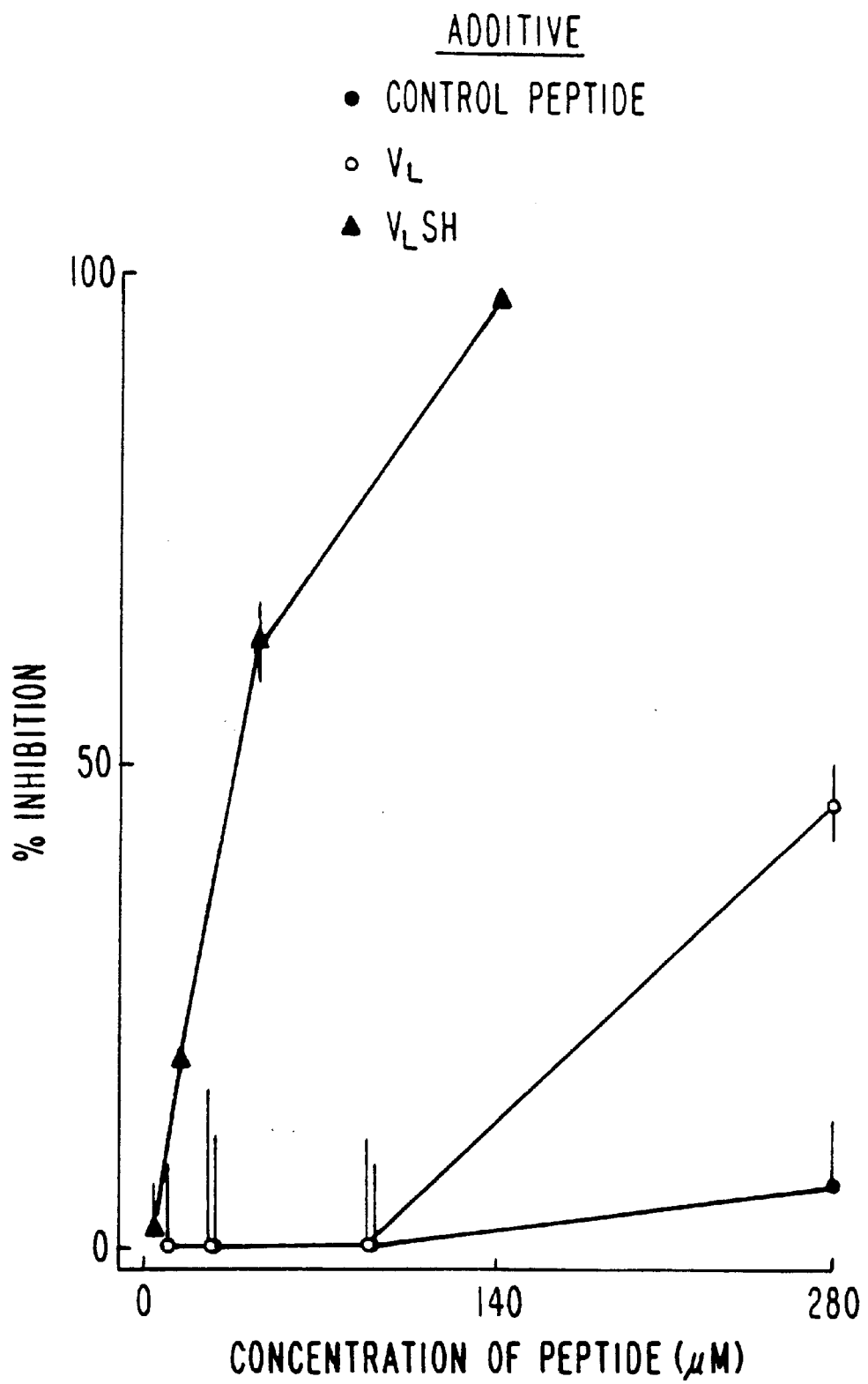
Figure 7B:
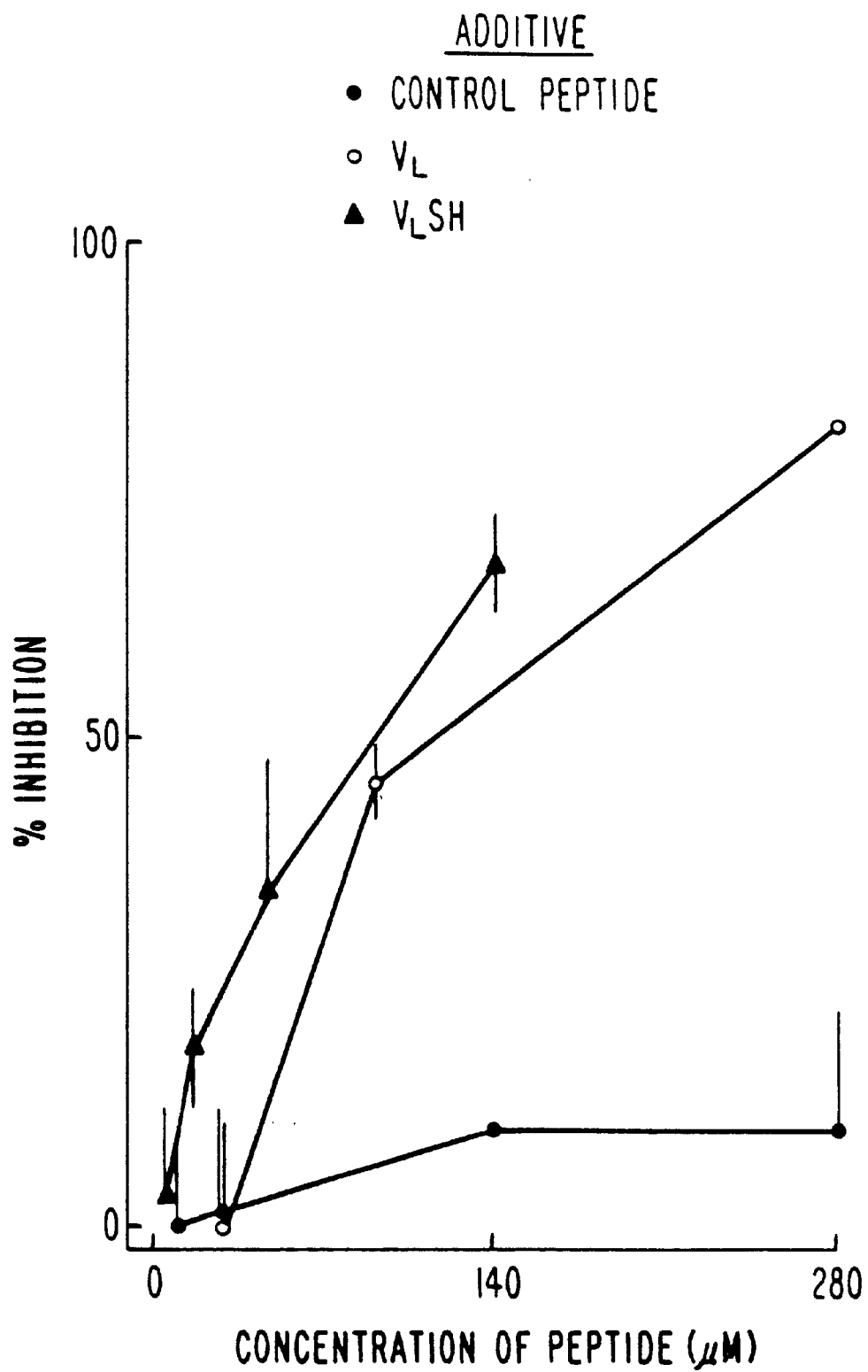

FIGS. 7A and 7B show inhibition of lymphocyte proliferation.

Figure 8A:
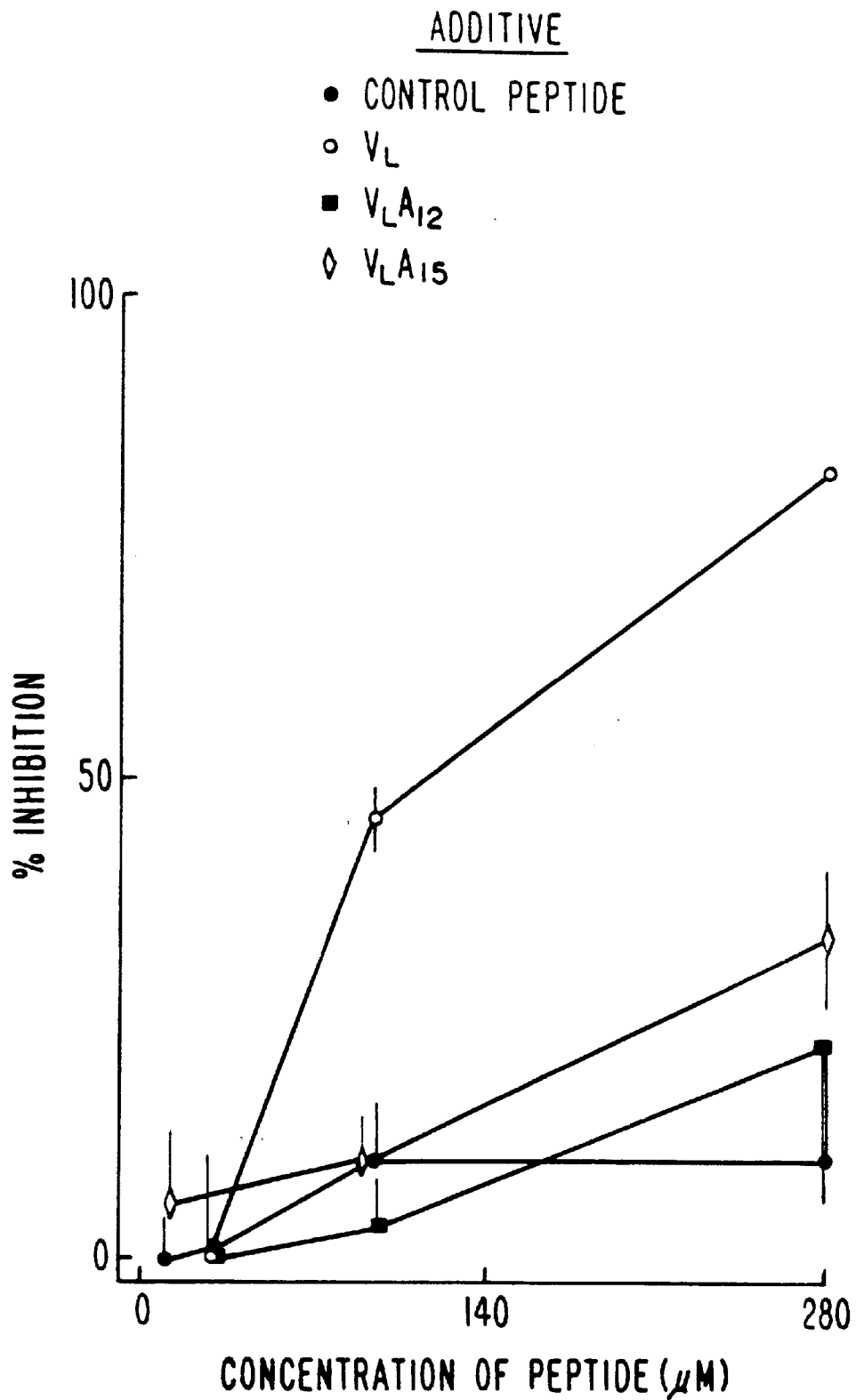
Figure 8B:
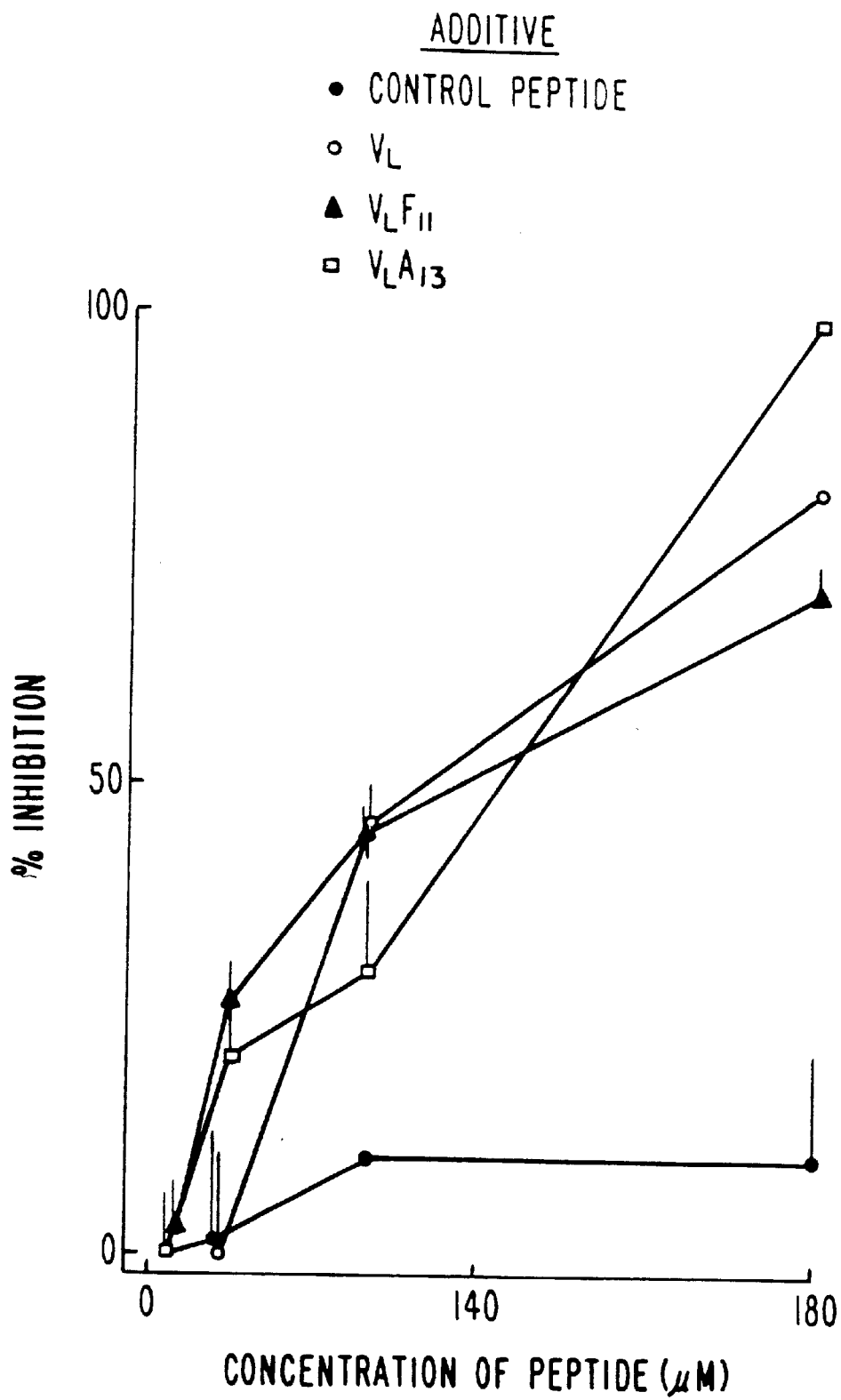

FIGS. 8A and 8B show peptide inhibition of con A induced lymphocyte proliferation.

Figure 9:
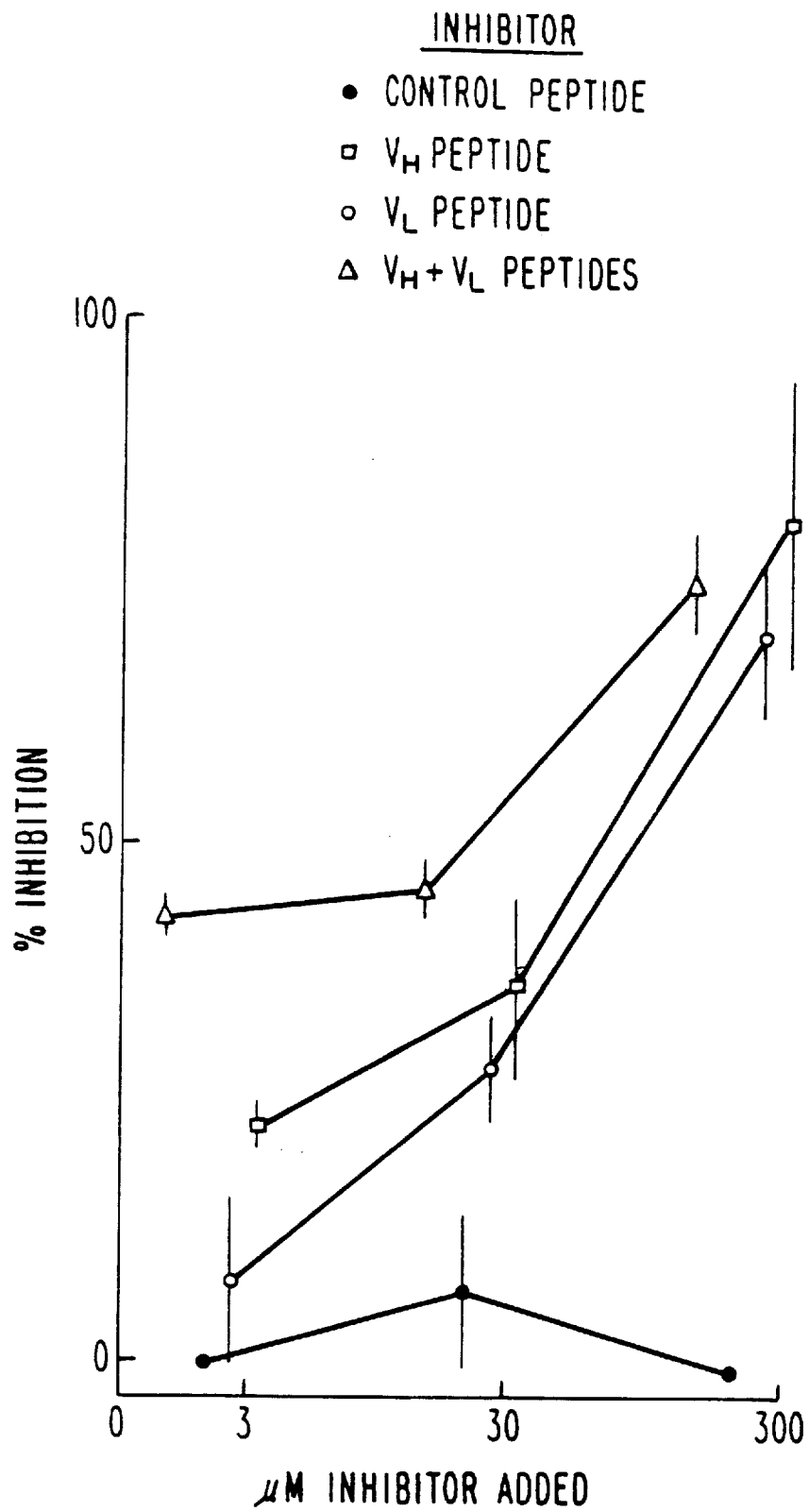

FIG. 9 shows competition of binding of 9BG5 antibody to 87.92.6 antibody coated wells in the presence of peptide inhibitors.

Figure 10A:
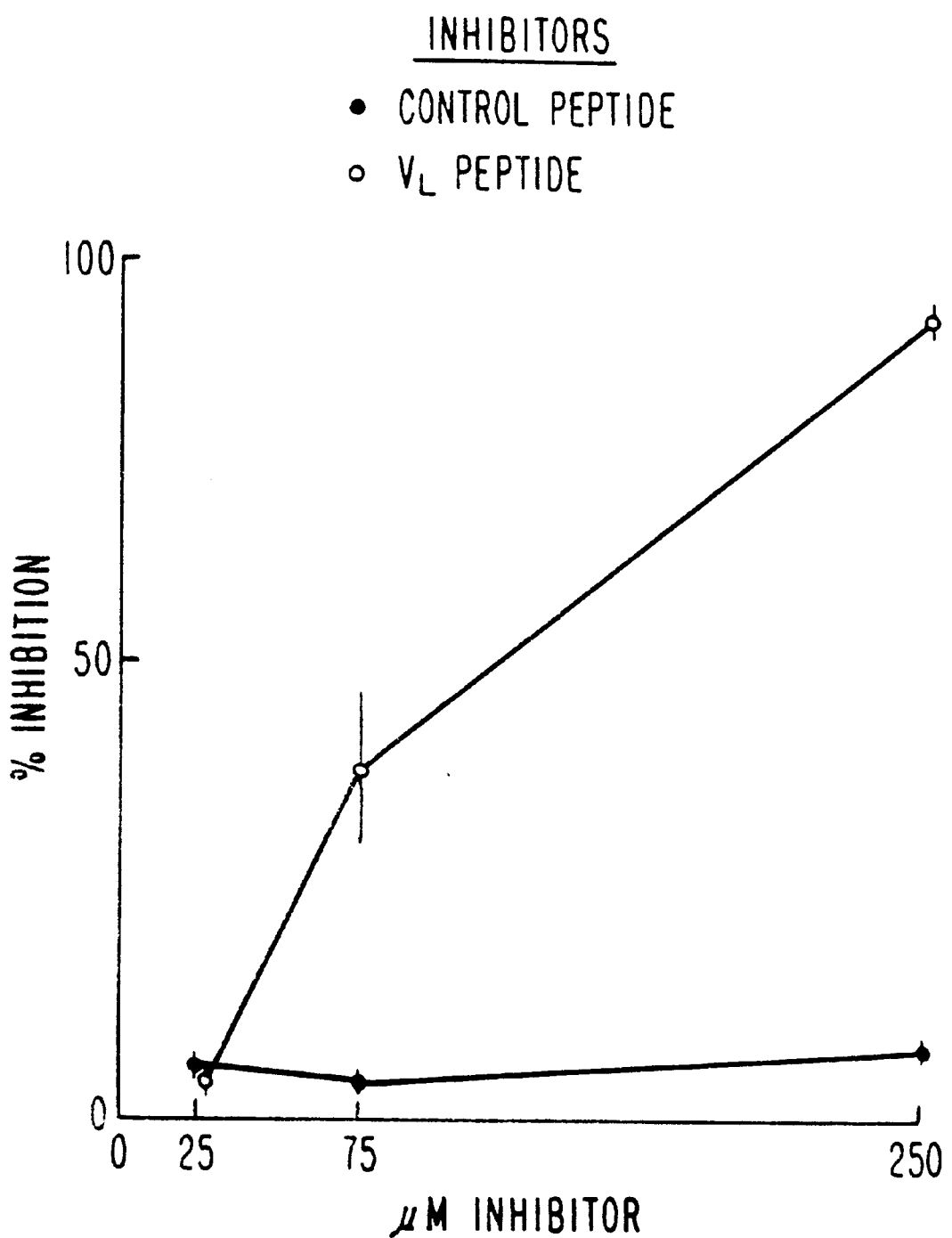
Figure 10B:
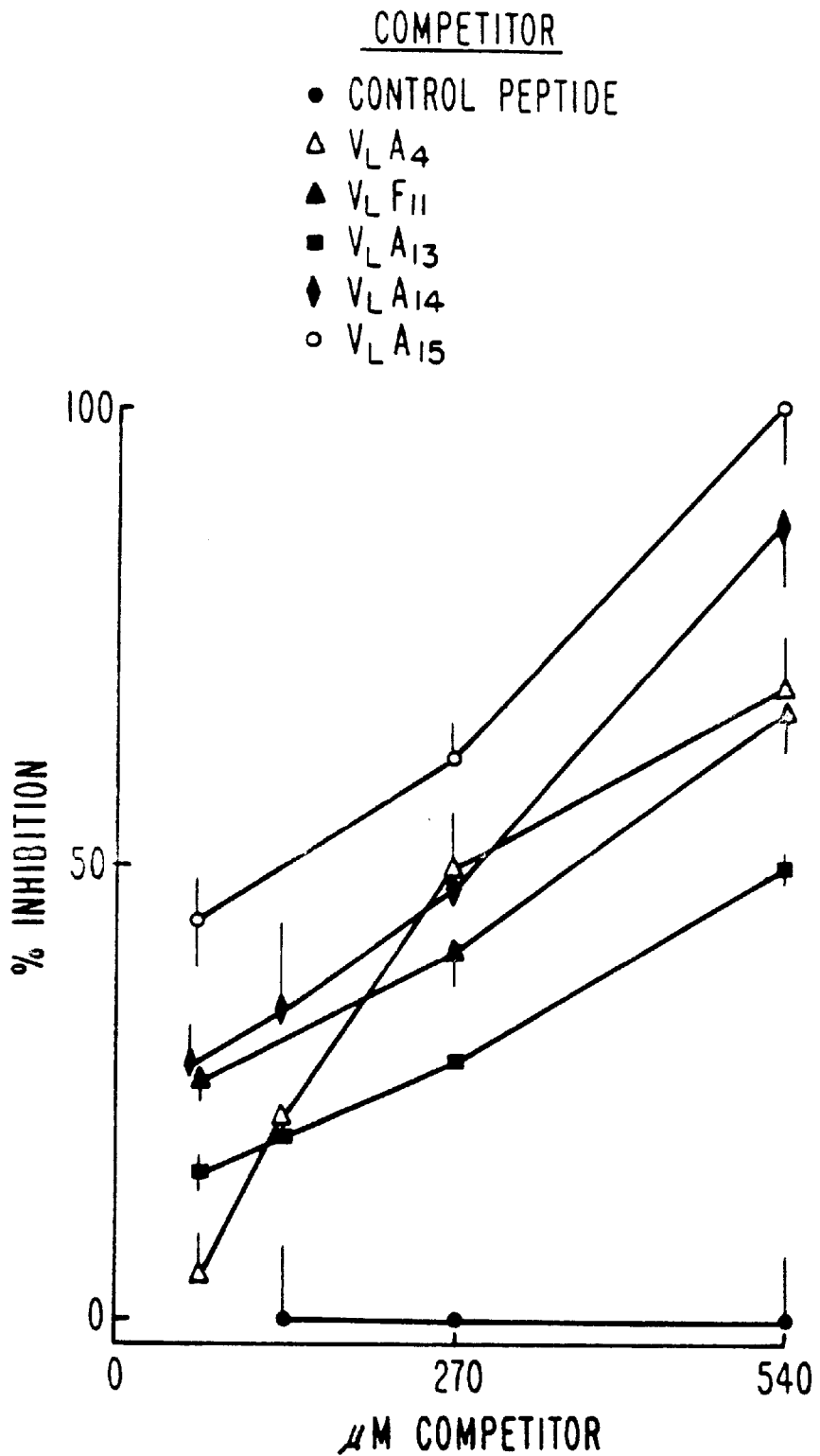
Figure 10C:
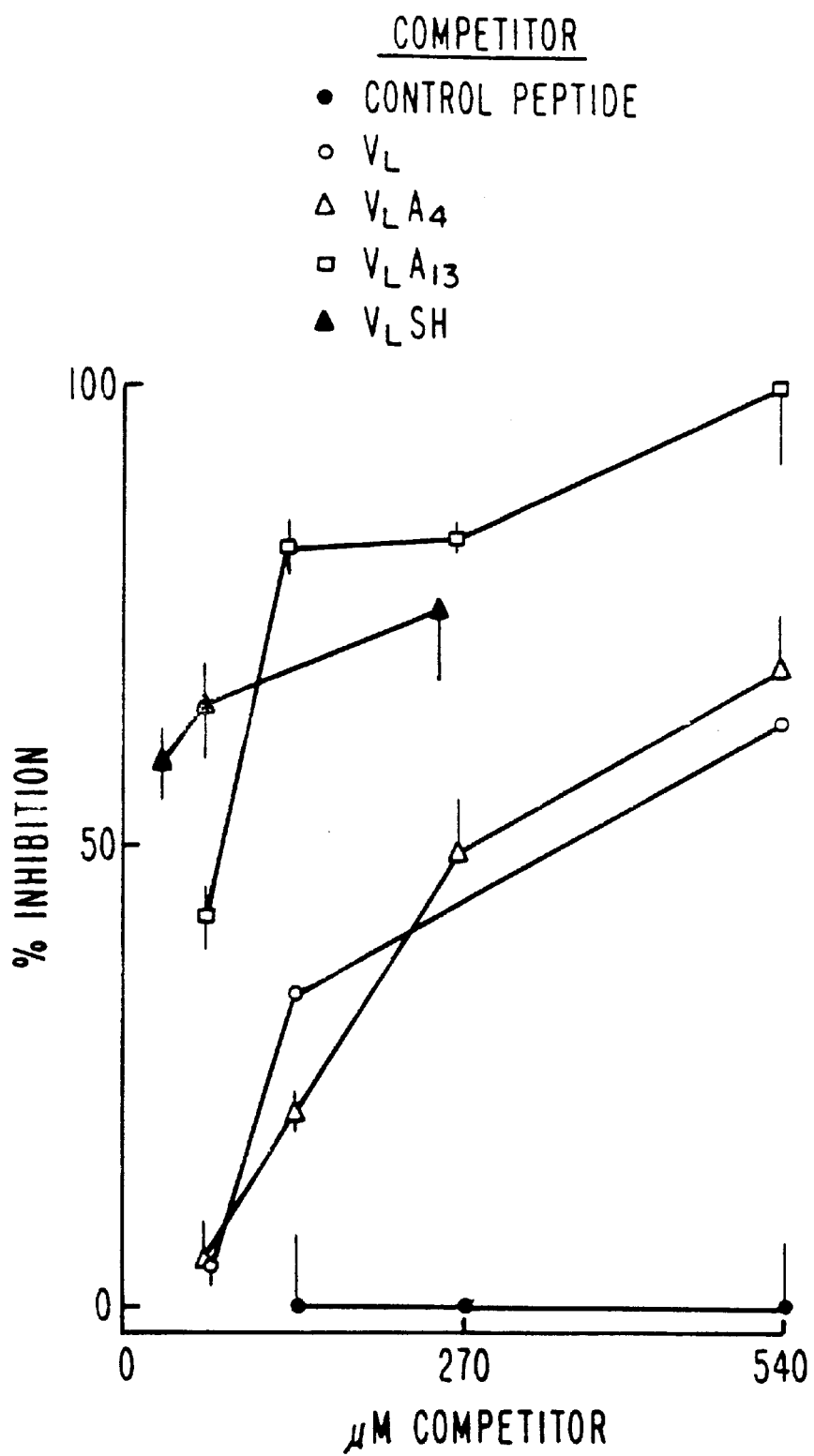

FIGS. 10A–C show $V_L$ and variant peptide inhibition of binding of reovirus type 3 particles to 9BG5.

Figure 11A:
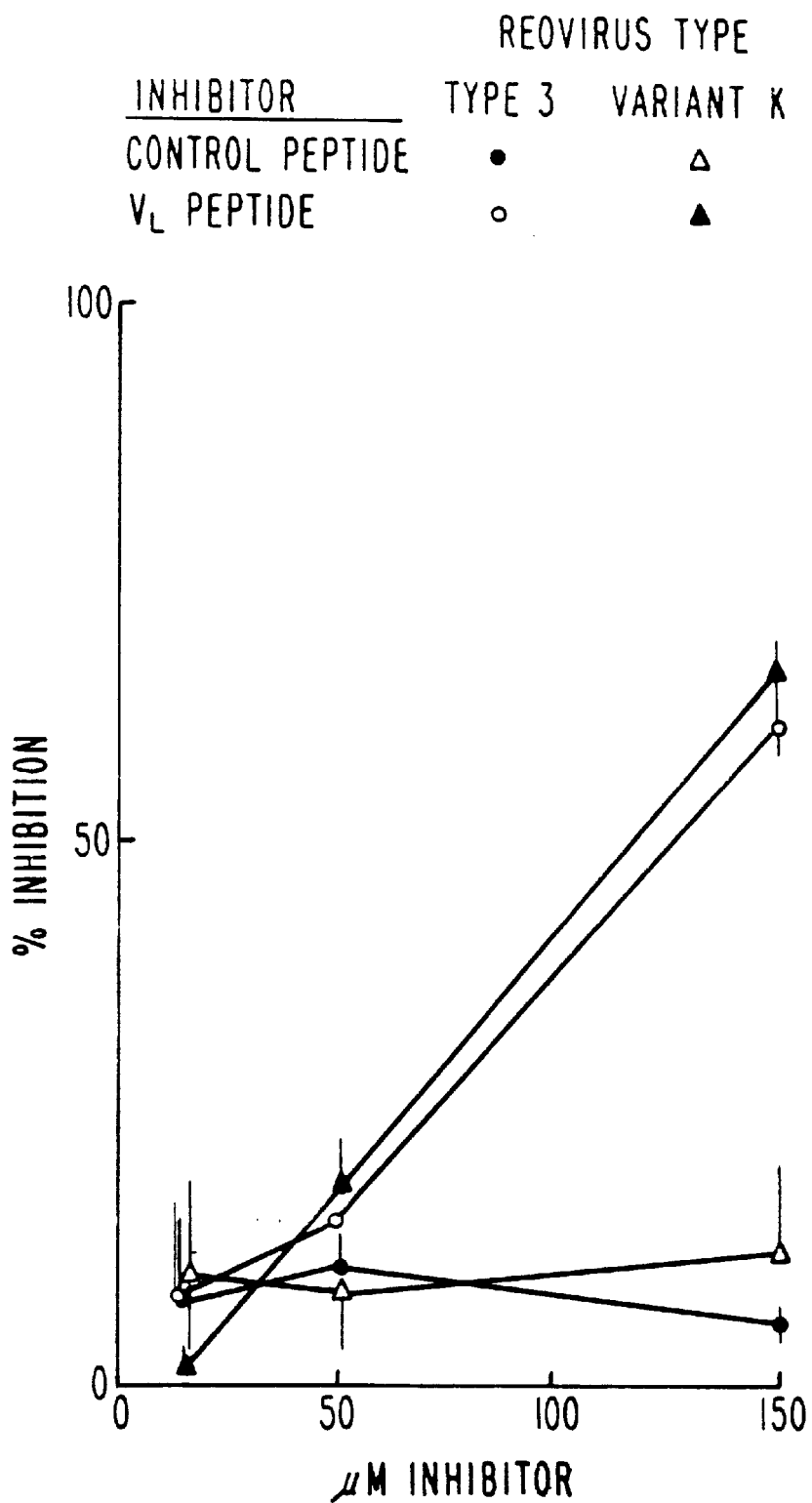
Figure 11B:
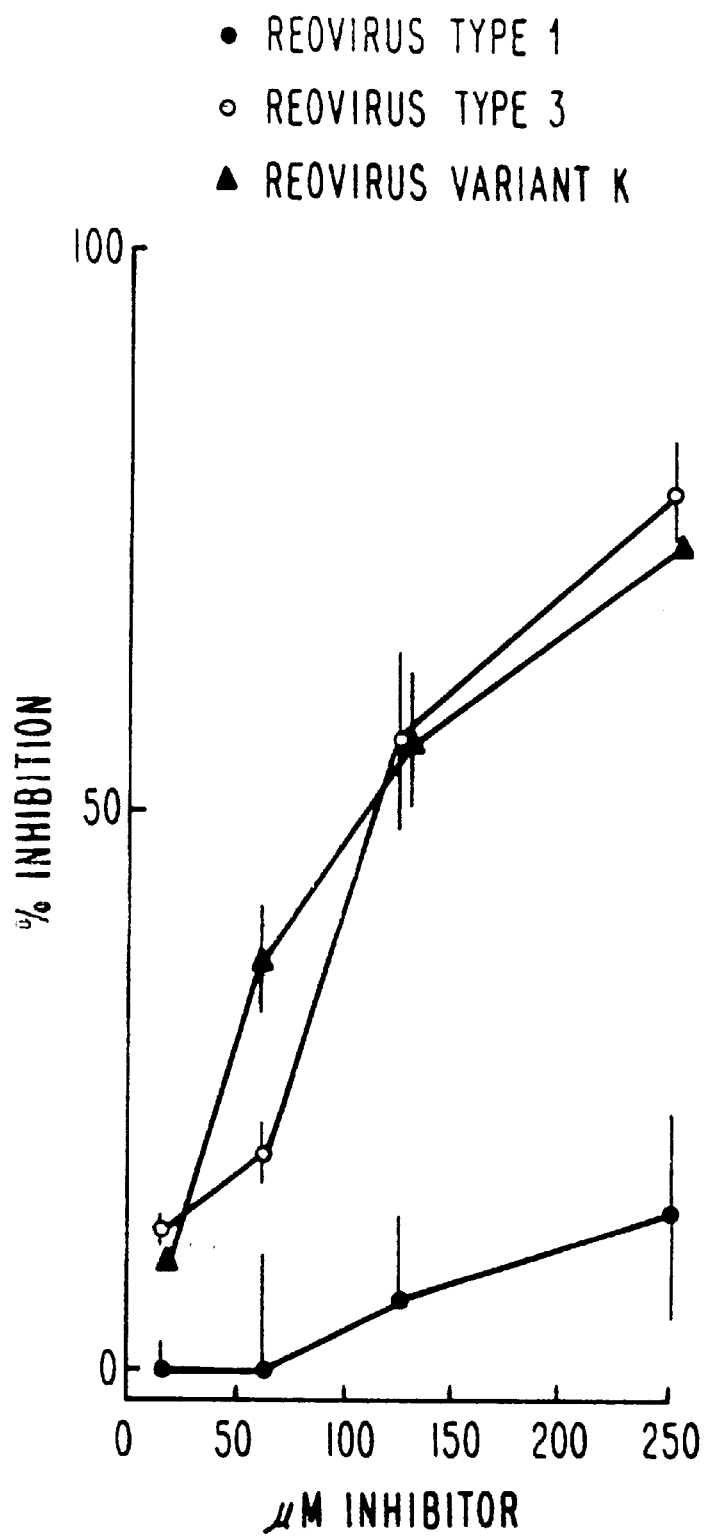
Figure 11C:
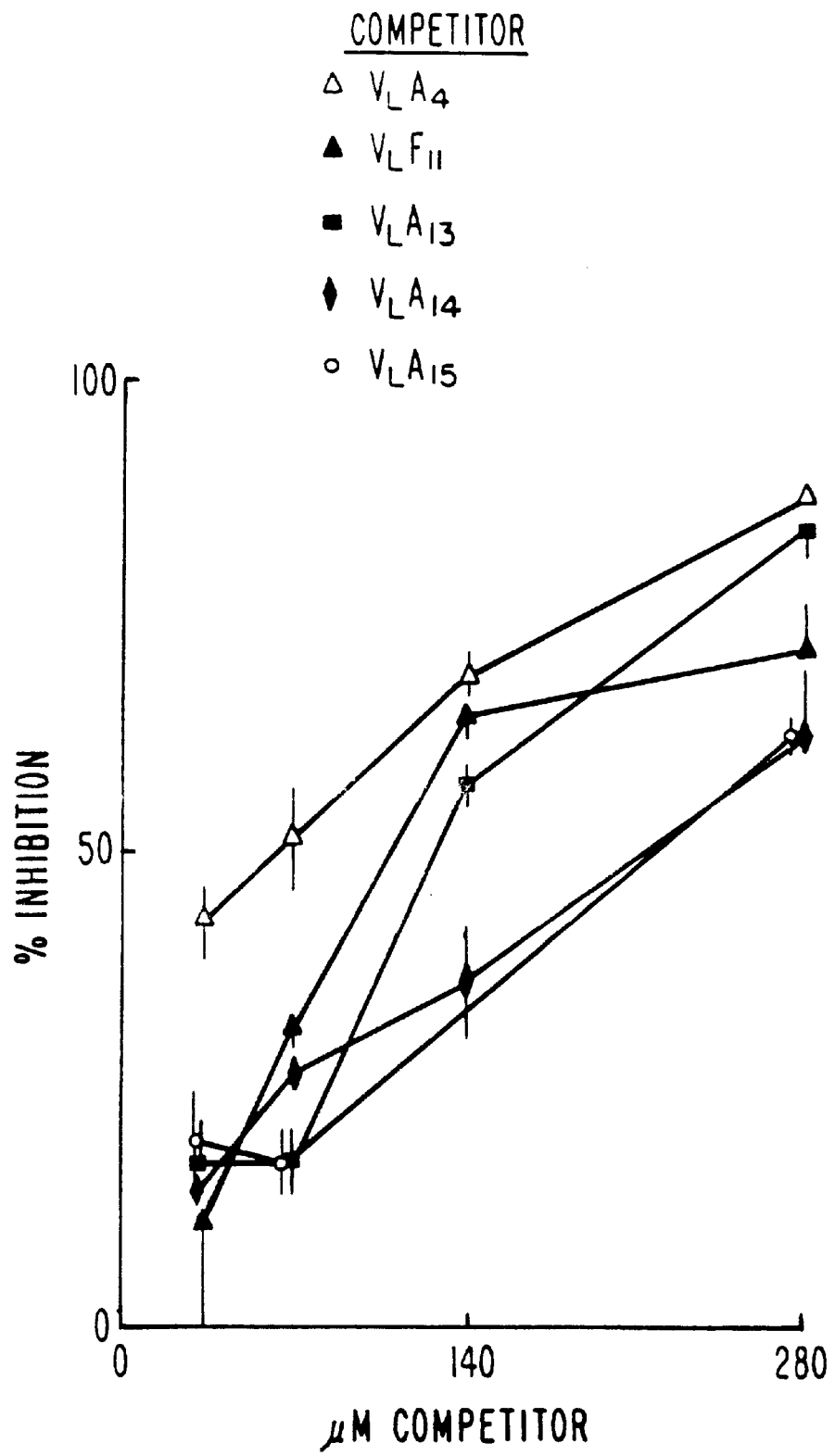
Figure 11D:
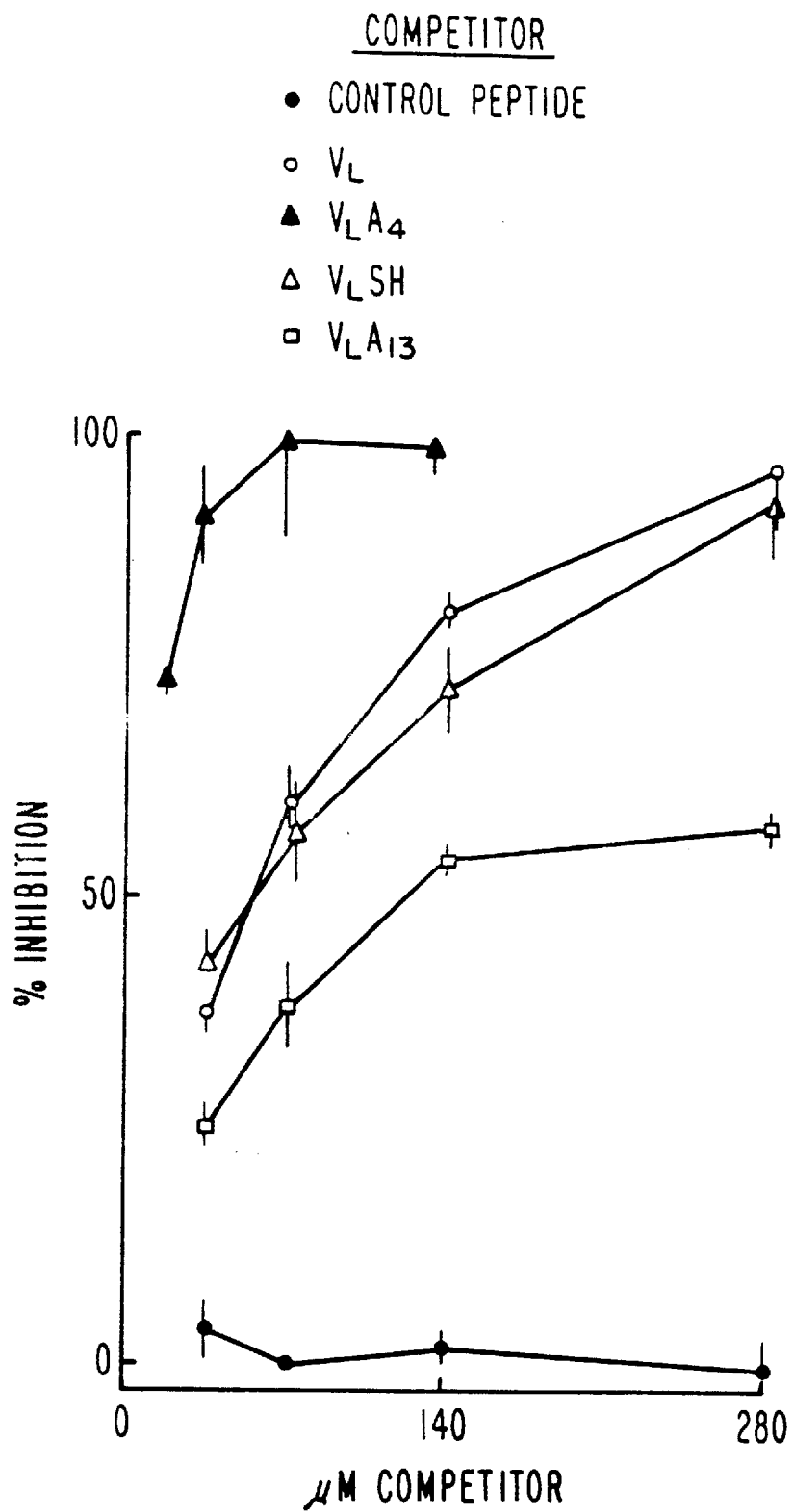

FIGS. 11A and 11B show in (a) and (b) $V_L$ peptide inhibition of binding of reovirus type 3 and variant K to L cells; FIGS. 11C and 11D show $V_L$ variant peptide inhibition of binding of reovirus type 3 to murine L cells.

Figure 12A:
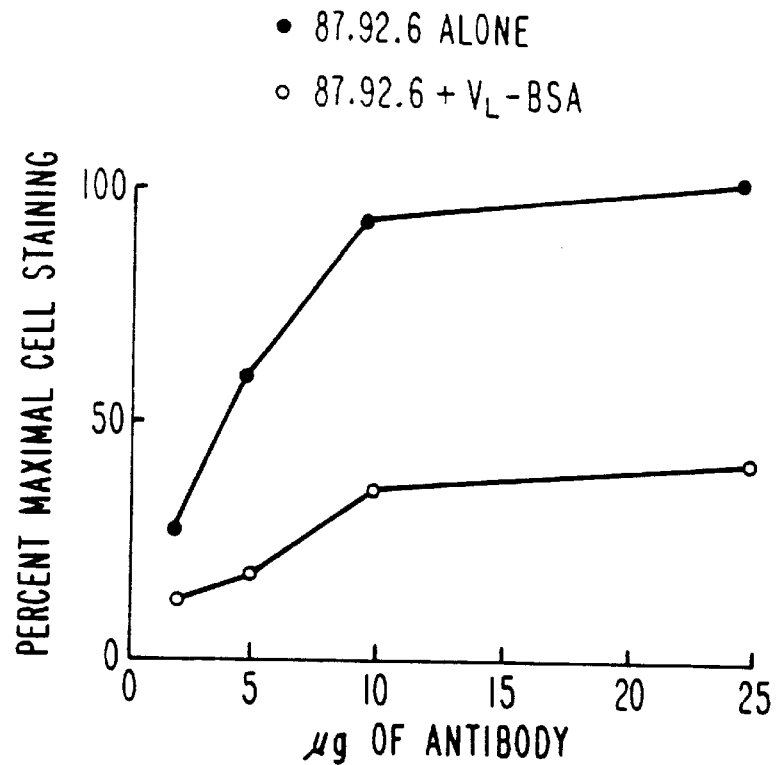
Figure 12B:
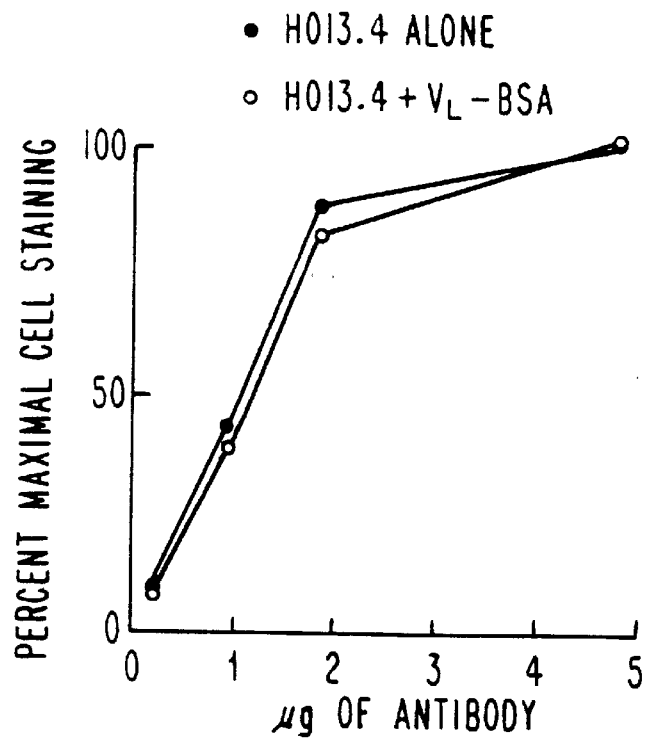
Figure 12C:
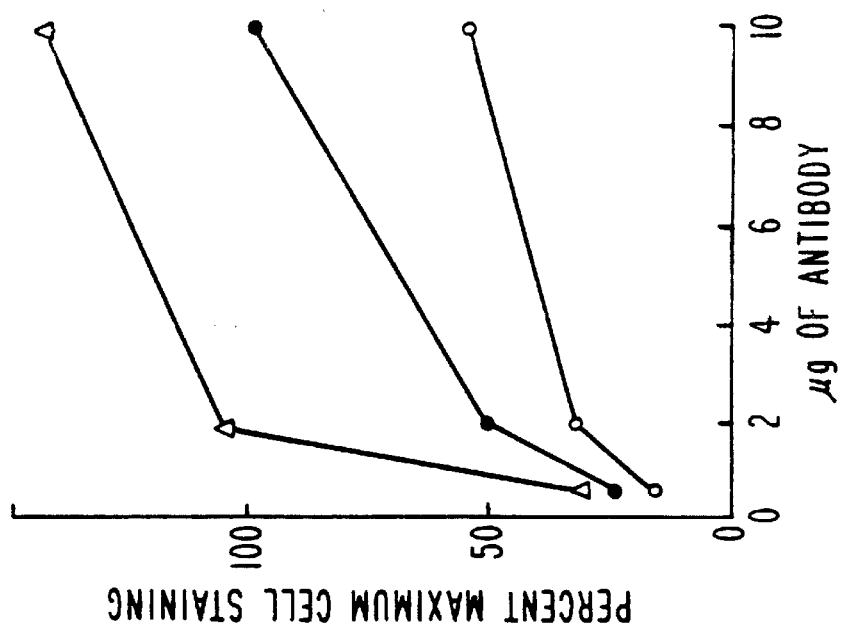

FIGS. 12A–C illustrate specific binding of immune serum to virus-coated plates; determined by radioimmunoassay as noted in the hereinafter described experimental procedures; CPM of immune serum binding to blank wells was subtracted from CPM binding to virus coated wells; to account for non-specific binding to virus coated wells, a similar value determined for normal mouse serum was subtracted form the value determined for immune serum; specific CPM bound is shown versus the dilution of mouse serum added in a final volume of 50 µl.; the mean ±SEM of duplicate wells from groups of 3 or 4 mice is shown at each dilution.

Figure 13B:
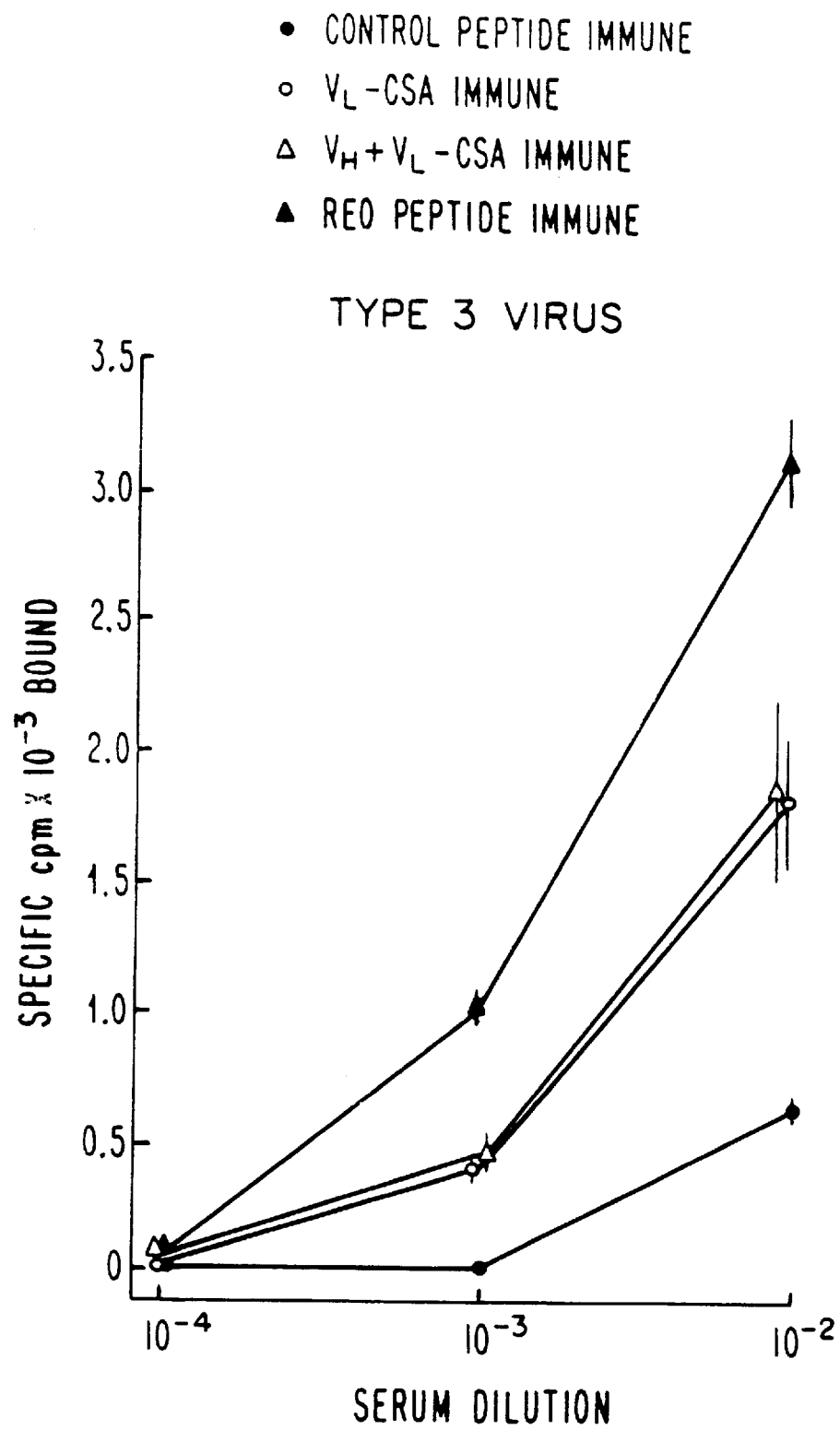

FIG. 13A and 13B illustrate immune serum assays for viral neutralization as described in the following section; serum was collected prior to immunization with peptides (pre-immune or day 0), on day 20 following the first immunization, and on day 60; the neutralization titer was determined at each time point from groups of 4 mice; the geometric mean divided by SEM of the reciprocal of the neutralization titer is shown at each time point.

Figure 14A:
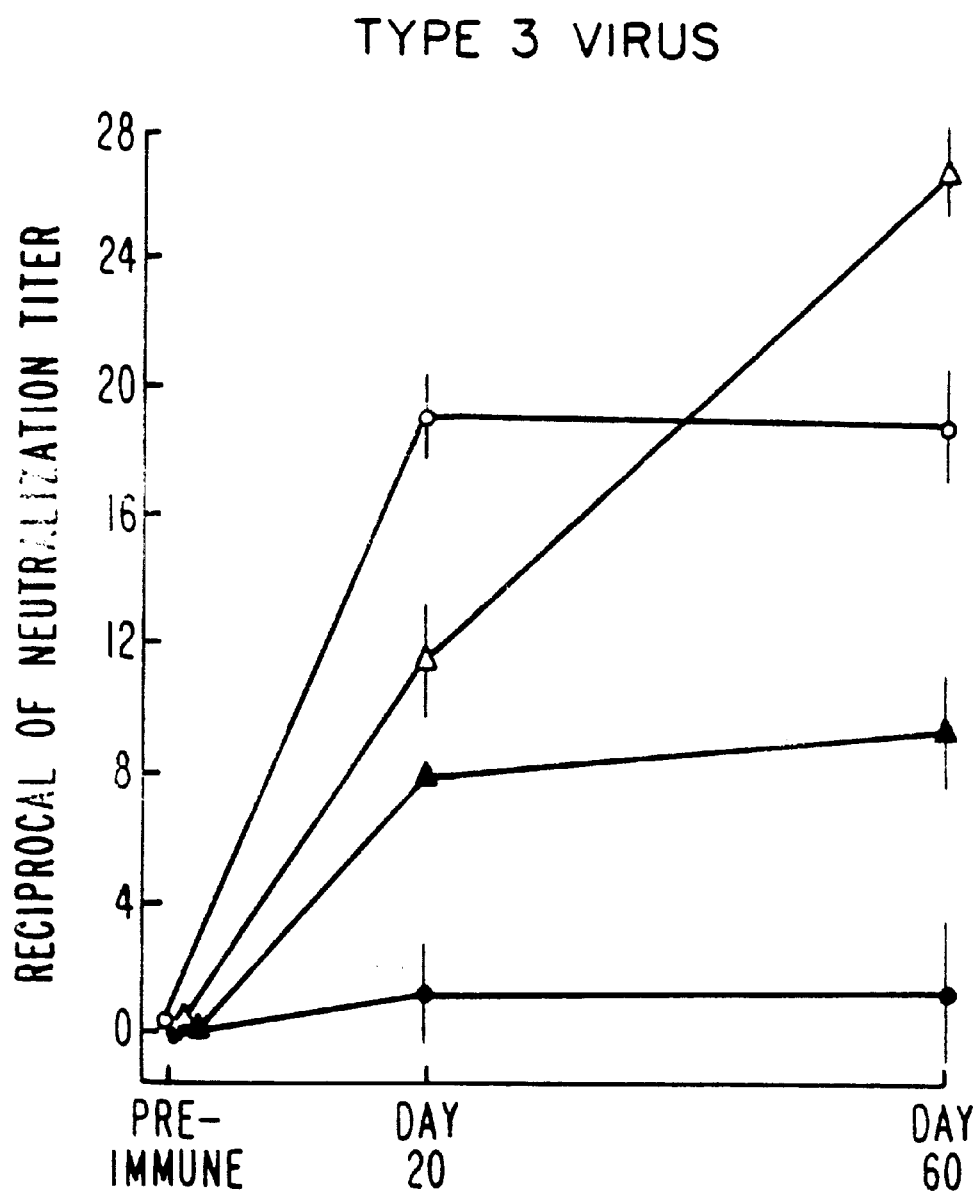

FIG. 14A and 14B illustrate plaque inhibition, determined as indicated in the following description; plaque numbers were determined for 4 mice in each group and the mean values determined; the highest dilution of serum that produced 50% or greater plaque inhibition was determined and is shown for each time point at which serum was obtained; plaque inhibition of both type 1 and type 3 virus is shown.

FIG. 15A and 15B shows the delayed type hypersensitivity (DTH) response of mice to intact reovirus type 3 after immunization with peptides.

FIG. 16 shows a representational diagram of two alternate routes for the development of biologically active peptides according to the methods of the invention.

Figure 17:
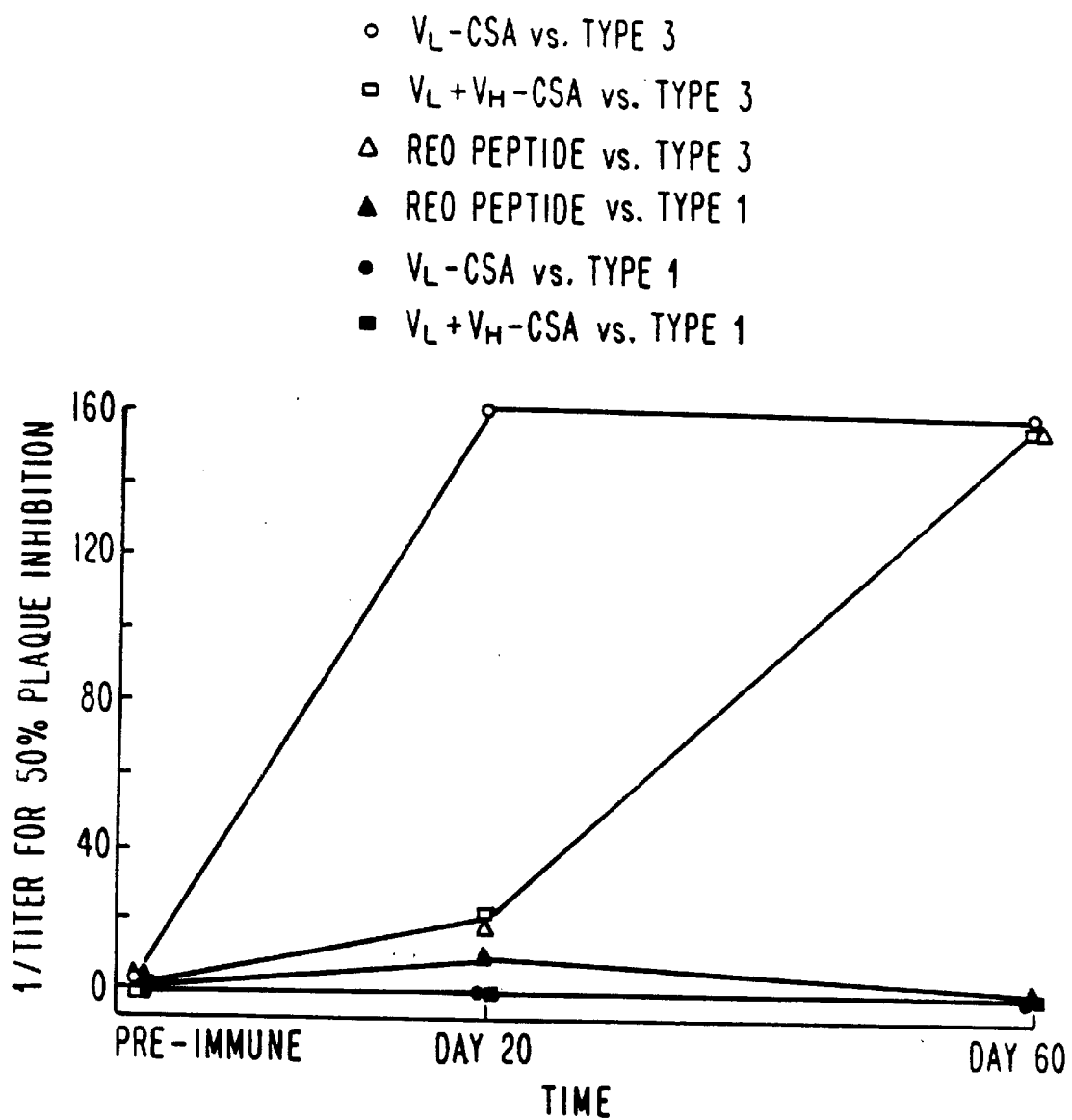

FIG. 17 illustrates data for mice immunized with the reovirus types noted by injection of $10^7$ PFU subcutaneously, or with the peptides noted at a dose of 100 µg split into two injections subcutaneously; one week later, mice were challenged with virus or peptides in the footpads; footpad swelling was determined as indicated in the following description 48 hours after challenge; the mean +SEM for groups of mice is shown.

Figure 18:
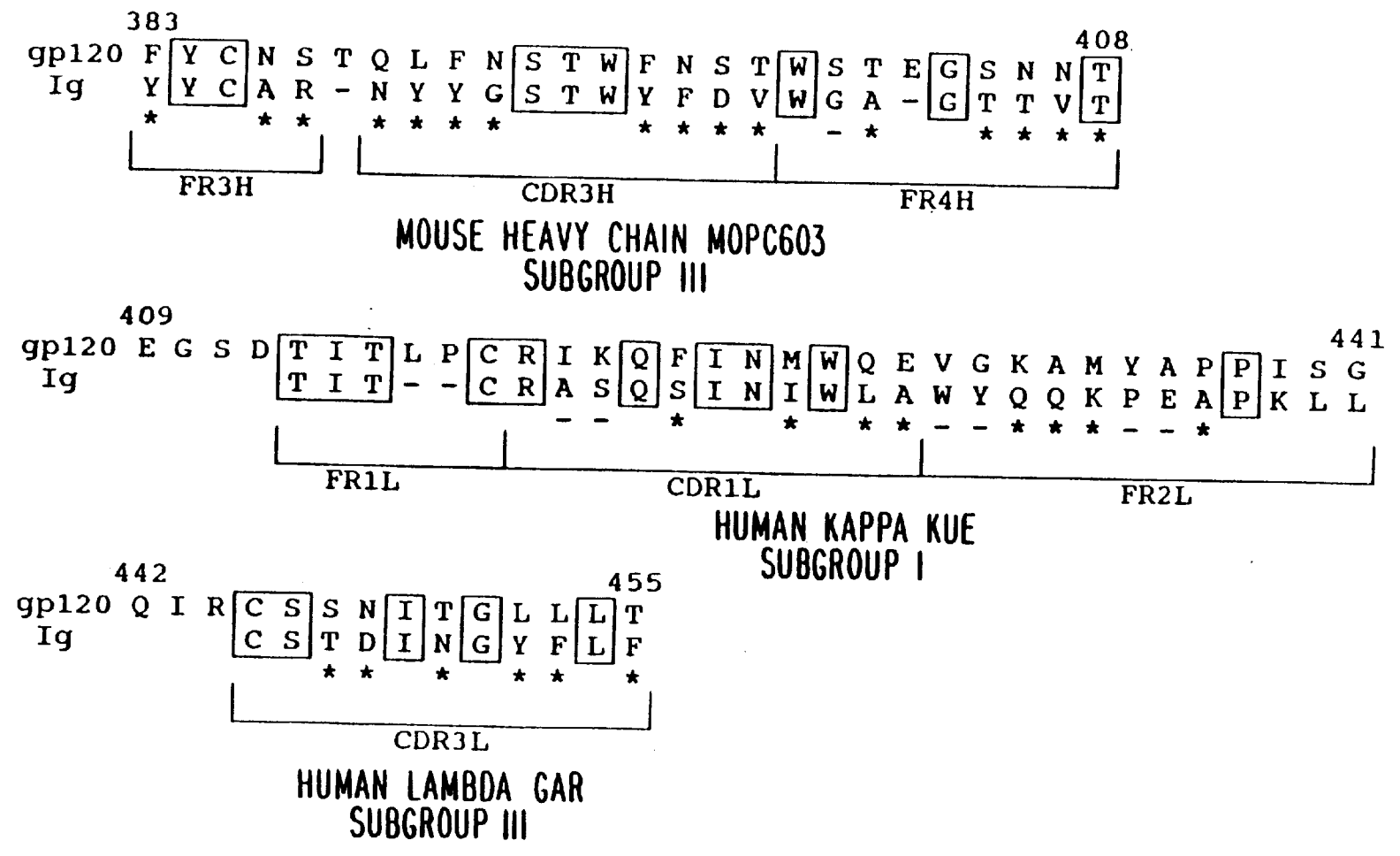

FIG. 18. Structural similarities in gp120 binding domain with Ig superfamily. Complementarity determining regions (CDR) and framework regions (FR) of the first, second, third and fourth domains of the respective heavy (H) or light (L) chains of several antibodies exhibited a degree of sequence homology with gp120 residues 383–455. The asterisks (*) mark residue positions of shared sequence homology between other HIV isolates and other antibodies. Crystallographic analysis of antibodies indicates that structural characteristics of CDR regions are preserved in spite of differences in sequence among antibodies. The dash (-) below a residue position denotes a lack of any sequence homology between an HIV isolated and an antibody. The dash (-) within a sequence denotes a deletion or insertion.

Figure 19:
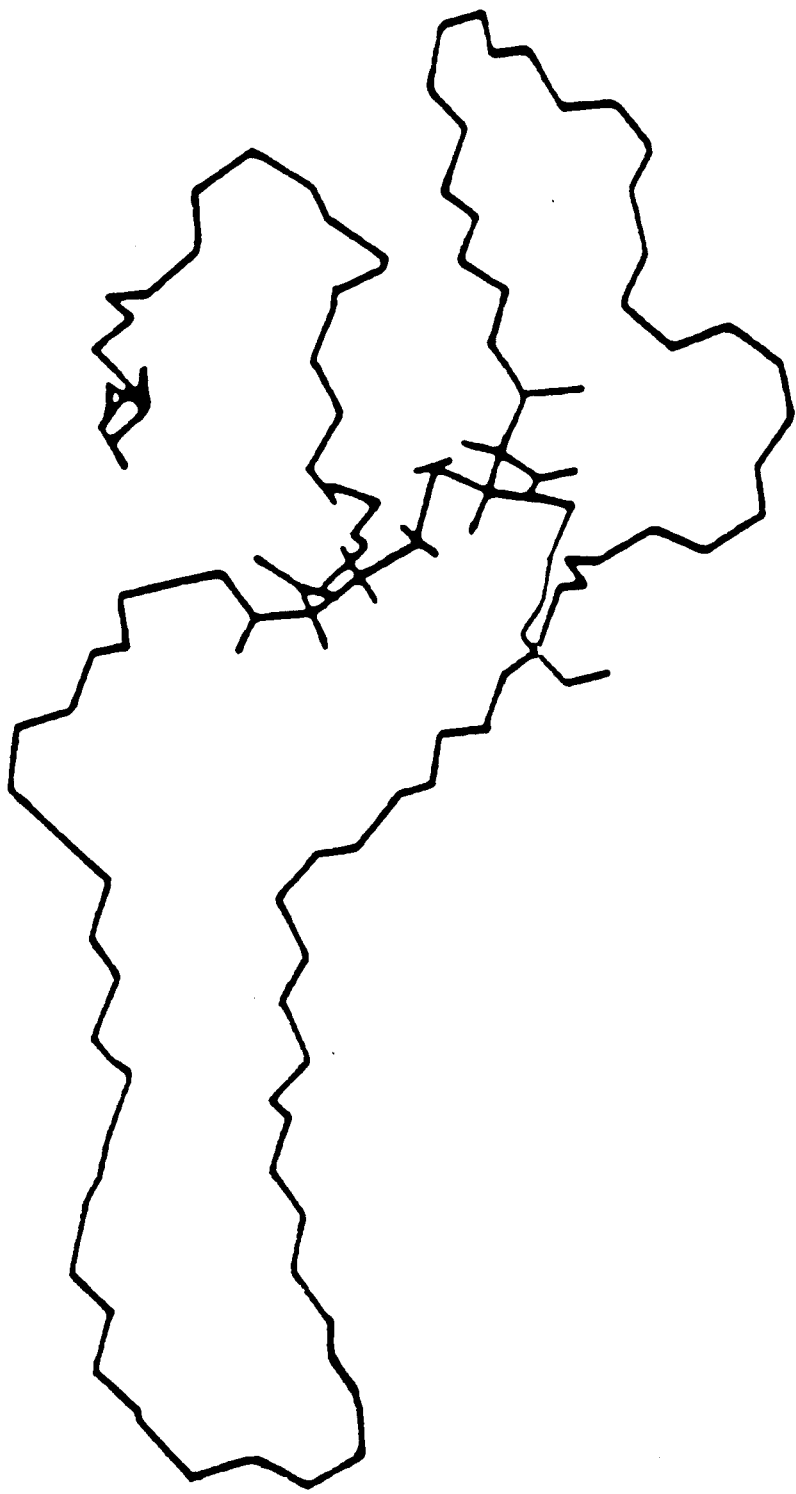

FIG. 19. Backbone representation of a proposed model for the putative binding side of gp120. The model extends from residue 413 through residue 456.

Figure 20:
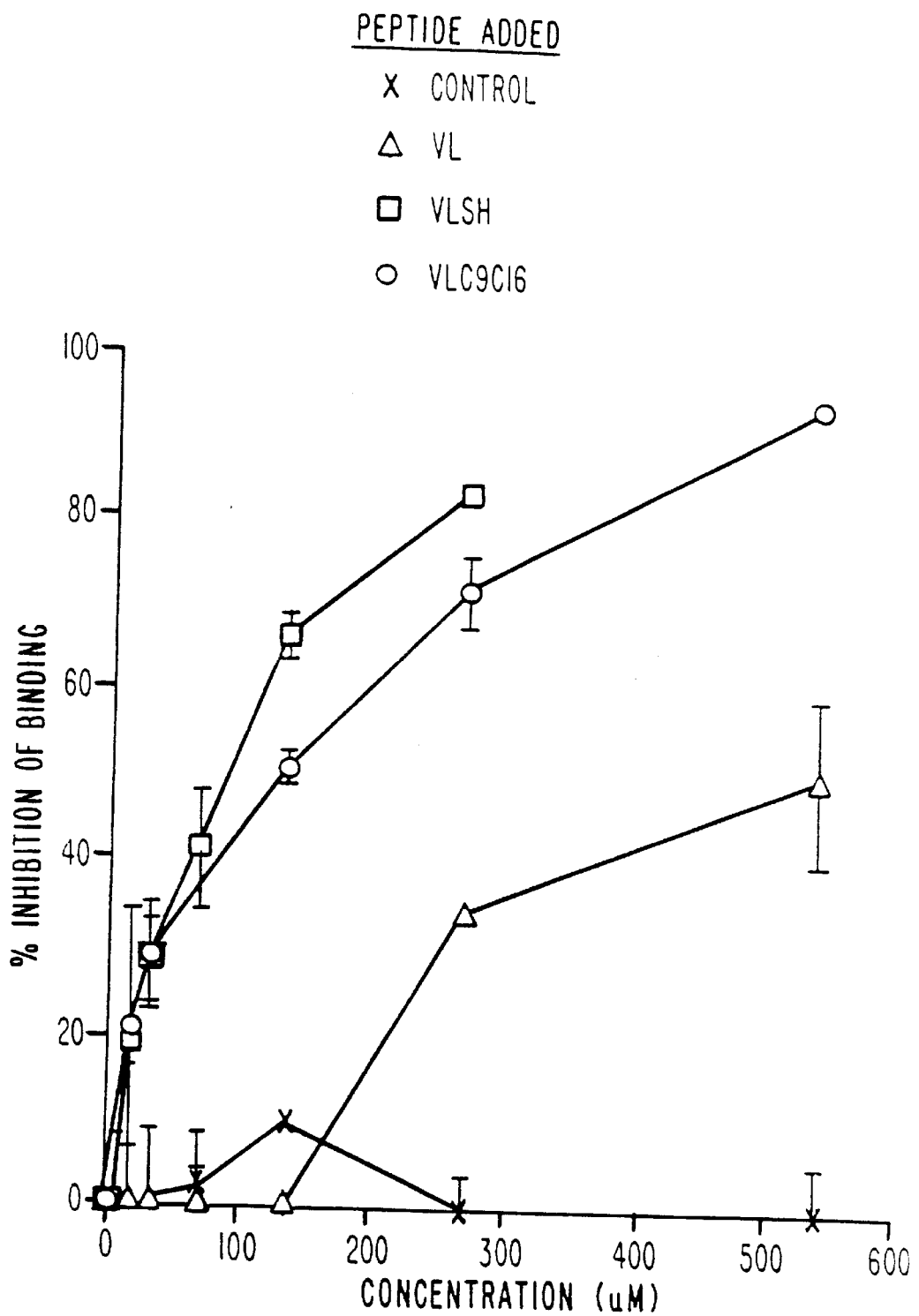

FIG. 20. Comparison of cyclic and linear peptide interactions with the Reo3R by inhibition of $^{125}$-reovirus type 3 binding.

Figure 21:
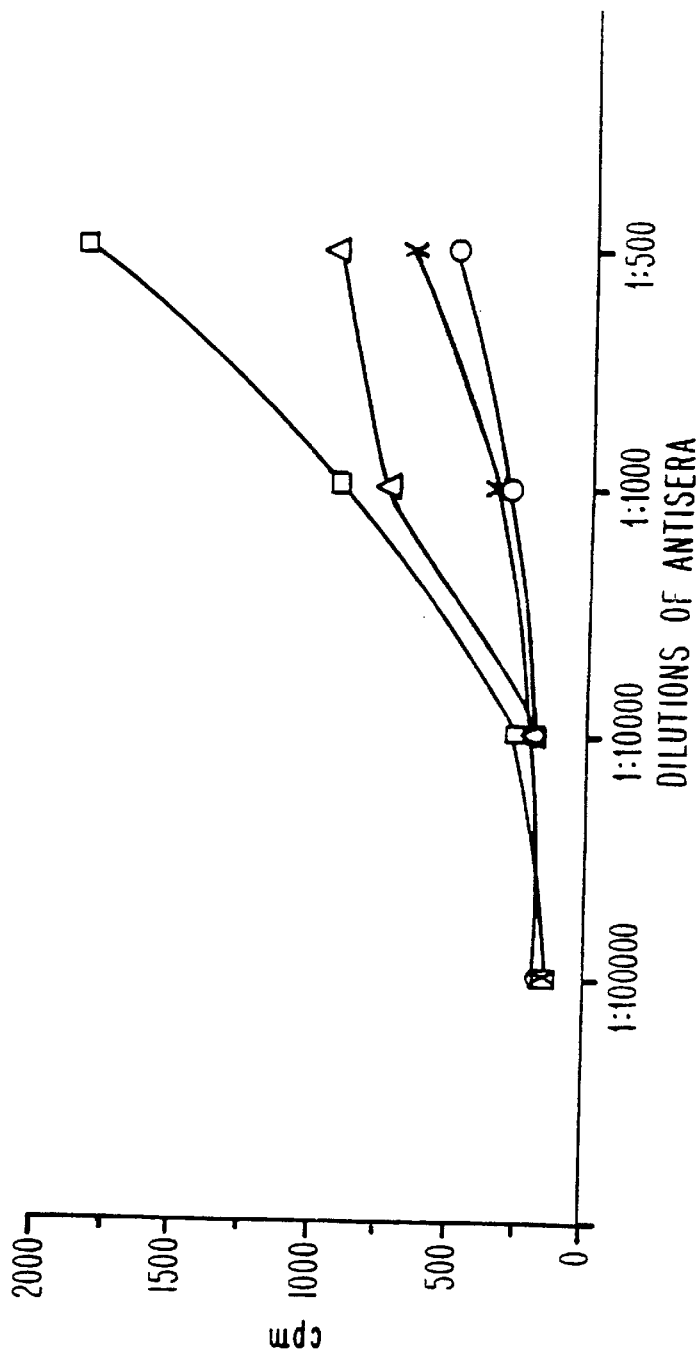

FIG. 21. Comparison of binding of antisera resulting from immunization of rabbits with B138, 466, 1005-45, or 1029-04 peptides to gp120.

Figure 22:
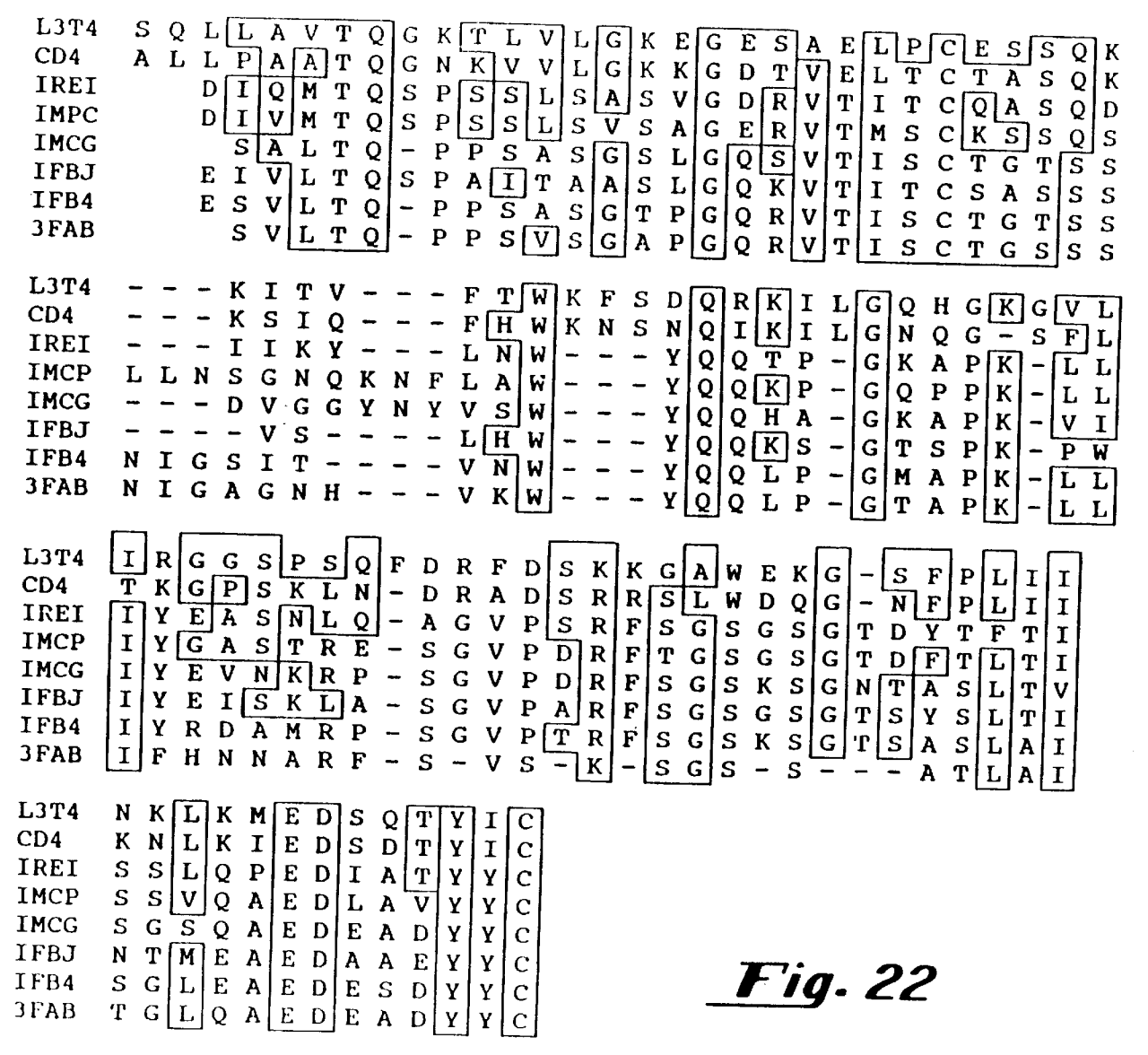

FIG. 22. Sequence homology of CD4 and L3T4 with Ig light chains of known three-dimensional structure. Boxed areas highlight similar sequences. Dashes (-) indicate insertions/deletions. Sequence alignment for comparative model building of CD4 utilizes a crystallographic template substituting the sequence of CD4 onto the homologous template. The choice of template is decided based upon the degree of sequence homology between a template and CD4 and the length of analogous turn/loop structures.

Figure 23:
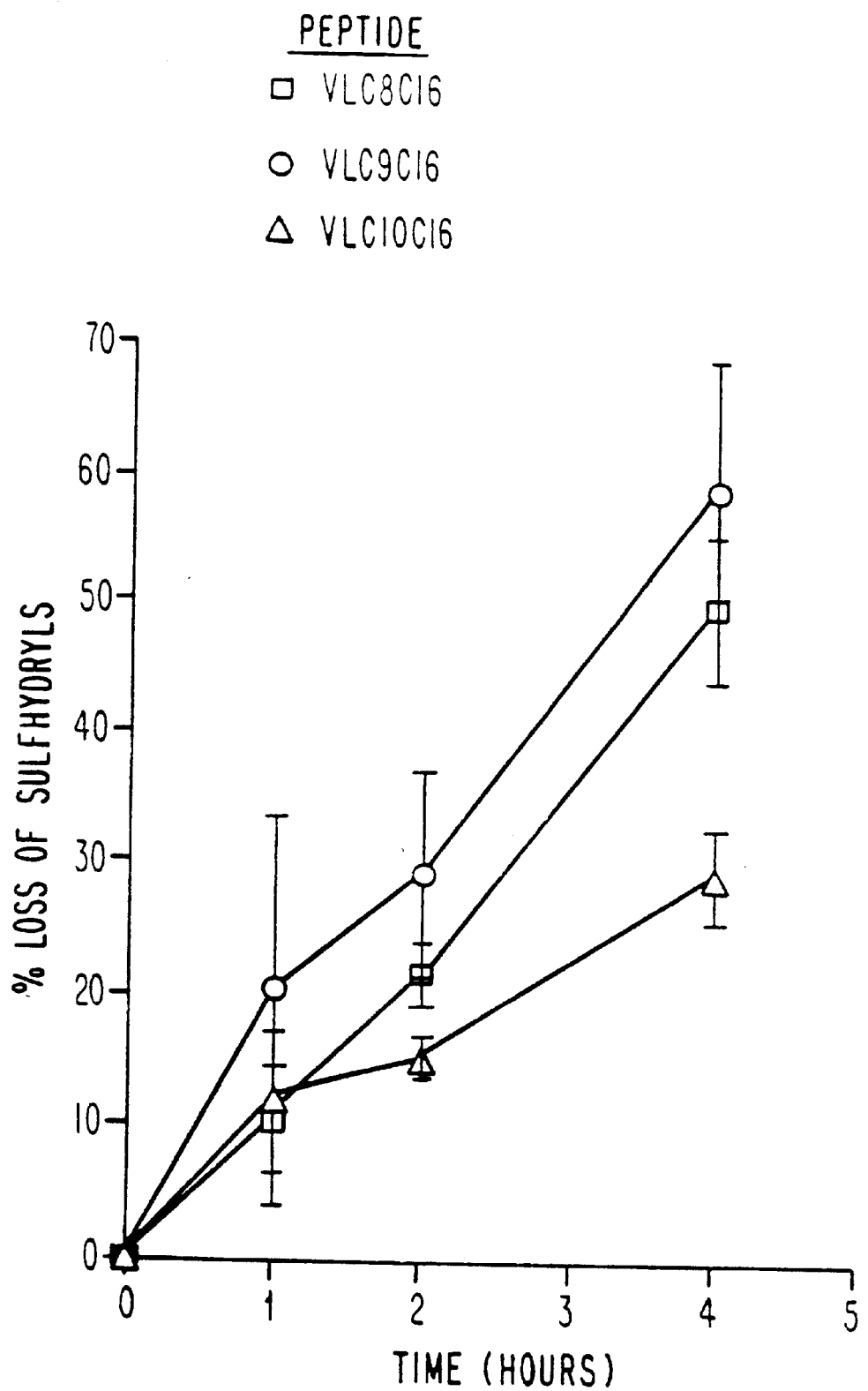

FIG. 23. Rate of loss of sulfhydryls for various peptides.

Figure 24:
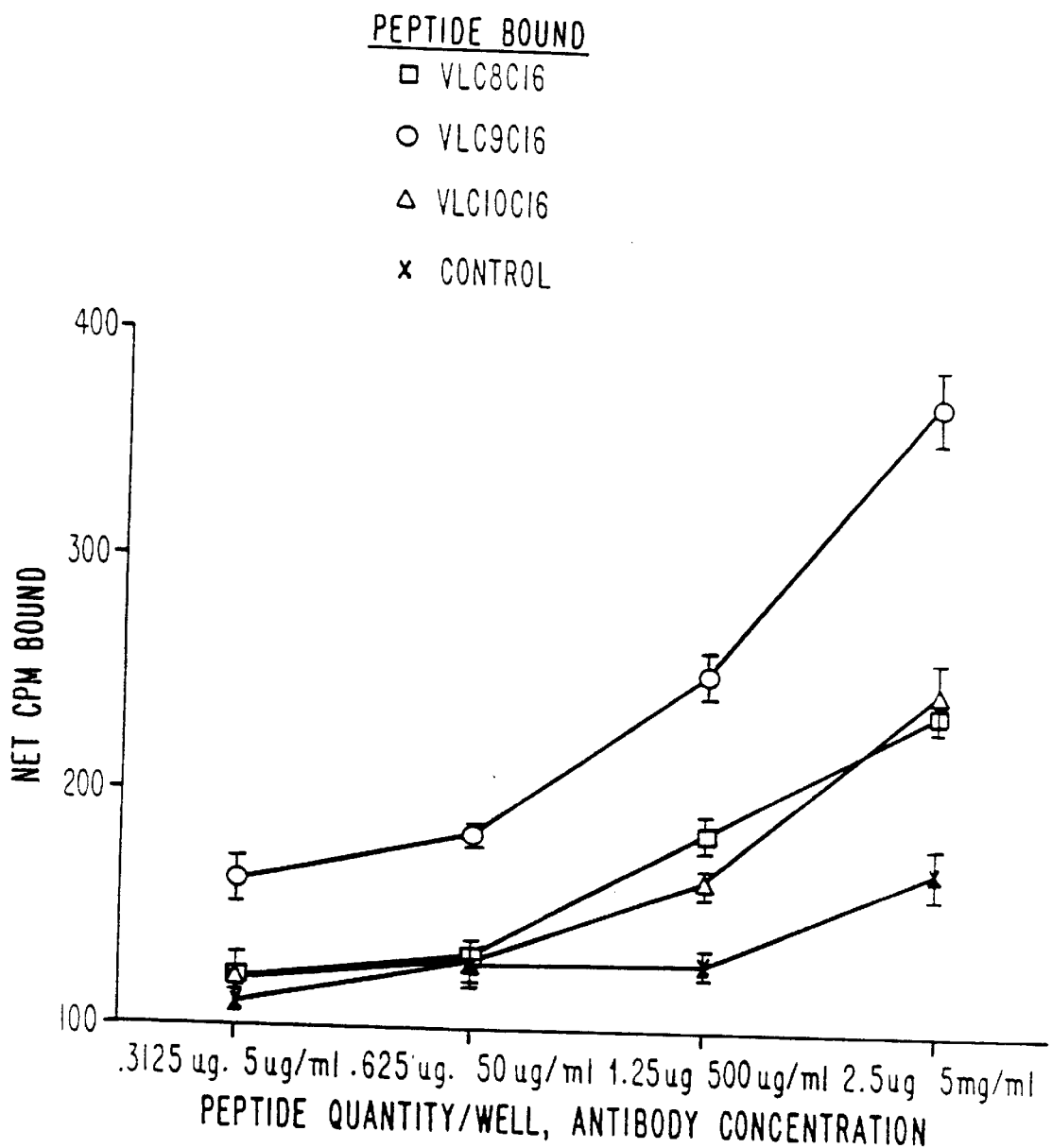

FIG. 24. Binding of 9B.G5 to peptides on solid phase RIA.

Figure 25:
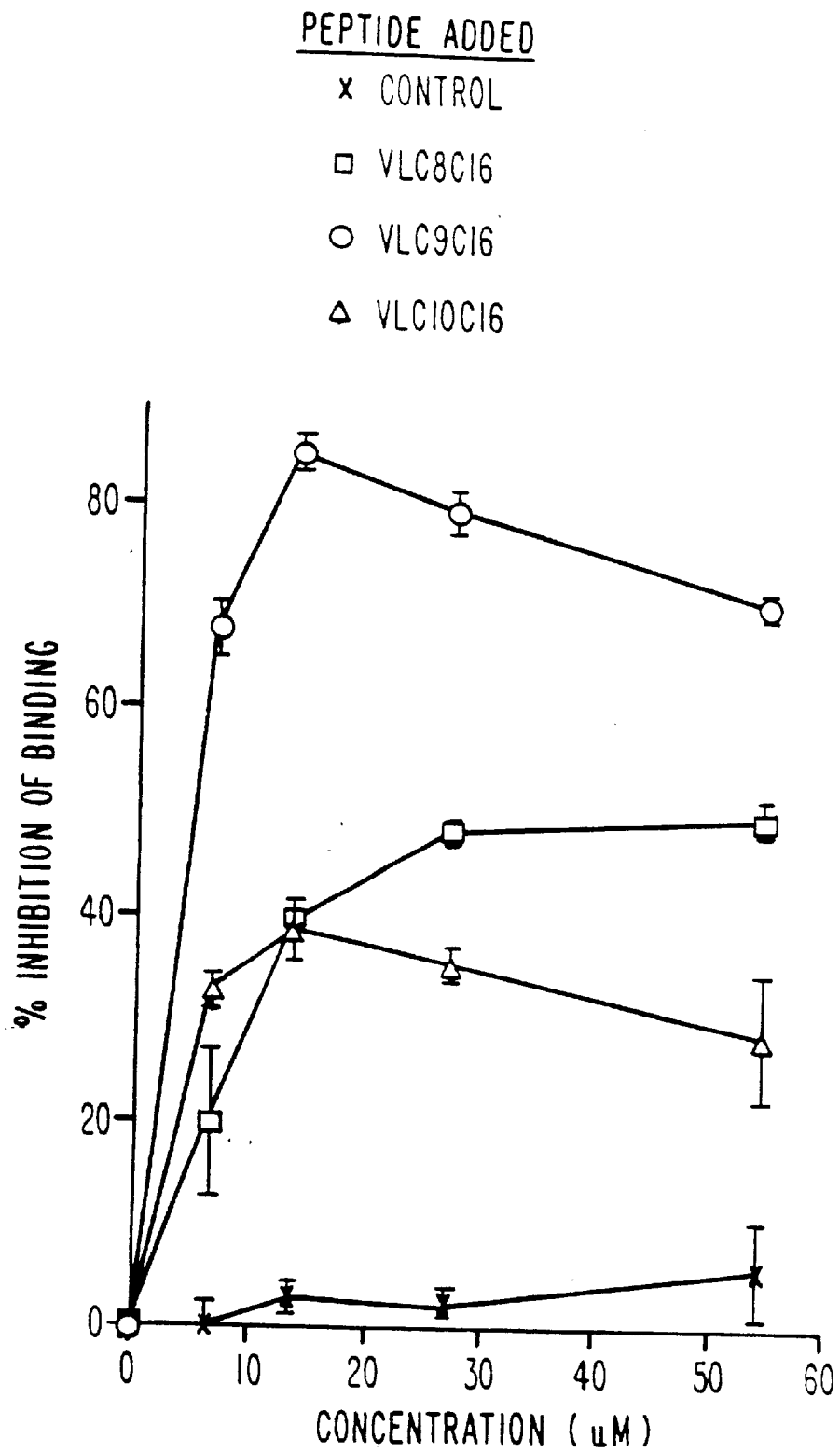

FIG. 25. Inhibition of 9B.G5 - 87.92.6 interaction by cyclic peptides.

Figure 26:
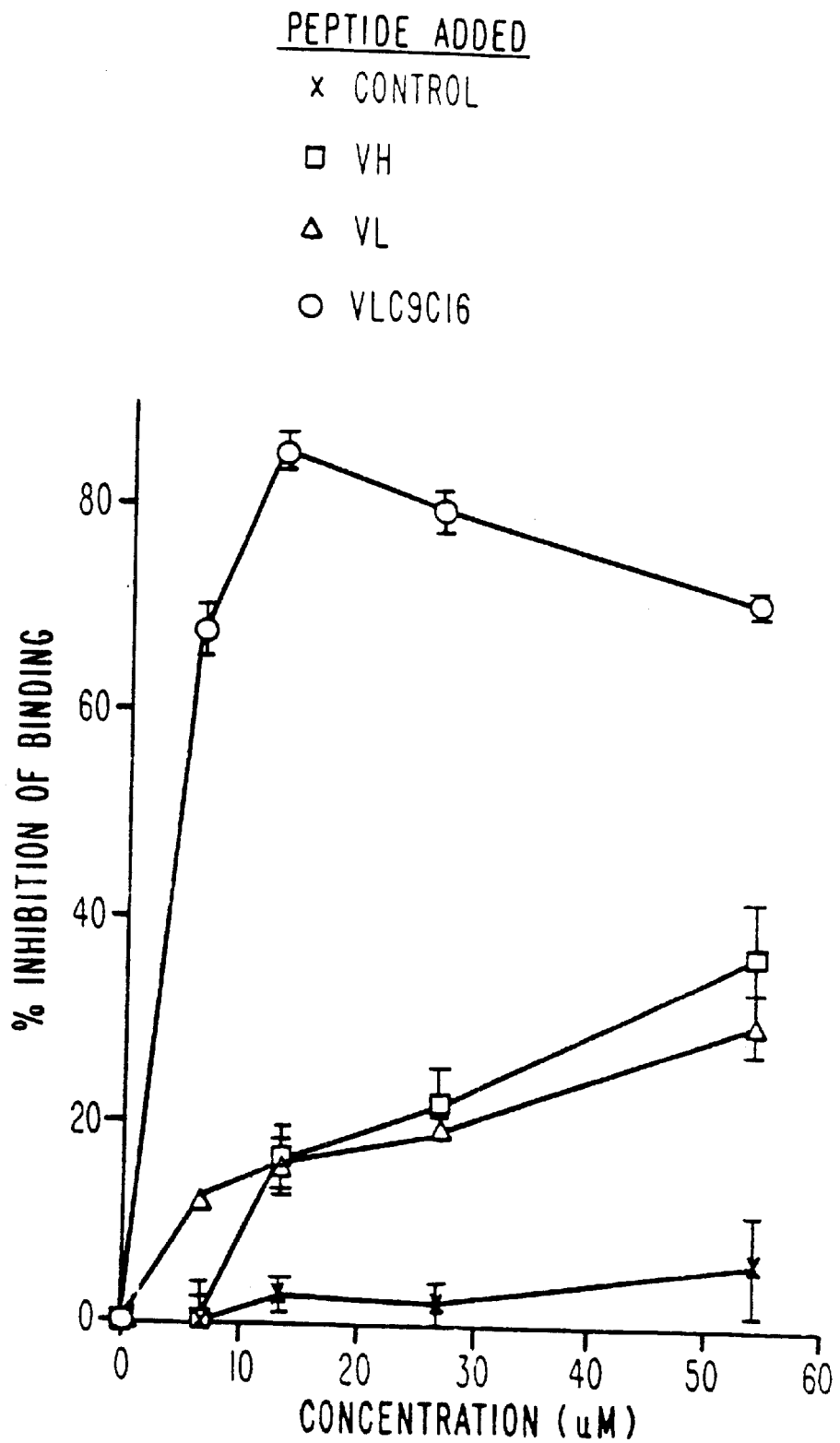

FIG. 26. Inhibition of 9B.G5 - 87.92.6 interaction by cyclic peptides. Comparison with linear peptides derived from the 87.92.6 variable regions.

Figure 27:
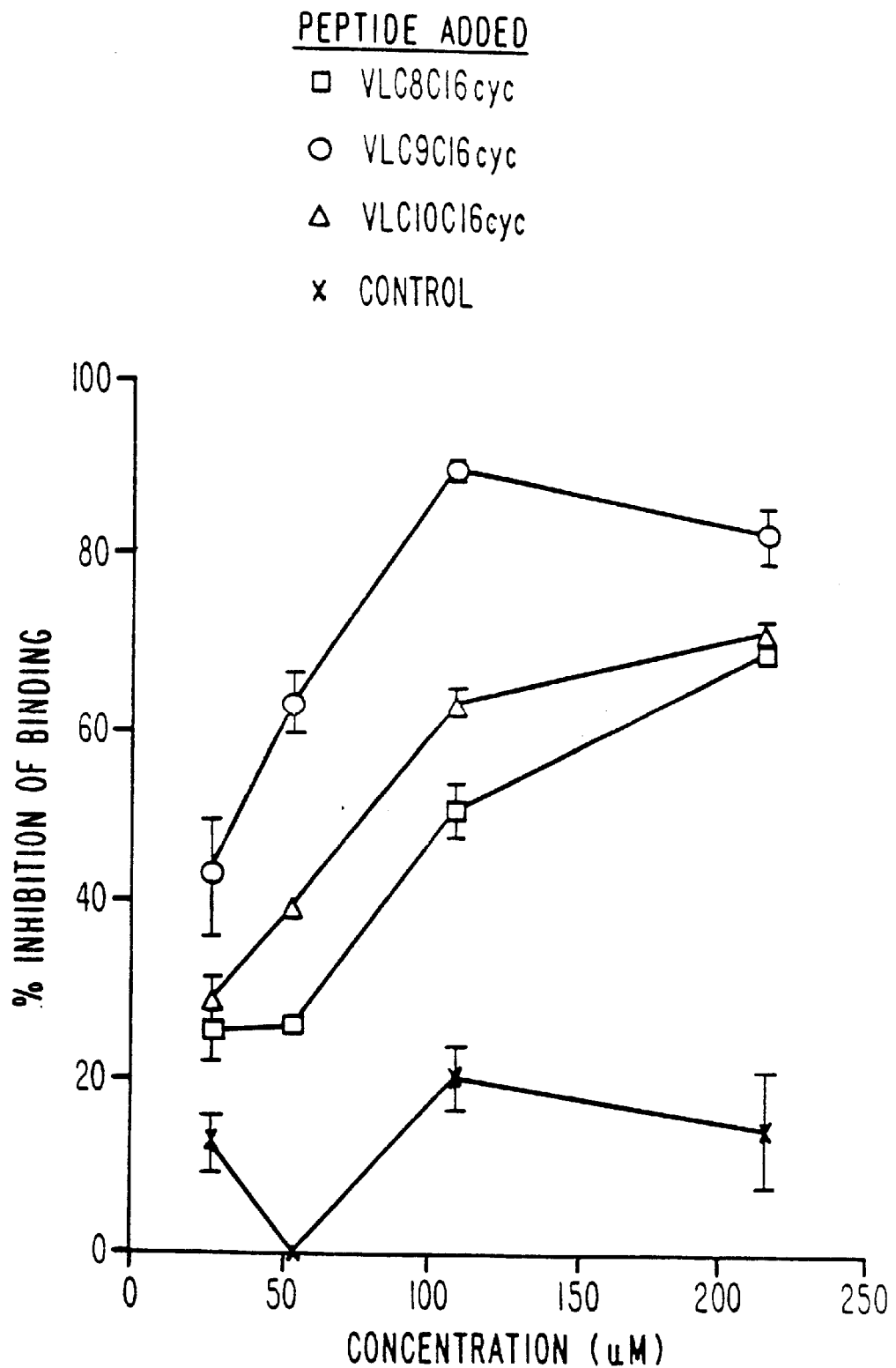

FIG. 27. Inhibition of 9B.G5 - reovirus type 3 interaction by cyclic peptides.

Figure 28:
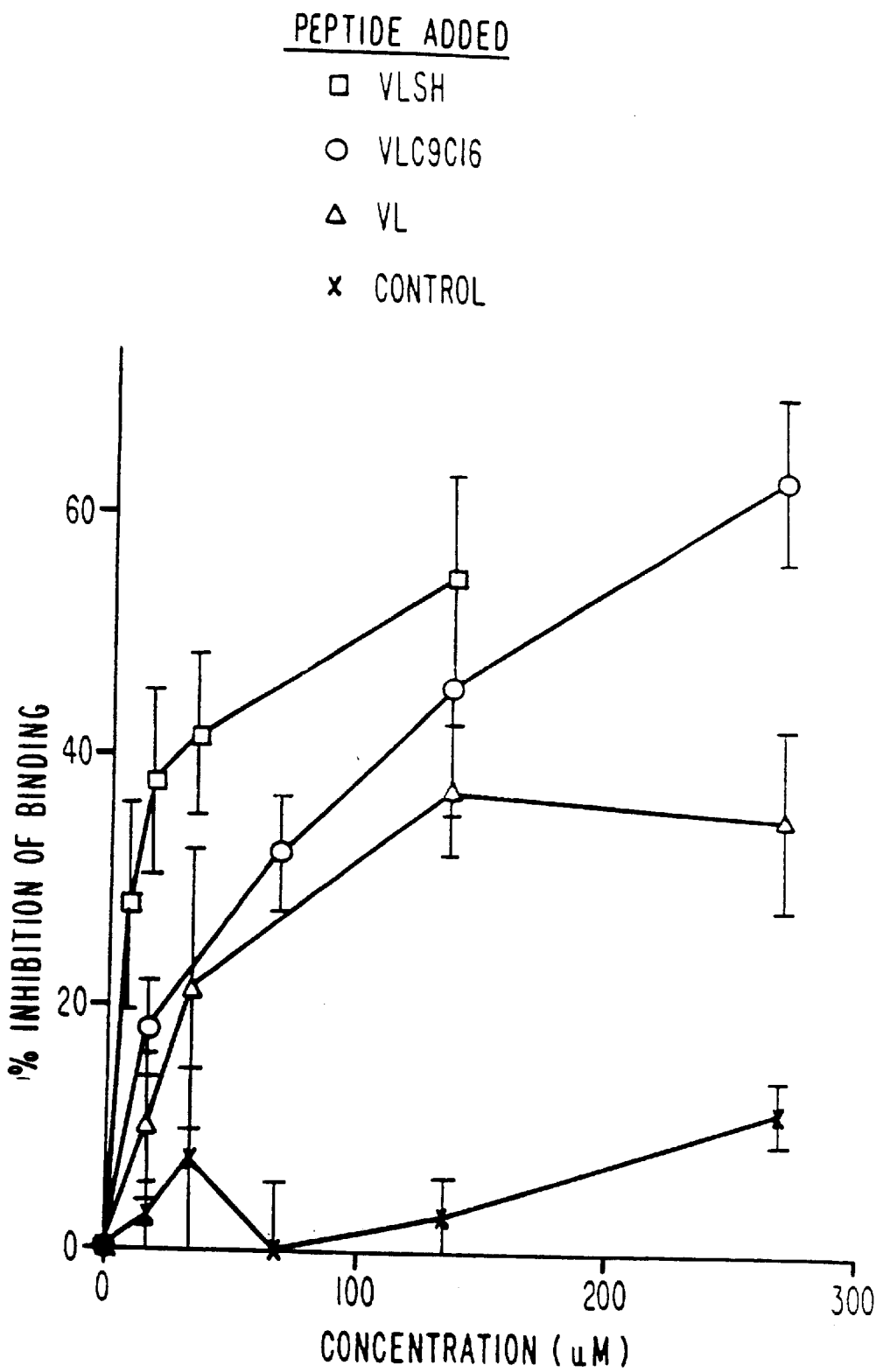

FIG. 28. Inhibition of 9B.G5 - reovirus type 3 interaction by cyclic peptides. Comparison with linear and dimeric peptides derived from the 87.92.6 variable regions.

Figure 29:
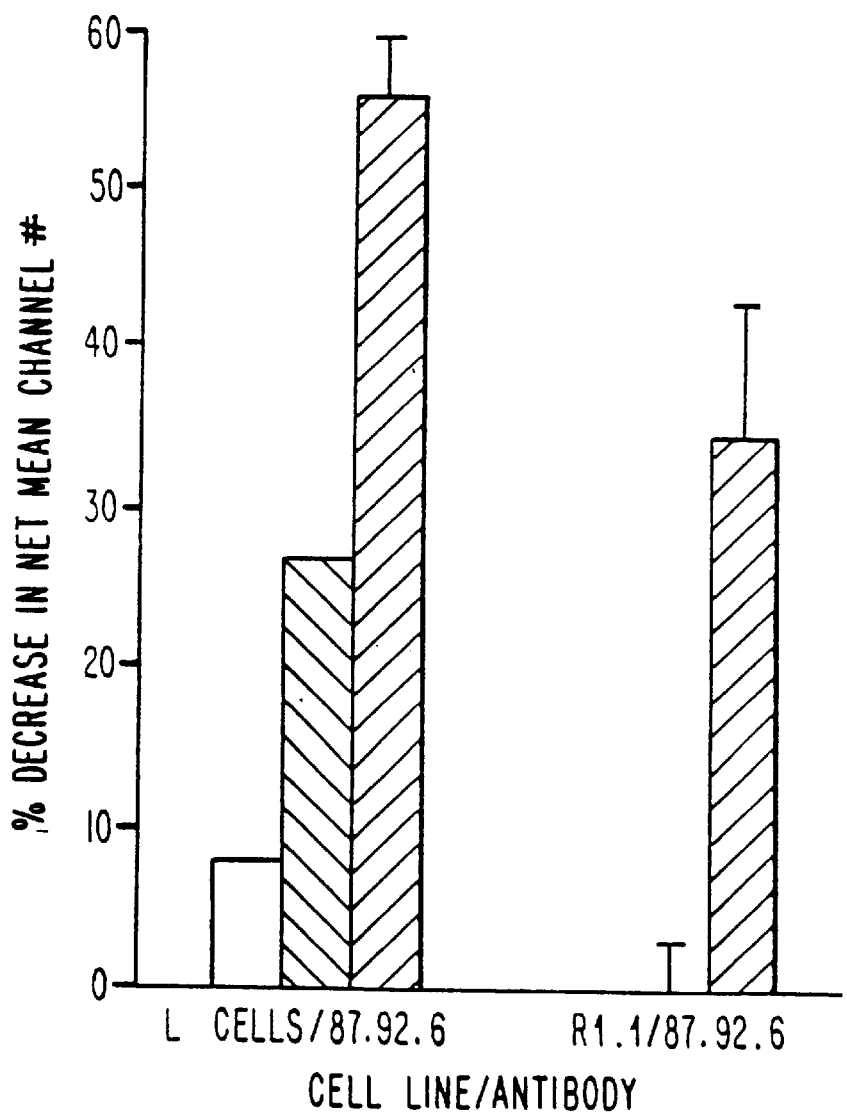

FIG. 29. Inhibition of 87.92.6-Reo3R interaction by peptides.

Figure 30:
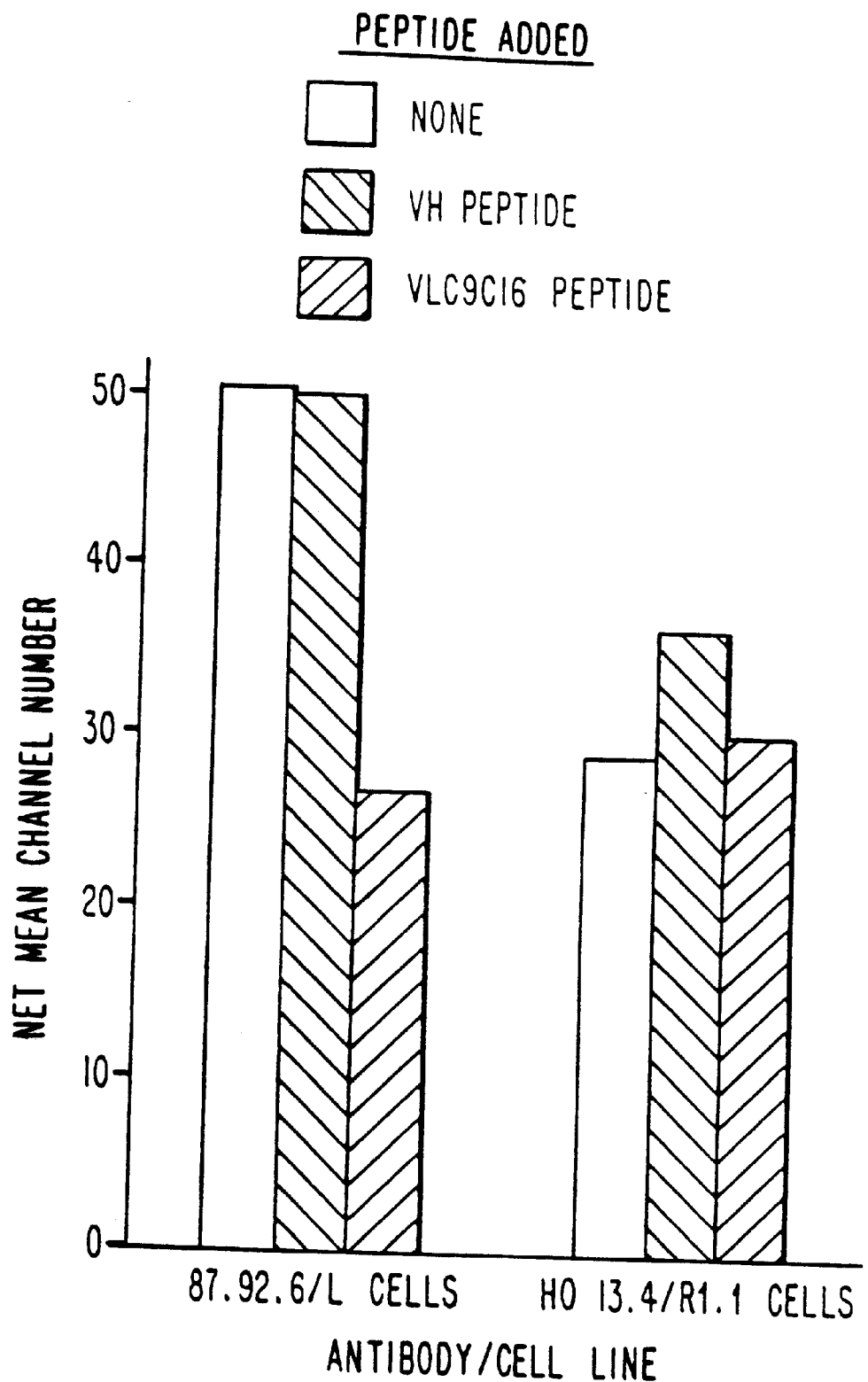

FIG. 30. Specificity of $V_L C_9 C_{16}$ peptide binding to the Reo3R.

Figure 31:
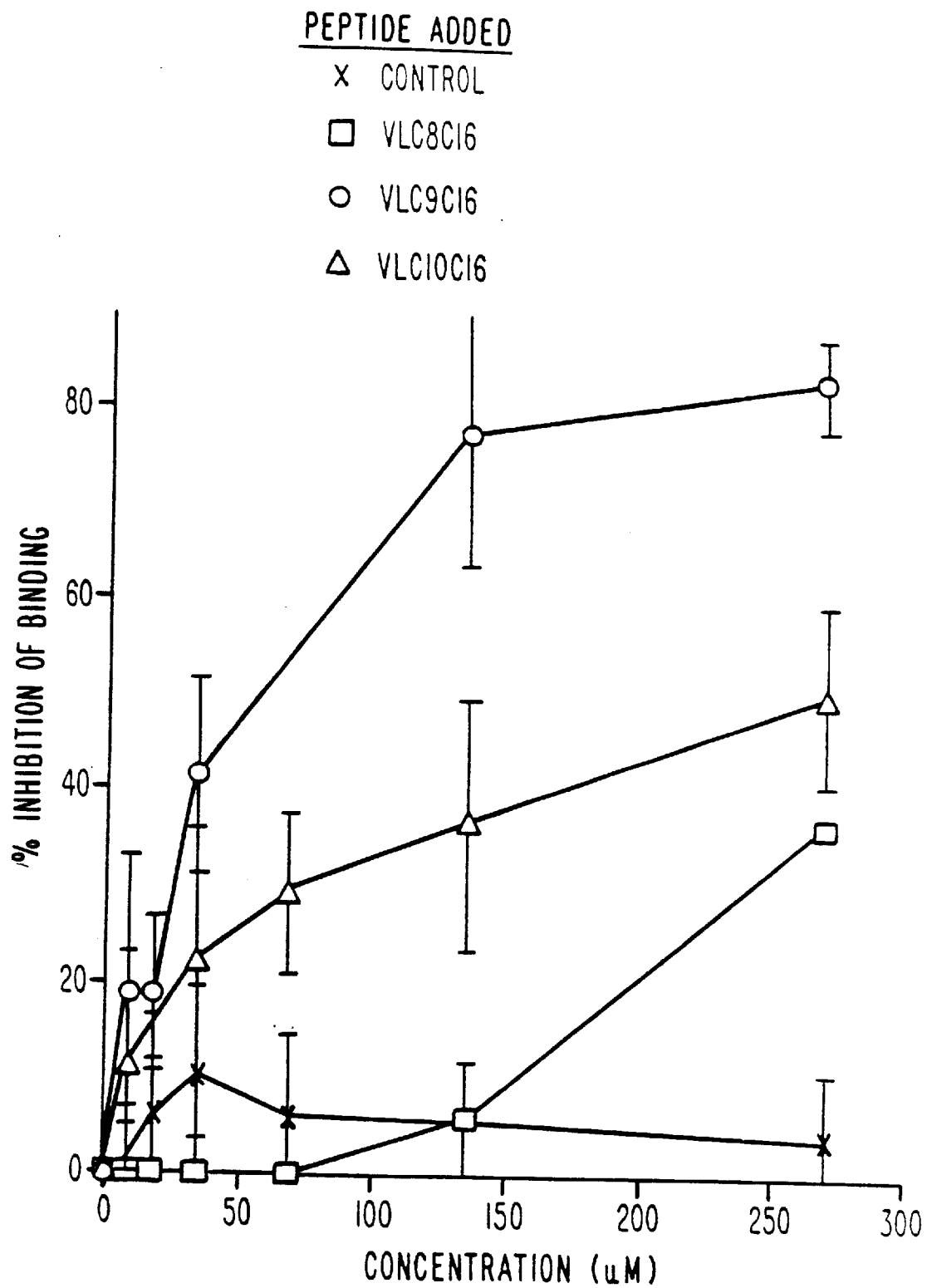

FIG. 31. Inhibition of reovirus type 3 - Reo3R interaction by peptides.

DETAILED DESCRIPTION OF THE PREFERRED EMBODIMENTS

According to the invention, specific and discrete portions of proteins involved in protein-protein interactions can be identified and biologically active peptides can be constructed based upon the amino acid sequences identified. The amino acid sequences of specific portions of anti-idiotypic antibodies correspond to the amino acid sequence of the specific portion of the epitope of an antigen that binds to an idiotypic antibody. Likewise, the amino acid sequences of specific portions of anti-receptor antibodies correspond to the amino acid sequences of the specific portion of a ligand which interacts with the receptor. Thus, the amino acid sequence of either the critical portion of an epitope or the biologically active portion of a biologically active protein can be identified.

The attachment of proteins to one another often involves secondary structural features such as loops or helices. The disposition of specific kinds of residues (aromatic and hydrophilic) allows attachment to occur through interactions between the residues of the different proteins. These interactions include vander Waals interactions and hydrogen bonds. The individual loops that occur in portions of antibodies, for example, form hydrogen bonds with antigen fragments. Likewise, individual loops that occur in portions of receptor molecules form hydrogen bonds with receptor binding proteins.

An idiotype is the set of idiotopes which are antigenic determinants. The idiotopes occur in the CDR portion of the variable region of a particular antibody. Antigens represented by an idiotype have specific interactions with the antibody which results in bind. Such idiotypes are called internal images of antigens. An anti-idiotypic antibody is an antibody is specific for the portion of another antibody that represents the idiotope regions. The idiotype or internal image of an anti-idiotypic antibody is similar to the antigen that the idiotypic antibody recognizes.

Thus, peptides modelled from the surface of a highly variable CDR loop are used to mimic a region (loop or loop portion of an alpha helix) of some other protein. In some cases, more than one surface can be linked, forming dimers. In other cases, the loops are constrained with specifically placed cysteine residues or by placement of other residues which permit loop closure such as through, for example, ionic bonds.

As used herein, the term "biologically active protein" refers to proteins which bind to cellular receptors and thereby alter or affect the function or behavior of the cells, or prevent or alter the effect which another biologically active protein would otherwise have upon those cells. A pathogen antigen can be a biologically active protein if, upon binding to a host cell, it alters or affects the function or activity of a cell or prevents another agent from doing so. Other examples of biologically active proteins include, but are not limited to, cytokines, hormones and growth factors.

As used herein, the term "neutralizing epitope" refers to the portion of a pathogen antigen against which antibodies have a neutralizing activity. That is, antibodies specific for a neutralizing epitope will render the pathogen non-infective and/or inactive.

As used herein, the term "neutralizing antibodies" refers to antibodies which recognize a pathogen and render it non-infective and/or inactive.

As used herein, the term "anti-pathogen antibodies" refers to antibodies which recognize and bind to a pathogen, specifically a pathogen antigen.

As used herein, the term "anti-receptor antibodies" refers to antibodies which recognize and bind to a receptor, specifically at a receptor site. Anti-receptor antibodies are specific forms of anti-idiotypic antibodies. Anti-receptor antibodies are anti-idiotypic antibodies which are specific for the idiotype of an immunoglobulin molecule. That is, they are specific for the portion of the immunoglobulin receptor which interacts with a biologically active protein.

As used herein, the term "receptor site" refers to the portion of the receptor that interacts with a protein that binds to the receptor.

As used herein, the term "biologically active peptides" refers to proteinaceous molecules which mimic biologically active proteins or prevent the interaction between biologically active proteins and receptors.

Biologically active peptides can be constructed which function as the epitope or mimic a biologically active protein. Alternatively, biologically active peptides can be constructed which interact with receptors and thereby block the binding of a pathogen antigen or biologically active protein to a receptor.

As used herein, the term "biologically active compound" refers to a compound which mimics a biologically active protein or which can otherwise interact with a receptor and thereby block the binding of a pathogen antigen or biologically active protein to a receptor. Additionally, a biologically active compound can mimic an epitope of an antigen of a pathogen and elicit a neutralizing immune response in a mammal. A biologically active compound may be a peptide or a non-peptidyl compound including, but not limited to, compounds which comprise amino acid sequences linked by non-peptide bonds. The term "compounds" as used herein refers to peptides and non-peptidyl compounds.

One having ordinary skill in the art can appreciate that biologically active compounds can be synthesized which comprise amino acid sequences found in peptides but which are linked by non-peptide bonds. One having ordinary skill in the art can readily appreciate that the essential step of identifying the biologically significant portion of an antigen or ligand allows for the construction of compounds, peptide and non-peptide, which mimic the function or activity of the antigen or ligand.

Accordingly, the methods of the invention also relate to constructing and using biologically active compounds that are modelled based upon corresponding amino acid sequences of antigen or ligands and anti-idiotypic or anti-receptor antibodies. The identification of corresponding sequences in portions of anti-idiotypic antibodies or anti-receptor antibodies and pathogen antigens or biologically active proteins can be used in the construction of biologically active compounds which comprise such shared amino acid sequences but which are linked by non-peptide bonds. Furthermore, using well known techniques, such non-peptide biologically active compounds can be synthesized from readily available starting materials be those having ordinary skill in the art.

As used herein, the terms "correspond" and "corresponding" refer to the level of shared identity between two amino acid sequences. That is, the amount of identical and conservatively substituted amino acid sequences shared between two molecules. As used herein, two sequences correspond if, when compared, they share approximately at least 80% identical and conservatively substituted sequences of which at least about 28% are identical sequences and between about 30–42% conservative substitutions. Generally, corresponding amino acid sequences share at least six similar amino acid residues. Corresponding sequences are often longer, comprising about 10 or more corresponding residues. As used herein, these terms refer to the quantifiable similarity between amino acid sequences. One having ordinary skill in the art can compare amino acid sequences and calculate whether or not they correspond to each other. The terms "homologous", "homology", and "sequence similarity" are often used interchangably by those having ordinary skill in the art to refer to corresponding amino acid sequences.

One having ordinary skill in the art can determine that an amino acid sequence corresponds to another amino acid sequences. The level of skill of those having ordinary skill in the art provides that amino acid sequences can be compared and sequence "similarity", "homology", and "correspondence" can be determined routinely. The processes of comparing and determining sequences correspondence are well known and widely reported. See, for example, Bruck, C. et al., 1986 Proc. Natl. Acad. Sci. USA, 83:6578–6582, which is incorporated herein by reference. One having ordinary skill in the art can construct a peptide having an amino acid sequence which corresponds to another amino acid sequence. Corresponding amino acid sequences can be determined and peptides can be constructed using other amino acid sequences as models. The amino acid sequence of such a peptide can be identical to that sequence from which it was modelled. Peptides can be constructed that comprise amino acid sequences modelled after two corresponding sequences. An amino acid sequence can be determined which corresponds to both model sequences.

When the anti-idiotypic antibody is specific for an anti-receptor antibody, the specific portion of the receptor involved in ligand/receptor interaction or pathogen/receptor interaction can be identified. Peptides can be constructed which bind to the ligand or pathogen at the specific portion normally involved in receptor binding, thereby preventing receptor binding.

Harlow, E. and D. Lane, ANTIBODIES: A Laboratory Manual, Cold Spring Harbor Laboratory, Cold Spring Harbor NY 1988, which is incorporated herein by reference, provide a review of the molecular and genetic aspects of mammalian immunology generally, and antibodies in particular. This publication contains a review of antibody structure and function including variable regions and the CDRs thereof.

Antibodies bind to antigens by virtue of their secondary structure. Antibodies contains amino acid sequences within the CDR of the variable region that form loops or reverse turns. The CDRs represent determinants termed idiotypes. CDRs are quite variable in sequence. However, their shapes are limited. Therefore, the number of conformations of the CDRs are limited. The peculiar shape or conformation of the CDRs is determined by a few amino acid residues. Therefore, one can imagine antibodies of a certain specificity as having a conserved beta sheet framework and loop projections which are generally comparable. The individual amino acid residues on each loop might be different when one compares one antibody to another. The consequence is that a particular loops which bind antigens may vary in sequence from one antibody to another but will often resemble each other in three dimensional structure. Since amino acid sequences of antibodies in their CDRs are hypervariable, they themselves can resemble foreign antigens which have similar loops containing similar amino acids. Accordingly, the means by which antibodies bind other proteins can be applied to construct immunogens or mimetics of immunogens or biologically active proteins.

It is well known to those having ordinary skill in the art that the light and heavy chains of antibodies contain variable regions and, within these regions, three loop portions known as CDRs which are hypervariable. The CDRs are the portions of the antibodies where binding to epitopes takes place. That is, CDRs of an antibody comprise amino acid sequences which form a three dimensional structure that directly interacts with the three dimensional structure formed by specific amino acid sequences of the antigen to which the antibodies bind. A specific portion of the CDR loop interacts with a specific portion of an antigen molecule. Methods of determining the amino acid sequence of the variable regions of antibodies are well known to those having ordinary skill in the art.

According to the invention, identification of the amino acid sequence of the portion of antibody that reacts to a specific portion of the target protein can be used to construct biologically active compounds. It has been discovered that anti-idiotypic antibodies contain regions of peptide sequences which correspond to the peptide sequences of the epitope for which the anti-pathogen antibody binds. It has been discovered that anti-receptor antibodies contain regions of peptide sequences which correspond to the peptide sequences of pathogen antigens or natural biologically active proteins which bind to such receptors.

Amino acid sequences of anti-idiotypic antibodies and anti-receptor antibodies which correspond to and which mimic epitopes and biologically active portions of biologically active proteins, respectively, it has been discovered that such corresponding sequences occur in the variable regions of the antibodies. The corresponding regions usually occur within the CDRs, often within the CDR II, that is the designated second CDR. In particular, the corresponding sequences usually occur within one or two of the CDR of the light chain and/or heavy chain. In the case of anti-idiotypic antibodies, it has been discovered that portions of those antibodies which specifically interact with antibodies against an antigen correspond to portions of the antigen. Similarly, in the case of anti-receptor antibodies, it has been discovered that they correspond to, that is, they share sequence similarity with, portions of pathogen antigens associated with pathogen attachment to cellular receptors and with portions of biologically active proteins that interact with receptors.

This technology is particularly useful to identify amino acid sequences for the following purposes.

1. To construct immunogenic compounds which mimic pathogen antigen neutralizing epitopes and are thereby useful to elicit neutralizing antibodies against pathogens, such compounds are useful as vaccine components.

2. To construct biologically active compounds which block the binding of pathogens to receptors on host cells and thereby prevent pathogen attachment which is usually essential in pathogen infection. In order to prevent pathogen/receptor interaction, such compounds can either bind to the pathogen antigen that binds to the receptor or to the receptor.

3. To construct biologically active compounds which mimic biologically active proteins by binding to the receptor sites of those cells, such binding causing alterations or effects to cellular function or behavior. Examples of such biologically active proteins include cytokines, hormones and growth factors.

4. To construct biologically active compounds which bind to the receptor sites of those cells to prevent or alter the effect which a biologically active proteins would otherwise have upon those cells.

5. To construct biologically active compounds which bind to biologically active proteins, preventing the biologically active protein from binding to the receptor site on a cell, thereby preventing the protein from causing the effect which a biologically active protein would otherwise have upon those cell.

The invention can be practiced by modeling compounds based upon similarity between pathogen antigens or biologically active proteins and the CDR loops on the loop portions of the alpha helix of an anti-idiotypic antibodies or by modeling peptides based upon similarity between pathogen antigens or biologically active proteins and anti-receptor antibodies. In each case, the same result is achieved. That is, the identification of portions of an antibody sequence, a CDR loop, which are identical or similar to relevant significant regions of a biologically significant protein; i.e. epitopes of antigens or biologically active portions of biologically active proteins.

In the case of construction of immunogenic compounds which mimic pathogen antigen neutralizing epitopes, anti-idiotypic antibodies specific for antibodies against the pathogen antigen neutralizing epitope contain sequences corresponding to the pathogen antigen neutralizing epitope. The pathogen antigen neutralizing epitope can be identified by comparing the amino acid sequence of the pathogen antigen to the amino acid sequence of the anti-idiotypic antibodies, particularly the variable regions, particularly the CDR regions. By identifying which portion of the pathogen antigen contains the neutralizing epitope, compounds such as peptides can be synthesized which are either identical or similar to the epitope of the antigen or to the region of the antibody. Vaccines can be formulated which include such compounds. These compounds will elicit a neutralizing antibody response and immunity or protection from pathogenic infection will be conferred upon the subject of the vaccination.

In the case of construction of biologically active peptides which block the binding of pathogens to receptors on host cells, the amino acid sequences of pathogen antigens involved in such binding can be identified by raising antibodies against the receptor and comparing the amino acid sequence of the pathogen antigen to the amino acid sequence of the anti-receptor antibodies, particularly the variable regions, particularly the CDR.

Alternatively, anti-idiotypic antibodies specific for antibodies that bind to pathogen antigens and thereby prevent binding of the pathogen to the receptor can contain amino acid sequences that correspond to the amino acid sequences of the pathogen antigen which binds to the receptor. The amino acid sequence of the pathogen antigen that binds to the receptor can be identified by comparing the amino acid sequence of the pathogen antigen to the amino acid sequence of the anti-idiotypic antibodies, particularly the variable regions, particularly the CDR regions.

In either of these cases, by identifying the portion of the pathogen antigen that binds to the receptor, compounds can be synthesized which are either identical or similar to the antigen sequence or to the region of the antibody. The peptides can be administered to a patient. These compounds will block a pathogen from binding to the receptor and thereby prevent pathogen attachment which is usually essential in pathogen infection.

Pathogen binding to cellular receptors has been associated with alterations or effects on cell function and activity. In order to construct biologically active peptides which mimic the binding of pathogens to receptors on host cells, the amino acid sequences of pathogen antigens involved in such activity can be identified by raising antibodies against the receptor which mimic the activity and comparing the amino acid sequence of the pathogen antigen to the amino acid sequence of the anti-receptor antibodies, particularly the variable regions, particularly the CDR regions. Compounds can be constructed which are based upon the portions of both molecules that correspond to each other, that is, that share sequence similarity. Such compounds will either block the mimic the effect that pathogen binding has on cells or prevent pathogen binding from occurring and thereby prevent the effects caused by pathogen binding.

It is contemplated that pathogen/receptor binding can be prevented by constructing biologically active compounds which mimic the receptor site and bind to the pathogen antigen. Such compounds are essentially "caps" to the antigen's receptor binding site and prevent the antigen from interacting with the receptor. In order to construct such biologically active compounds, the amino acid sequences of receptor site involved in pathogen binding can be identified by raising anti-idiotypic antibodies specific for anti-receptor antibodies that block pathogen binding and comparing the amino acid sequence of the receptor to the amino acid sequence of the anti-idiotypic antibodies, particularly the variable regions, particularly the CDR regions. Compounds can be constructed which are based upon the portions of both molecules that correspond to each other, that is, that share sequence similarity. Such compounds will mimic the receptor site and bind to the pathogen antigen at the receptor binding site, preventing the pathogen from binding to the receptor.

In another embodiment of the invention, biologically active compounds can be constructed by identifying the biologically active portion of a biologically active protein. The biologically active portion of a biologically active protein can be identified by generating antibodies specific for the receptor with which the biologically active protein interacts. Such antibodies must either block the binding of the biologically active protein of the receptor or mimic the activity of the biologically active protein. The amino acid sequence of the biologically active protein is compared to the amino acid sequence of the anti-receptor antibodies, particularly the variable regions, particularly the CDR regions. Compounds can be constructed which are based upon the corresponding portions of both molecules, that is, that portions that share sequence similarity. Such compounds will either block the receptor or mimic the activity of the biologically active protein.

In another embodiment of the invention, binding of a biologically active protein to a receptor can be prevented by constructing biologically active compounds which mimic the receptor site and bind to the biologically active portion of the biologically active protein. Such compounds are essentially "caps" to the biologically active protein's receptor binding site and prevent the biologically active protein from interacting with the receptor. In order to construct such biologically active compound, the amino acid sequences of receptor site involved in biologically active protein/receptor binding can be identified by raising anti-idiotypic antibodies specific for anti-receptor antibodies that block biologically active proteins from binding to the receptor and comparing the amino acid sequence of the receptor to the amino acid sequence of the anti-idiotypic antibodies, particularly the variable regions, particularly the CDR regions. Compounds can be constructed which are based upon the corresponding portions of both molecules, that is, the portions that share sequence similarity. Such compounds will mimic the receptor site and bind to the biologically active protein at the receptor binding site, preventing the biologically active protein from binding to the receptor and thereby neutralizing its ability to affect cells. The essence of the invention is the discovery that the specific portion of anti-idiotypic antibody or an anti-receptor antibody that recognizes a neutralizing antibody or a receptor, respectively, corresponds to the neutralizing epitope of an antigen or the biologically active portion of a biologically active protein which normally binds to the receptor, respectively.

The techniques needed to practice the invention are well known to those having ordinary skill in the art. The starting materials needed to practice the invention are readily available.

Antibodies against a pathogen, a receptor or another antibody are produced by routine methods. One having ordinary skill in the art can design assays to determine whether an antibody is a neutralizing antibody. Such assays are well known and their design and operation routine. Similarly, one having ordinary skill in the art can design assays to detect whether a pathogen is blocked from attaching to a cellular receptor. Such assays are well known and their design and operation routine. Furthermore, one having ordinary skill in the art can design assays to determine the biological activity of a peptide including its ability to block the activity of another molecule are well known. Such assays are well known and their design and operation routine.

Amino acid sequence determination can be readily accomplished by those having ordinary skill in the art using well known techniques. Generally, DNA sequencing of relevant genetic material can be performed and the amino acid sequence can be predicted from that information. Sequencing of genetic material, including the variable regions of antibodies, particularly the CDRs, can be performed by routine methods by those having ordinary skill in the art.

One having ordinary skill in the art can readily determine whether or not one amino acid sequence corresponds to another. The determination of whether sequences are corresponding may be based on a comparison of amino acid or nucleic acid sequence, and/or protein structure, between the protein of interest, that is, the pathogen antigen, cellular receptor or biologically active protein, and a member of the immunoglobulin superfamily, in particular anti-idiotypic antibodies or anti-receptor antibodies, particularly the CDRs of the variable-regions of such antibodies.

By determining the number of identical and conservatively substituted amino acid sequences shared between two molecules, one having ordinary skill in the art can determine whether or not two sequences correspond. The two sequences correspond if they share approximately at least 80% identical and conservatively substituted sequences of which at least about 28% are identical sequences and between about 30–42% conservative substitutions. Generally, corresponding amino acid sequences share at least six similar amino acid residues. Corresponding sequences are often longer, comprising about 10 or more similar residues. One having ordinary skill in the art, using routine techniques can by quantification determine whether two sequences are correspond within the meaning used herein.

Assays to determine whether or not antibodies are useful in a method to identify biologically active peptides can be readily designed and performed by those having ordinary skill in the art. Determination of whether an anti-pathogen antibody is neutralizing can be done by those having ordinary skill in the art. Determination of whether an anti-receptor antibody mimics or blocks a biologically active protein can be done by those having ordinary skill in the art.

Antibodies are generated against a pathogen by routine methods and, if they are found to be neutralizing, that is, if they prevent infection, anti-idiotypic antibodies are generated against the anti-pathogen antibodies. If the anti-idiotypic antibodies are capable of eliciting neutralizing antibodies, the anti-idiotypic antibodies are sequenced. Sequencing of the antibody can be directed at the variable regions, particularly the CDRs, by well known methods. The portion of the amino acid sequence of the antibody that corresponds to an amino acid sequence of the antigen of the pathogen is identified by sequencing both the antibody and the pathogen. The portion of the antibody where the similarity usually occurs is the variable region, in particular the CDR. A peptide is constructed which contains the amino acid sequence of the pathogen that corresponds to a portion of the anti-idiotypic antibody or which contains the amino acid sequence of the corresponding portion of the anti-idiotypic antibody. The peptide's ability to elicit a neutralizing antibody is confirmed. The peptide is useful in a vaccine to protect against infection of the host by the pathogen.

Antibodies are generated against a receptor that a pathogen binds to in order to attach to a cell. An assay can be performed to determine whether or not the anti-receptor antibody prevents the pathogen from binding to the receptor. The portion of the antibody corresponding to the antigen involved in receptor binding is identified by sequencing the antibody. Sequencing of the antibody can be directed at the variable regions, particularly the CDRs, by well known methods. The peptide is synthesized and will block prevent pathogen attachment to the receptor. The peptide is formulated as a pharmaceutic which is administered, for example, as a therapeutic to combat pathogen infection.

Pathogens and biologically active proteins such as cytokine, hormones and growth factors, bind to cellular receptors and alter the activity or function of a cell. Biologically active peptides are constructed according to the invention which, by binding to the receptor, mimic the effect that pathogens or biologically active proteins have on cells. Alternatively, biologically active peptides are constructed which prevent the binding of pathogens or biologically active proteins to the receptor and thereby prevent or alter the effect those agents would otherwise have upon the cells.

Antibodies are generated against a receptor and selected for their ability to mimic the effect that pathogens or biologically active proteins have on cells. If the antibodies are active, the portion of the antibody that is corresponds to either a portion of the pathogen antigen involved in receptor binding or a portion of the biologically active protein is identified by sequencing the antibody and the pathogen antigen or biologically active protein, respectively. Sequencing of the antibody can be directed at the variable regions, particularly the CDRs, by well known methods. The peptide is synthesized and will mimic the pathogen or biologically active protein. The peptide is formulated as a pharmaceutic which is administered, for example, as a therapeutic to elicit the activity of that the native proteins have on cells.

In order to identify biologically active peptides which prevent biologically active proteins from binding to cellular receptors, antibodies are generated against the receptors. Antibodies that compete with biologically active proteins in binding to the receptor but that do not mimic the effect that biologically active proteins have on cells are selected. If the antibodies are block binding but are not active, the portion of the antibody that corresponds to a portion of the biologically active protein is identified by sequencing the antibody and biologically active protein. Sequencing of the antibody can be directed at the variable regions, particularly the CDRs, by well known methods. The peptide is synthesized and will block the biologically active protein but will not mimic its activity. The peptide is formulated as a pharmaceutic which is administered, for example, as a therapeutic to counteract the activity of the biologically active protein.

Biologically active compounds, such as peptides, can be constructed which mimic the binding site of the receptor and thereby bind to the binding portion of either a pathogen antigen or a biologically active protein. Such peptides bind to the pathogen antigen or biologically active protein, effectively preventing those proteins from binding to the receptor. In order to identify biologically active peptides which mimic receptor binding sites and bind to either pathogen antigens or biologically active proteins, antibodies are generated against the pathogen antigens or biologically active proteins receptors. Alternatively, anti-idiotypic antibodies raised against anti-receptor antibodies can also be used. The antibodies are tested to identify those that prevent pathogen antigens or biologically active proteins from binding to cellular receptors. Antibodies that compete with receptors to bind with pathogen antigens or biologically active proteins are selected. If the antibodies are block binding, the portion of the antibody that corresponds to a portion of the receptor is identified by sequencing the antibody and receptor. Sequencing of the antibody can be directed at the variable regions, particularly the CDRs, by well known methods. The peptide is synthesized and will bind to either the pathogen antigen or the biologically active protein, thus preventing those proteins from binding to the receptors. The peptide is formulated as a pharmaceutic which is administered, for example, as a therapeutic to counteract the activity of the biologically active protein.

Peptides can be synthesized by those having ordinary skill in the art using well known techniques and readily available starting materials. According to the invention, references to synthesizing or constructing peptides is herein construed to refer to the production of peptides similar in sequence or structure to the corresponding regions identified by the method of the invention. These peptides may be produced using any method known in the art, including, but not limited to, chemical synthesis as well as biological synthesis in an in vitro or in vivo in a eukaryotic or prokaryotic expression system. The peptides may consist of only corresponding regions or they may comprise the corresponding sequences and addition sequences.

Peptides of the invention may be biologically active as produced or may require modification in order to assume a three-dimensional conformation which is biologically active. Generally, the peptides are active as produced. However, some modifications may be necessary for activity and some modifications may be desirable to improve or alter activity.

Modifications which may be performed, using standard techniques, according to the invention include but are not limited to cyclization, disulfide bond formation, glycosylation, phosphorylation, or the addition or subtraction of amino acid residues including amino acid residues which serve to produce a useful three dimensional conformation via a chemical linkage which is not generally found in natural peptides and/or mimetics including but not limited to, those described in Freidinger et al., 1980, Science 210:656; Hinds et al., 1988, J. Chem. Soc. Chem. Comm. 1447; Kemp et al., 1984, J. Org. Chem. 49:2286; Kemp et al., 1985, J. Org. Chem. 50:5834; Kemp et al., 1988, Tetrahedron Lett. 29:5077; Jones et al., 1988, Tetrahedron Lett. 29:3853.

Additionally, modifications may be performed, using standard techniques, according to the invention to create dimers or oligomers of the loops or multi-looped structures.

An increase or decrease in bioactivity associated with modification may be ascertained using the appropriate assay system. For example, if the activity of the peptide is associated with immunogenicity, the ability of modified and unmodified peptides to elicit an immune response may be compared.

Further, if the desired geometry of a peptide is known, computer modelling may be used to identify modifications of the peptide which would result in the desired geometry. The success of these modifications in increasing bioactivity could then be evaluated using in vitro or in vivo assay systems.

EXAMPLES

Example 1

The following embodiments of the invention are described in connection with experiments which have been conducted using reovirus types 1 and 3 interactions with cellular receptors using the anti-idiotype anti-receptor approach.

MATERIALS AND METHODS

Mice

Adult Balb/c female mice, 6 to 8 weeks to age, were obtained from Jackson Laboratories, Bar Harbor, Me.

Pre-immune serum was obtained on all mice used and assayed by neutralization of reovirus infectivity (see below) to ascertain that there had been no prior exposure to reovirus. Mice immunized with peptides were housed in the animal care facility and fed a house diet ad libitum (Purina, St. Louis, Mo.). Mice immunized with reovirus type 3/Dearing were housed in a separate facility.

Viruses

Reovirus type 1 (Lang), and reovirus type 3 (Dearing) and the reassortants 3.HA-1 and 1.HA-3 have been previously described (Fields, B. N. and Greene, M. I., Nature 20:19–23, 1982). Clones 1.HA-3 and 3.HA-1 are single segment reassortant clones that segregate the S1 gene, the gene encoding the viral attachment polypeptide (hemagglutinin) sigma 1. For mouse inoculation and virus neutralization, a stock of reovirus that was passed twice in L-cells was purified by substituting ultrasonic disruption (Branson Ultrasonic 200) for cell homogenization in a modification of published techniques (Joklik, W. K., Virology 49:700–715, 1972). The number of particles per ml was determined by optical density at 260 nm (Smith, R. E. et al., Virology 39:791–810, 1969).

Monoclonal Antibodies

Type 3 reovirus neutralizing monoclonal antibody 9BG5 (mouse IgG2aK) (Burstin, S. J. et al., Virology 117:146–155, 1982) was purified from hybridoma supernatant with the cells grown in Dulbecco's minimal essential media (DMEM) (MA Bioproducts, Walkersville, Md.) with added penicillin/streptomycin solution (The Cell Center, University of Pennsylvania, Philadelphia, Pa.), and 10% fetal bovine serum (FBS). Culture supernatants were precipitated with 50% $(NH_4)_2SO_4$, solubilized in distilled water and dialyzed against three changes of phosphate buffered saline (PBS). Next, the antibody was purified on a Sepharose-protein A column and eluted with 0.1 M citric acid pH 4.5. The eluate was collected in 1 M tris buffer, pH 8.5 to neutralize excess acidity and dialyzed against three changes of PBS. The dialysate was concentrated on an Amicon protein concentrator with a molecular weight cut-off of 30 kilodaltons (kD). The purified antibody was more than 95% pure by sodium-dodecyl sulfate polyacrylamide gel electrophoresis (SDS-PAGE). Irrelevant monoclonal antibodies UPC-10 and All (both mouse IgG2aK) were similarly purified from clarified ascites (Gibco, Grand Island Biological Co.).

Monoclonal antibodies 87.92.6 (mouse IgM, K) and HO 13.4 (mouse IgM, K, anti-Thy 1.2) and HO 22.1 (mouse IgM, K, anti-Thy 1.1) were purified from 50% ammonium sulfate cuts of culture supernatant or from ascites supernatants from ascites generated in hybridoma bearing Balb/c mice. These preparations were dialyzed against three changes of PBS and run over a goat anti-mouse IgM Affigel-10 column. Antibodies were eluted with 3.5 M $MgCl_2$, dialyzed against three changes of PBS and concentrated as noted above. Purity of all monoclonal antibodies used was greater than 95% by SDS-PAGE.

Cell Lines

Murine L-cells were grown in spinner bottles with Joklik's MEM (MA Bioproducts) with 5% FBS. R1.1 cells (murine thymoma, Thy 1.2+) were grown in suspension in RPMI 1640 (MA Bioproducts, Walkersville, MD) supplemented with L-glutamine, 10 mM HEPES buffer (MA Bioproducts) and penicillin/streptomycin with 10% FBS.

Immunization of Mice

For the study of DTH response, groups of mice were inoculated with either synthetic peptide or live reovirus type 3 subcutaneously (s.c.) in two separate sites on the dorsal flanks of the animal (over each hind limb); 50 $\mu$g of a synthetic peptide or $10^7$ viral particles/0.2 ml were given in separate injections of 0.1 ml vol. Six days later, animals were challenged in the left footpad with $3\times10^7$ viral particles suspended in saline containing 2% gelatin (30 $\mu$l). Footpad swelling was recorded 24 hr later in a blind fashion (Greene, M. I. and Weiner, H. L., J. Immunol. 125:283–287, 1980). Four animals per group were studied, and the magnitude of the response was determined by comparing the challenged left footpad to the untreated right footpad.

For the study of humoral immune response, mice were inoculated with either synthetic peptide or live reovirus type 3 as above with the following modification. The peptide was conjugated with chicken serum albumin (CSA) as described below and 100 $\mu$g of the peptide conjugate was inoculated s.c. in two divided doses. For mice immunized with synthetic peptides, the first immunization was with peptide mixed with an equal volume of complete Freund's adjuvant; whereas with subsequent immunization the peptide was suspended in saline containing gelatin. Mice were immunized weekly for five weeks, and serum was obtained prior to the first inoculation, and then at the second and sixth week. For mice immunized with reovirus type 3, $10^7$ plaque forming units (PFU) was inoculated s.c. on the first and third week.

Radioimmunoassay Procedure

The wells of 96 well V-bottom polystyrene plates (Dynatech Laboratories, Alexandria, Va.) were coated with peptide by diluting the peptides to 25 $\mu$g/ml in distilled water and evaporating 50 $\mu$l in each well by incubating the plates overnight at 37° C. Wells were coated with reovirus type 1 or type 3 by diluting stock solutions of virus to $4.8\times10^{11}$ particles/ml in 0.1 M $NaHCO_3$ pH 9.5, dispensing 25 $\mu$l per well and incubation overnight at 4° C. (London, S. D., et al. 1987). Following overnight incubation, peptide or virus coated wells were washed three times with PBS and blocked with 200 $\mu$l/well of 1% gelatin in PBS with 0.1% $NaHCO_3$ by incubation for 2 hours at 37° C. The wells were decanted, washed three times in PBS, and mouse serum or purified monoclonal antibody was added, 50 $\mu$l/well, diluted in PBS containing 0.5% gelatin and 0.1% $NaN_3$. Following a 3 hour incubation at 37° C., the wells were decanted, washed three times in PBS, and radioiodinated goat anti-mouse Kappa diluted in PBS 0.1% $NaHCO_3$ with 1 mg/ml chicken gamma globulin was added, 100 $\mu$l =48,000 counts per minute (CPM) per well. The plates were incubated overnight at 4° C., decanted, washed ten times in tap water and dried under a heat lamp. Wells were then cut out using a hot wire and counted in a gamma counter. The CPM determined on blank wells not coated with. antigen is subtracted from CPM values determined on antigen coated wells in all cases.

Fluorescence Activated Cell Sorter (FACS) Analysis

R1.1 cells (99% viability to trypan blue dye exclusion) were centrifuged and washed twice in PBS 0.1% $NaN_3$ with 1% bovine serum albumin (FACS media). Cells were resuspended at $10^7$/ml either in FACS media alone or FACS media containing peptide-BSA conjugates at 200 $\mu$g/ml. The cells were incubated on ice for 45 minutes prior to addition of monoclonal antibodies from 0.5 mg/ml stock solutions to 100 $\mu$l aliquots to the final concentrations noted. Following an additional 30 minute incubation, 500 $\mu$l of FACS medium was added to each sample, the cells were centrifuged, washed once in 500 $\mu$l FACS media, resuspended in 10 $\mu$l FACS containing a 1:200 dilution of fluoresceinated goat anti-mouse Fab (Southern Biotechnology Associates) and incubated for 30 minutes on ice. 500 $\mu$l of FACS media was added, the cells were centrifuged and washed in 500 $\mu$l FACS media, resuspended in 200 $\mu$l FACS media and analyzed at the University of Pennsylvania fluorescence activated cell sorter.

Neutralization of Virus Infectivity

The titer of neutralizing antibodies in serum sample were determined in the following manner:

(i) Micro-neutralization: L-cells ($5\times10^4$ per well) were incubated in 96 well dishes overnight at 37° C. Reovirus type 1/Lang (1/L) and type 3/D were serially diluted and incubated for 1 hour with the L-cells at 37° C. An additional 75 $\mu$l of MEM supplemented with 5% fetal bovine serum, 1% glutamine was placed in each well. At 3 days following incubation at 370°, the media containing virus was removed and the cells were stained with Gentian Violet (Gentian Violet 3.4 g/l, ammonium oxalate 8 g/l). The titer of virus used for neutralization was 4 fold in excess of that quantity of virus that was lytic for the L-cell monolayer.

Reovirus type 1/L or 3/D at the appropriate concentration was incubated with an equal volume of mouse serum for 1 hr at 25° C on 96 well plates. The virus-serum mixture was then transferred to L-cell monolayers as above. The titer of antibody was determined as the amount which preserved 70% of the monolayer as determined by visual inspection.

(ii) Virus plaque reduction: 100 pfu of reovirus type 1/L incubated for 1 hour with L-cells ($7\times10^5$ cells per well) in 12 well Costar plates. The titer of virus in each well was then determined as previously described (Rubin, D. H., J. Virol. 53:391–398, 1985).

Synthesis of Peptides

Peptides were synthesized using a model 430 A Applied Biosystems Peptide Synthesizer (Applied Biosystems, Inc., Foster City, Calif.). Deprotection and release of the peptide from the solid phase support matrix were accomplished by treating the protected peptide on the resin with anhydrous HF containing 10% anisole or 10% thioanisole for 1 to 2 hr at 0° C. The peptides were then extracted with either ethyl acetate or diethylether and then dissolved in 10% aqueous acetic acid and filtered to remove the resin. After lyophilization, the composition and purity of the peptides were determined with both amino acid analysis and reverse phase high performance liquid chromatography. This procedure was used for the synthesis of all peptides, including $V_L$ and the variant peptides of $V_L$.

Conjugation of Peptides to Chicken Serum Albumin (CSA)

Prior to conjugating the peptides to CSA, the CSA was first derivatized with a nucleophilic spacer consisting of adipic dihydrazide, as described by Schneerson, et al., J. Exp. Med. 152:361, (1980). 30 mg of the adipic dihydrazide-derivatized-CSA (CSA-ADH) in 5 ml 0.1 M sodium bicarbonate was reacted for 15 min at room temperature with 7 mg m-maleimidobenzoylsulfosuccinimide ester (Pierce). To this reaction mixture was then added 50 mg peptide and the couples reaction was allows to proceed at 25° C. for 2 hr. Following dialysis against 0.1 M ammonium bicarbonate and lyophilization, the CSA-ADH-peptide conjugates were obtained as dry white powders.

RESULTS

Determination of Shared Peptide Sequence

Prior work has shown that a monoclonal antibody denoted 87.92.6 raised against monoclonal neutralizing anti-reovirus antibody 9BG5 mimics the intact virus by binding to cell-surface receptors specific for type 3 reovirus. See Noseworthy, J. H. et al., J. Immunol. 131:2533–2538, 1983; Kauffman, R. S., et al, 1983 supra; and Co, M. S. et al., Proc. Natl. Acad. Sci. USA 82:1494–1498, 1985. Monoclonal antibody 87.92.6 competes with reovirus type 3 for binding to specific cellular receptors thereby mimicking the viral cell attachment protein sigma 1 (the viral hemagglutinin) in its binding domain. This domain is also implicated in the neutralizing antibody response (Burstin, S. J., et al, 1982 supra; Spriggs, D. R. et al., Virology 127:220–224 1983). This implies that 87.92.6 mimics the epitope on the hemagglutinin that interacts with the cellular receptor for reovirus.

The nucleic acid sequences of the heavy and light chain variable regions ($V_H$ and $V_L$ respectively) of 87.92.6 have recently been determined (Bruck, C. et al., Proc. Natl. Acad. Sci. USA 83:6578–6582, 1986), and the sequences have been compared to that of the reovirus type 3 sigma 1 protein (Bassel-Duby, R. et al., Nature 315:421–423, 1985). In accordance with the methods of the invention, shared sequence portions of the antigen and anti-idiotype have been identified. More particularly, a 16 amino acid sequence in the reovirus type 3 sigma 1 protein encompassing amino acids 317 and 332 has been identified as having corresponding amino acid sequences to a combined sequence encompassing the second complementarity determining regions (CDR II's) of the 87.92.6 heavy and light chain variable regions ($V_H$ and $V_L$ respectively). Specifically, amino acids 43–51 of the $V_H$ share sequence similarity with amino acids 317–324 of sigma 1 and amino acids 46–55 of the $V_L$ correspond to amino acids 323–332 of sigma 1 (Bruck, C., et al, 1986, supra).

In accordance with the methods of the invention, peptides corresponding to amino acids 317–332 of the sigma 1 protein 43–50 of the $V_H$ sequence and 39–55 of the $V_L$ sequence have been synthesized. As demonstrated hereinafter, immunization of Balb/c mice with these peptides results in neutralizing anti-reovirus type 3 antibodies and specific cell-mediated immunity to reovirus. This establishes that the corresponding sequences between the sigma 1 cell attachment protein and the anti-receptor antibody predicts the neutralizing epitope on the reovirus hemagglutinin, sigma 1. This approach allows the rapid delineation of neutralizing epitopes on pathogens and the development of peptide vaccines that elicit a neutralizing response.

Binding of Neutralizing Monoclonal Antibody 9BG5 to Peptides

The monoclonal anti-receptor antibody 87.92.6 binds to both the reovirus type 3 receptor and the neutralizing antibody 9BG5 (Kauffman, R. S., et al, 1983, supra). Applicants predicted that the peptides derived from the areas of similarity between 87.92.6 and the type 3 reovirus sigma 1 protein (Bruck, C., et al, 1986 supra) would have similar properties. The peptides synthesized to test this hypothesis are shown in Table I.

The peptides used in this study were synthesized by solid-phase methods as noted above. The sequences are shown aligned with maximum similarity. The amino acids marked with a closed circle are identical and those marked with an open circle are of the same. class. It will be noted that the tested peptides contain anti-idiotypic antibody residues in addition to the shared peptide sequence.

The reo peptide corresponds to amino acids 317–332 in the type 3 viral hemagglutinin. Computer modeling predicts this area to be predominantly a beta-sheet configuration and to include a beta-turn. The $V_L$ peptide represents amino acids 39–55 of the light chain variable. region of 87.92.6, and includes the second complementarity determining region (CDR II). Modeling predicts this area also to be a predominant beta-sheet and to include a beta-turn. The $V_H$ peptide comprises amino acids 43–56 of the heavy chain variable region of 87.92.6 including CDR II of the heavy chain. The control peptide, unrelated to this system, is also shown.

Figure 1:
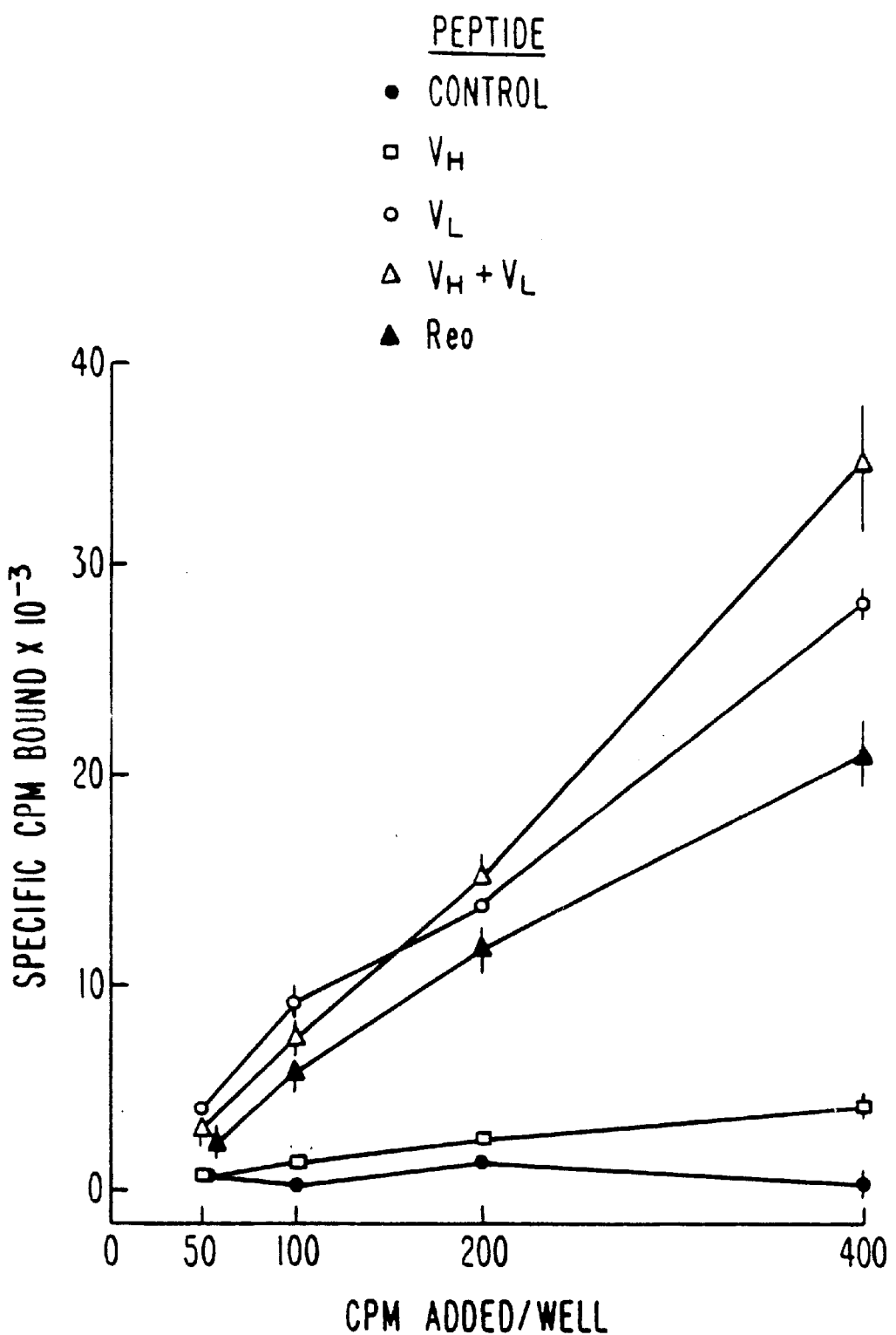

Based on these similarities in primary and secondary structures, it was predicted that the reo and $V_L$ peptides should be recognized by anti-reovirus type 3 neutralizing monoclonal antibody 9BG5. FIG. 1 shows the results of a radioimmunoassay determining the binding of purified monoclonal antibody 9BG5 to the wells of microtiter plates coated with the peptides. To control for non-specific binding to the polystyrene wells, counts per minute (CPM) determined on blank wells not coated with peptide is subtracted from CPM values determined on peptide coated wells. In addition, since these peptides may also cause non-specific adherence of immunoglobulin molecules, the specific binding of the class-matched irrelevant monoclonal antibody UPC-10 to peptide coated wells and subtracted this value from those determined for 9BG5 was determined. No significant binding was seen to the control peptide used in this study. Similarly, binding to the $V_H$ peptide only achieved background levels indicating that this epitope is not recognized by 9BG5. There was a small amount of binding to the $V_L$ peptide, which has strong similarity in its carboxy terminal sequence to the reo peptide carboxy terminal. Although slight, this finding was reproducible on subsequent assays. Strong reproducible binding to the reo peptide by 9BG5 was evident. Since 9BG5 is a neutralizing antibody, this datum implies that the reo peptide contains the neutralizing epitope recognized by 9BG5. The binding to the $V_L$ peptide indicates that the area of sequence between these peptides (amino acids 323–332 of the sigma 1 protein) is involved in the neutralizing epitope.

Binding of $V_L$ Peptide to the Reovirus Receptor

Figure 2B:
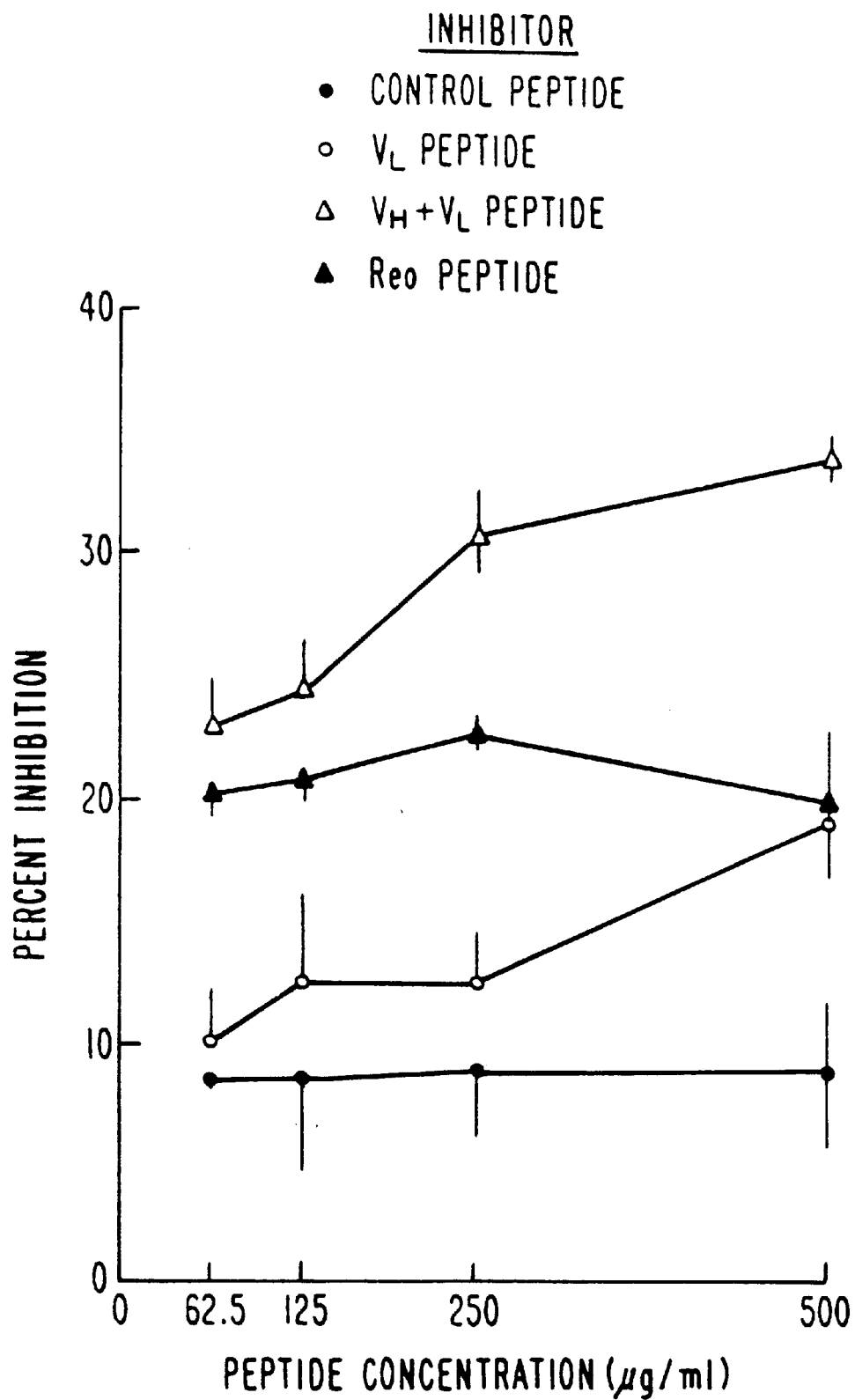

Prior work indicated that the neutralizing epitope recognized by 9BG5 is involved in binding to the type 3 reovirus receptor (Kauffman, R. S., et al. (1983) supra; Noseworthy, J. H., et al. (1983) supra; Spriggs, D. R., et al. (1983) supra). It was therefore speculated that the $V_L$ peptide might also interact with the viral receptor. To test this hypothesis the $V_H$ and $V_L$ peptides were coupled to BSA by incubating peptides and BSA in 0.1% glutaraldehyde followed by dialysis against PBS. These preparations were used to determine if 87.92.6 specifically blocked binding to the type 3 reovirus receptor on R1.1 cells. As shown in FIG. 2a, pre-incubation of R1.1 cells with $V_L$-BSA blocked the binding of 87.92.6 indicating interaction of $V_L$-BSA with the reovirus receptor. This blocking effect is specific as pre-incubation of R1.1 cells with $V_L$-BSA had no effect on the binding of HO 13.4, and isotype matched control monoclonal antibody that binds to the Thy 1.2 molecule on the R1.1 cell surface (FIG. 2b). These observations were consistently reproducible on multiple experiments. An additional control is shown in FIG. 2B where it is demonstrated that $V_H$-BSA has no inhibitory effect on 87.92.6 binding when used at the same concentrations as $V_L$-BSA. These data indicate a direct interaction of the $V_L$ peptide with the reovirus type 3 receptor and imply that residues 46–55 of the 87.92.6 $V_L$ chain and 323–332 of the type 3 sigma 1 protein directly interact with the reovirus type 3 receptor.

Binding of Reovirus type 3 Inhibits Host Cell DNA Synthesis Upon Receptor Perturbation Reovirus type 3 inhibits host cell DNA synthesis upon receptor perturbation. This effect is not due to infection of cells as replication defective reovirus type 3 particles retain this property. L cells were cultured at $5 \times 10^4$ cells per well of 96 well microtiter plates in 100 µl media for 24 hours. Reovirus type 3 particles (A) were added and incubated for an additional 24 hours prior to the addition of tritiated thymidine. Purified monoclonal antibodies 87.92.6 or HO 22.1 (B) were added for 1 hour at 37° C., then the culture media removed and replaced with 100 µl fresh media for 24 hours, prior to the addition of tritiated thymidine. The cells were incubated for an additional 4–6 hours and counts per minute (CPM) incorporated were determined.

Figure 3A:
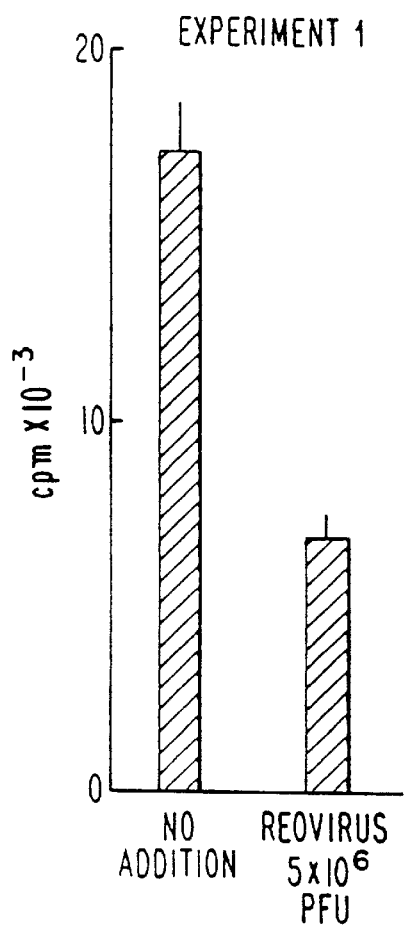
FIGS. 3A and 3B shows reovirus type 3 and 87.92.6 antibody inhibition of L cell proliferation.
Figure 3B:
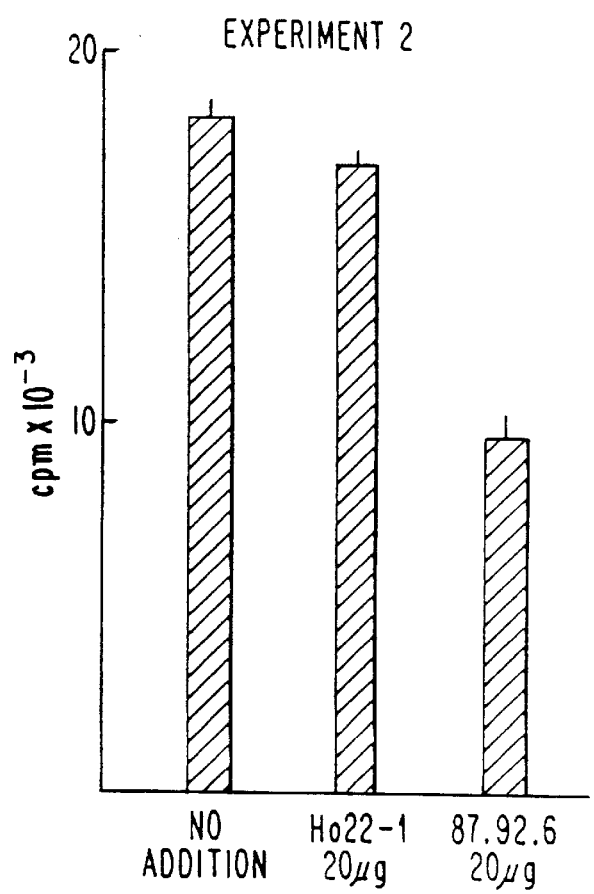

FIG. 3 shows this effect of reovirus type 3 upon murine fibroblasts. Murine fibroblasts (which posses specific receptors for reovirus type 3) (L cells), were incubated with reovirus type 3, or left untreated (3A). Twenty-four hours later the DNA synthetic level was measured. Reovirus type 3 markedly inhibited DNA syntheses by these cells. 87.92.6 has a similar effect on these cells, as shown in FIG. 3B. In this experiment, L cells were grown adherent and exposed to antibody for one hour, at which point the antibody was removed, and the cells cultured for an additional 24 hours prior to determination of the DNA synthesis while a control antibody (HO22.1) had no effect. 87.92.6 similarly inhibits DNA synthesis by fibroblasts, neuronal cells and lymphocytes.

Binding of Dimeric Peptides to Reovirus Type 3 Receptors

It was reasoned that $V_L$ peptide may exhibit biologic effects similar to those exhibited by reovirus type 3 and 87.92.6. 87.92.6 is effective only as a native antibody while monomeric Fab fragments have no effect. $V_L$ peptide was synthesized with an additional amino terminal cysteine residue ($V_L$SH) to form a dimeric peptide. $V_L$SH peptide was dimerized by stirring a 5 mg/ml solution in 0.1 M ammonium bicarbonate overnight at 23° C. exposed to air. The peptides were then lyophilized. Dimerization was confirmed by Ellman determination according to the procedure of Ellman, G. L. Arch. Biochem. Biophys. 74:443 (1958), which revealed less than 5% free sulfhydryl groups. L Cells were suspended at $10^6$ cells/ml in DMED 10% FBS and 50 µl added to each well of 96 well microtiter plates. Following 24 hours of culture, peptides were added to the concentrations noted, and the cells cultured for an additional 24 hours. Tritiated thymidine was added for an additional 4–6 hours, and counts per minute (CPM) incorporated was determined. Per cent inhibition was determined by the formula:

$$\left[1 - \frac{(CPM \text{ without additive}) - (CPM \text{ with additive})}{CPM \text{ without additive}}\right] \times 100$$

Figure 4:
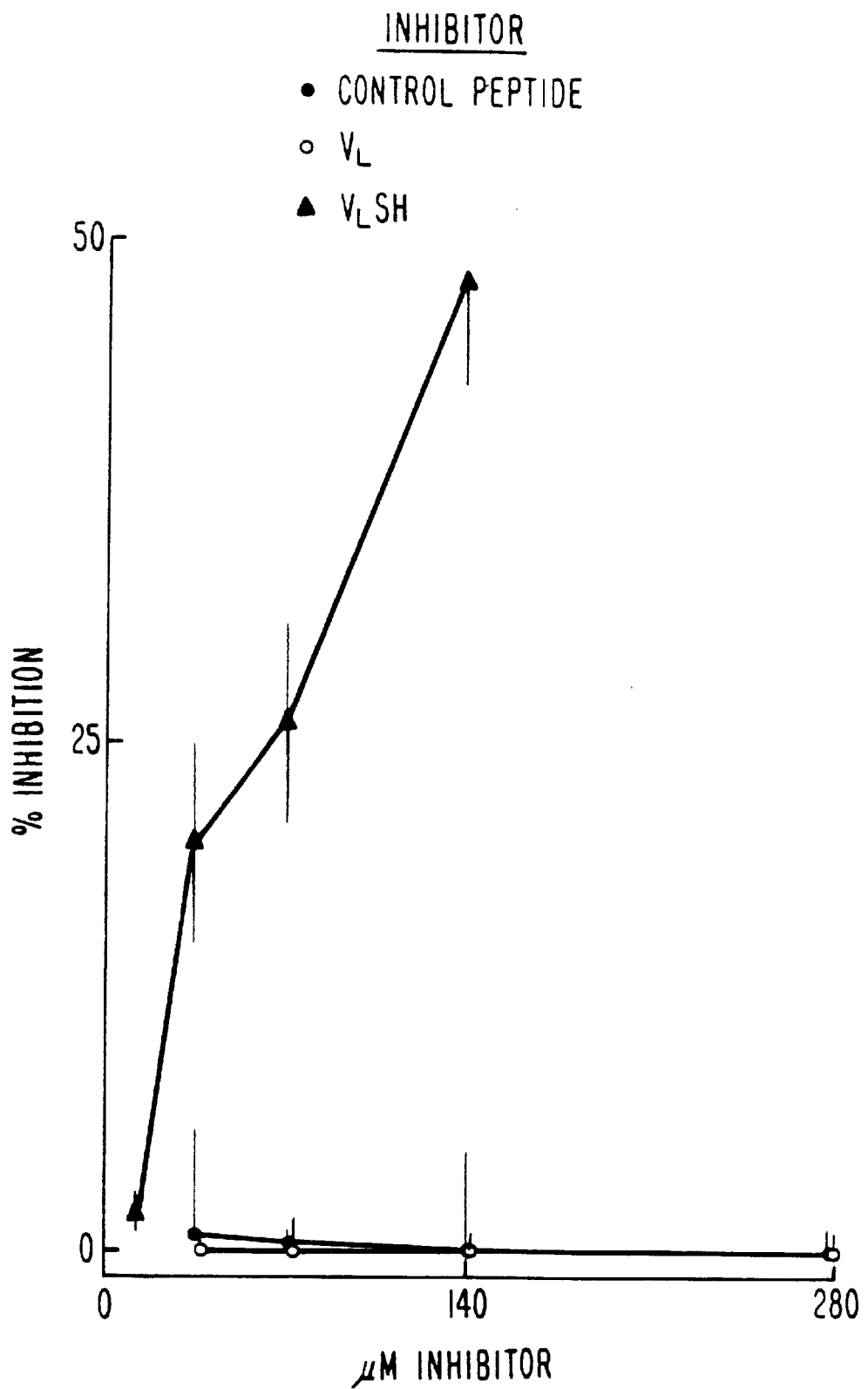
FIG. 4 shows inhibition of L cell proliferation by peptides.

The peptides utilized were:
$V_L$: Lys-Pro-Gly-Lys-Thr-Asn-Lys-Leu-Leu-Ile-Tyr-Ser-Gly-Ser-Thr-Leu-Gln $V_L$SH: Cys-Lys-Pro-Gly-Lys-Thr-Asn-Lys-Leu-Leu-Ile-Tyr-Ser-Gly-Ser-Thr-Leu-Gln Control: Cys-Tyr-Thr-Tyr-Pro-Lys-Glu-Asp-Thr-Ala-Asn-Asn-Arg As shown in FIG. 4, marked inhibition of DNA synthesis was observed when L cells were treated with $V_L$SH. $V_L$ peptide monomers (without the added cysteine residue) had no effect on L cell proliferation. Several control peptides utilized also had no effect in these assays (FIG. 4). This indicates that aggregation of the reovirus type 3 receptor on L cells is essential for the inhibition of DNA synthesis by these peptides.

Down-Modulation of Reovirus Type 3 Receptor By Peptide Dimers

Figure 5A:
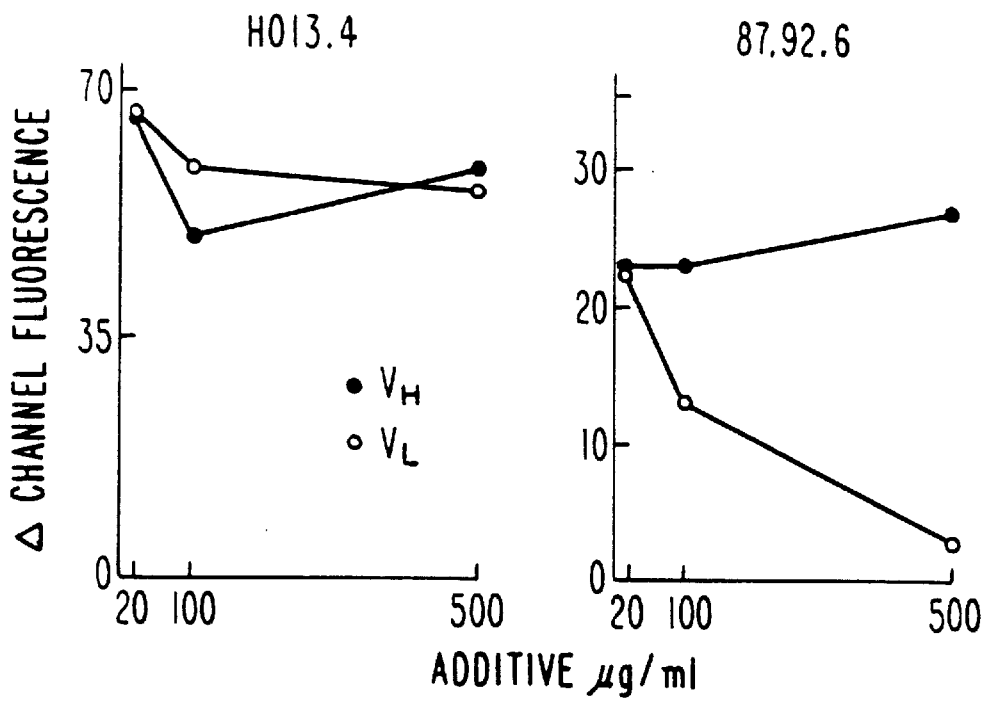
Figure 5B:
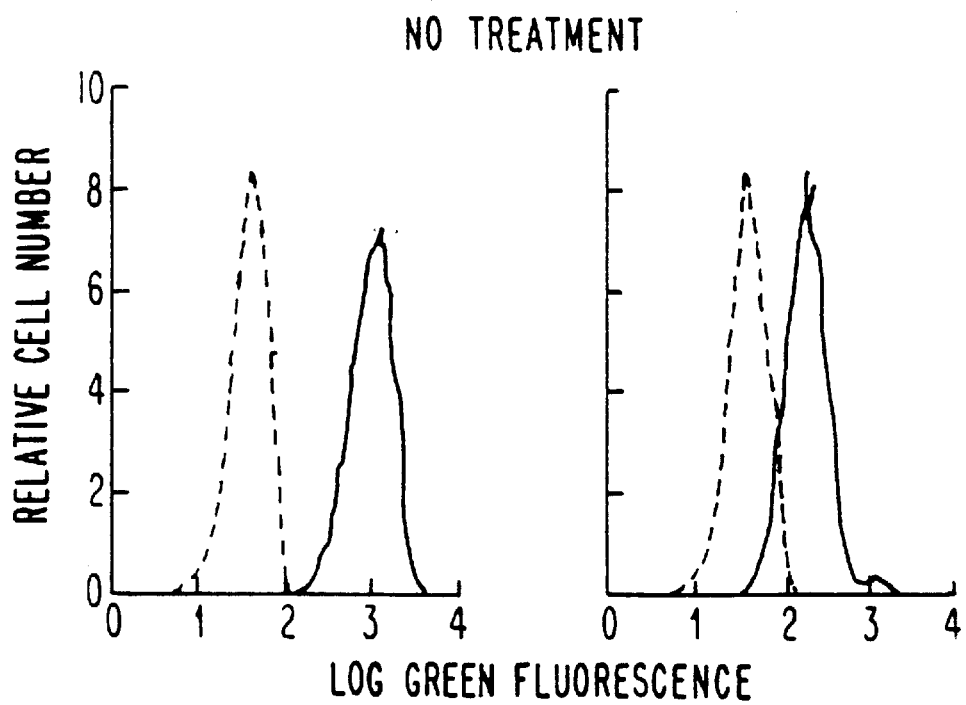
Figure 5C:
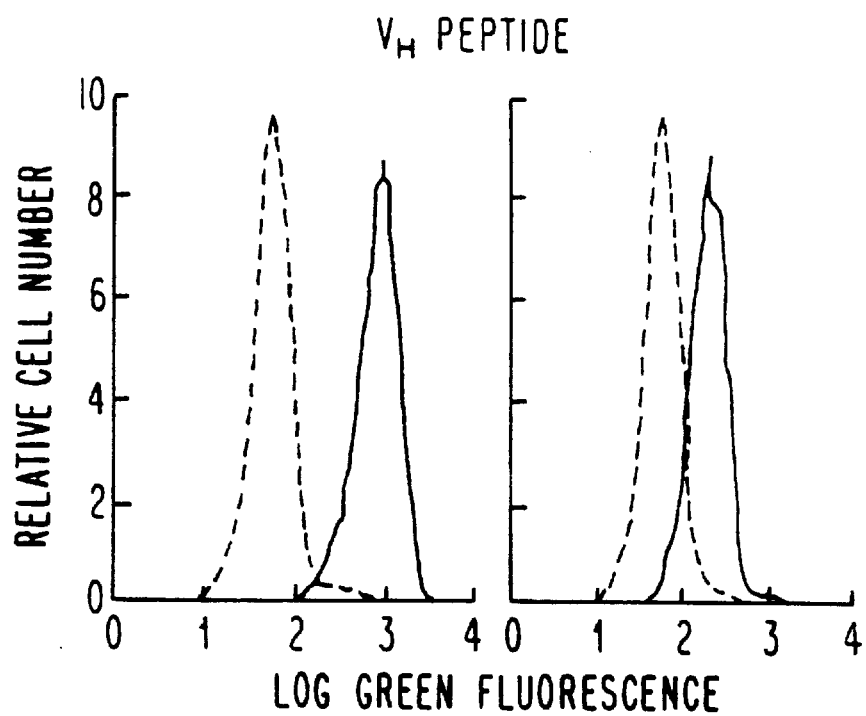
Figure 5D:
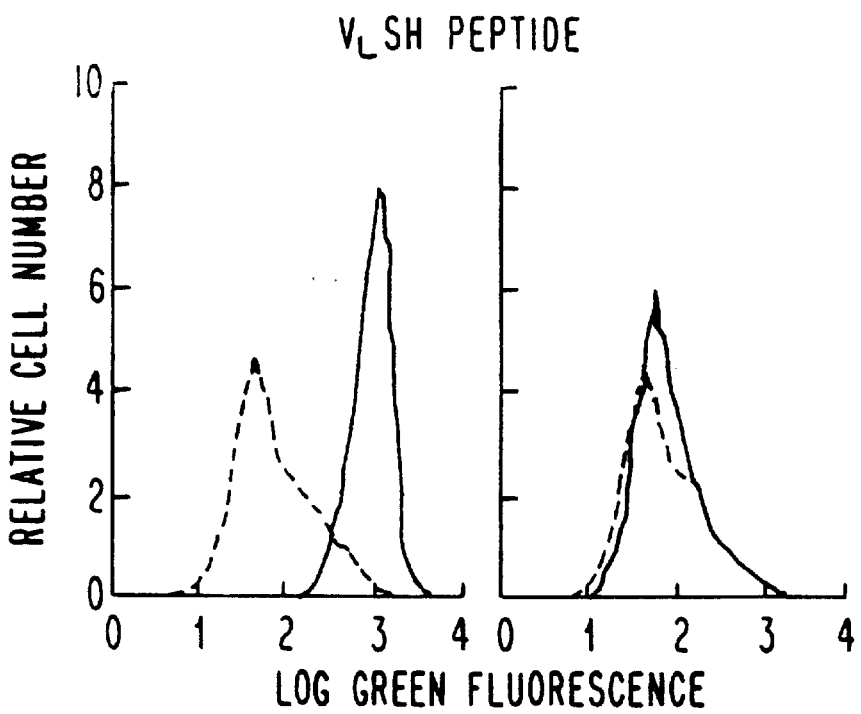

Aggregation of the reovirus type 3 receptor on some cells by 87.92.6 leads to disappearance of that receptor from the cell surface. It was reasoned that $V_L$SH peptide might similarly down-modulate this receptor. For these experiments we utilized murine thymoma (R1.1) cells, which have well characterized reovirus type 3 receptors were utilized. The effect of peptides on the level of expression of both the reovirus type 3 receptor (recognized by 87.92.6) and Thy 1.2 molecules (recognized by HO 13.4), as determined by flow cytometry was studied. R1.1 cells were cultured with peptides at the concentration noted (A), left untreated (B), or treated with 500 µg/ml peptide (C,D) for 1 hour at 37° C. The cells were centrifuged and washed three times in 1% BSA in PBS with 0.1% sodium azide (FACS media). Monoclonal antibodies 87.92.6 (100 µl of affinity purified antibody) was added for 30 minutes on ice. The cells were washed and 100 µl of a 1:100 dilution of fluoresceinated goat anti-mouse Ig (Southern Biotechnology Associates, Birmingham, Ala.) was added for 30 minutes. The cells were washed and fluorescence intensity analyzed by flow cytometry. Mean channel fluorescence was compared for cells incubated in the presence or absence of primary antibody to give mean channel fluorescence (FIG. 2B). Cells were stained with HO 13.4 (left panels in FIGS. 5A–D) which binds Thy 1.2 molecules, or with 87.92.6 (right panels in FIGS. 5A–D) which binds the reovirus type 3 receptor. Cells were treated with $V_H$ peptide (FIG. 5A, left panel, and FIG. 5C) or $V_L$SH peptide (FIG. 5A, right panel, and FIG. 5D).

The $V_H$ peptide sequence:
$V_H$: Cys-Gln-Gly-Leu-Glu-Gln-Ile-Gly-Arg-Ile-Pro-Ala-Asn-Gly The other peptides are those described above for FIG. 4. As shown in FIG. 4, $V_L$SH peptide specifically down-modulates the reovirus type 3 receptor in a dose-dependent manner, but does not effect the expression of Thy 1.2 molecules on these cells. This down-modulation is a direct biologic effect of $V_L$SH peptide and not due to other factors in the experimental design. The control peptide used ($V_H$ peptide) does not effect the level of expression of the reovirus type 3 receptor, or of Thy 1.2 molecules, on these cells. $V_H$ peptide was derived from the 87.92.6 heavy chain CDR II and does not specifically interact with the reovirus type 3 receptor. It has been demonstrated previously that $V_L$ peptide in this form does not compete with 87.92.6 for binding to these cells, although other forms of $V_L$ peptide are able to inhibit 87.92.6 binding. In addition, in the studies described in FIGS. 5A–D, the cells were washed thoroughly to remove free $V_L$SH peptides prior to flow cytometry. Collectively these data indicate that competition for binding to the reovirus type 3 receptor is not responsible for the decreased staining with 87.92.6. The down-modulation of the reovirus type 3 receptor accounts for this phenomenon.

Receptor down-modulation is dependent on aggregation of the receptor, as demonstrated in FIG. 6. Data from three experiments comparing the effect of $V_L$ peptide monomers and $V_L$SH peptide is shown. R1.1 cells were treated as described above with peptides (100 μg/ml) or 87.92.6 (a 1:1 dilution of ascites), and analyzed for expression of the reovirus type 3 receptor (87.92.6) or Thy 1.2 molecules (HO 13.4). Per cent decrease in mean channel fluorescence is calculated as follows: The mean channel fluorescence of peptide or antibody treated cells is subtracted from that of untreated cells, this divided by the mean channel fluorescence of untreated cells; the resultant value is subtracted for 1 and multiplied by 100. For peptide treated cells, mean channel fluorescence is determined on peptide treated cells in the presence or absence of primary antibody. For antibody treated cells, mean channel fluorescence is determined by the mean channel number of antibody treated cells in the presence of primary antibody minus the mean channel number of untreated cells in the absence of primary antibody. Cells treated with antibody and then analyzed without primary antibody staining had an increase in mean channel number when compared with untreated cells. The mean + standard deviation from 3 experiments is shown for peptide treated cells. The peptides used in these experiments included:

$V_L$: Lys-Pro-Gly-Lys-Thr-Asn-Lys-Leu-Leu-Ile-Tyr-Ser-Gly-Ser-Thr-Leu-Gln $V_L$SH: Cys-Lys-Pro-Gly-Lys-Thr-Asn-Lys-Leu-Leu-Ile-Tyr-Ser-Gly-Ser-Thr-Leu-Gln

Control: Cys-Thr-Tyr-Arg-Pro-Lys-Glu-Asp-Thr-Ala-Asn-Asn-Arg $V_L$ peptide monomers had no effect on reovirus type 3 receptor expressions. $V_L$SH peptide specifically down-modulated the expression of the reovirus type 3 receptor without effecting the expression of Thy 1.2 molecules. The effect of $V_L$SH peptide was similar to that of 87.92.6 (FIG. 6). The results indicate the specificity of the effect of $V_L$SH peptide on the reovirus type 3 receptor and confirm that receptor aggregation plays a role in the induction of these effects.

Role of Specific Residues Of $V_L$ Peptide Involved In The Interaction Of $V_L$ Peptide With The Reovirus Type 3 Receptor Once the shared regions were defined, variant peptides with substitutions at several positions in the putative binding domain of $V_L$ peptide were synthesized to study the effect of these forms of the peptide on cellular physiology. These studies indicate that hydroxyl groups from positions 11 (Tyr), 12 (Ser), 14 (Ser) and 15 (Thr) may be involved in directly interacting with the reovirus type 3 receptor. This is the region of greatest shared identity of amino acids between the $V_L$ peptide and the reo peptide. See Table 1. The variant peptides had amino acid substitutions at positions 11–16, the region of the $V_L$ peptide believed to be the binding domain. To study the effect of these forms of peptide on cellular physiology, lectin induced mitogenesis was utilized to provide a system wherein both receptor perturbation (by the peptides) and aggregation (by the lectin) can be induced.

Peptide Inhibition of Lymphocyte Proliferation

Reovirus type 3 and anti-reovirus type 3 receptor antibodies have both been demonstrated to inhibit concanavalin A (con A) induced lymphocyte proliferation (Nepom, J. T. et al., Immunol. Res. 1:255 (1982), Sharpe, A. H. and B. N. Fileds, J. Virol. 38:389 (1983), Fontana, A. and H. L. Weiner, J. Immunol. 125:2660 (1980)). The effects of these peptides on lymphocyte proliferation both in the presence and in the absence of con A have been investigated as follows.

C3H female mouse spleenocytes were prepared as a single cell suspension, and cultured with peptides at the concentrations noted in absence (A) or in the presence (B) of concanavalin A (con A) at 2.5 μg/μl. 72 hours later, tritiated thymidine was added, the cells were harvested 18 hours later and CPM incorporated determined. Per cent inhibition was calculated as for FIG. 4. The peptides utilized are those described for FIG. 4. In the absence of con A, $V_L$SH peptide markedly inhibited spontaneous lymphocyte proliferation, while $V_L$ peptide had no significant effect (see FIG. 7A). How ever, in the presence of con A, $V_L$SH peptide and $V_L$ peptide had similar effects in inhibiting lymphocyte proliferation (see FIG. 7B).

As shown in FIGS. 8A and 8B, when variant peptides were utilized lacking hydroxyl groups from positions 12 and 15 ($V_L$A12 and $V_L$A15 respectively), the inhibition of con A induced lymphocyte proliferation was attenuated (FIG. 8A). Lymphocyte proliferation was determined as described above for FIGS. 7A and 7B. The peptides utilized were:

$V_L$: Lys-Pro-Gly-Lys-Thr-Asn-Lys-Leu-Leu-Ile-Tyr-Ser-Gly-Ser-Thr-Leu-Gln, $V_L$F11: Lys-Pro-Gly-Lys-Thr-Asn-Lys-Leu-Leu-Ile-Phe-Ser-Gly-Ser-Thr-Leu-Gln, $V_L$A12: Lys-Pro-Gly-Lys-Thr-Asn-Lys-Leu-Leu-Ile-Tyr-Ala-Gly-Ser-Thr-Leu-Gln, $V_L$A13: Lys-Pro-Gly-Lys-Thr-Asn-Lys-Leu-Leu-Ile-Tyr-Ser-Ala-Ser-Thr-Leu-Gln, and $V_L$A15: Lys-Pro-Gly-Lys-Thr-Asn-Lys-Leu-Leu-Ile-Tyr-Ser-Gly-Ser-Ala-Leu-Gln This indicates that these amino acid residues are involved in interactions critical to receptor perturbation, leading to inhibition of proliferation. The hydroxyl groups of positions 11 (Tyr) and 14 (Ser) appeared to have less of an effect on this cellular activity (FIG. 8B).

A peptide with a (Gly-Ala substitution at position 13 in the putative binding domain of $V_L$ peptide ($V_L$A13). Also utilized in contrast to the other substitutions described, $V_L$A13 had an increased effect on the inhibition of Con A induced lymphocyte proliferation at some of the concentrations sed (FIG. 8B). This $V_L$A13 peptide also has increased binding to monoclonal antibody 9BG5, which may mimic the reovirus type 3 receptor on these cells. These studies indicate that modification of the $V_L$ peptide can identify specific residues required for receptor perturbation, and lead to the development of variant peptides with both increased and decreased biologic activity.

Competitive Binding of 9BG5 to 87.92.6 In The Presence Of Peptides

Polystyrene wells were coated with purified 87.92.6 or control IgM, K antibody H022.1 by incubation of purified antibody (purified on a goat anti-mouse IgM column), diluted in 0.1% $NaHCO_3$ pH 9.5 to 1 μg/ml with 50 μl/well, overnight at 4° C. The wells were washed, blocked with 2% BSA in PBS with 0.1% $NaN_3$, washed again and a mixture of radioiodinated 9BG5 and peptides (at the concentrations noted in FIG. 9) were added for one hour at 37° C. The wells were washed and counted. In all cases, specific CPM bound was determined by subtracting CPM bound to blank wells coated with BSA from CPM bound for 87.92.6 coated wells. As shown in FIG. 9, binding of $^{125}$I-9BG5 to wells coated with irrelevant mouse IgM, K antibody H022.1 was similar to binding to blank wells. Per cent inhibition was determined by subtracting specific CPM bound in the presence of inhibitor from specific CPM bound in the absence of inhibitor, dividing this by CPM bound in the absence of inhibitor, and multiplying the result by 100. The ±SEM of values from two experiments is shown in FIG. 9. $V_L$ Peptide Inhibits Binding Of Reovirus Type 3 Particles to 9BG5.

The wells of microtiter plates were coated with neutralizing anti-reovirus type 3 monoclonal antibody 9BG5 or irrelevant class matched monoclonal A11 by adsorption to staphylococcal protein A (SPA). SPA (sigma Chemical Co., St. Louis, Mo.) was diluted to 5 µg/ml in 0.1 M NaHCO$_3$ pH 9.6 and 50 µl/well dispensed into 96 well polystyrene plates. Following overnight incubation at 4° C., the. wells were decanted, washed three times in PBS, and blocked with 2% BSA in PBS with 0.1% NaN$_3$ for one hour at 37° C. The wells were decanted, washed three times in PBS and monoclonal antibody 9BG5 diluted to 10 µg/ml in 1% BSA in PBS with 0.1% NaN$_3$ was added (50 µl/well) for 1–3 hours at 37° C. Prior studies indicated that these amounts of SPA and monoclonal murine IgG2a antibodies gave maximal adsorption of antibody on the wells. The wells were decanted and washed three times in PBS. Competitors were added at the concentrations noted (100 µl/well) diluted in 0.5% BSA in 5 mM phosphate buffer with 0.45% NaCl and preincubated for 45–60 minutes at 23° C. Control experiments indicated that these peptides had no effect on monoclonal antibody binding to the wells. Following preincubation with inhibitors, radio-iodinated reovirus type 3 particles diluted in 1% BSA in PBS with 0.1% NaN$_3$ were added (5–10×10$^5$ CPM per well), and the incubation continued for 45 minutes. Wells were decanted, washed 8–10 times with PBS and the CPM bound determined. $V_L$ peptide inhibits binding of reovirus type 3 particles to 9BG5. As shown in FIGS. 10A–C, 6,700 CPM were bound to 9BG5 coated wells and 500 CPM were bound to control (A11) coated wells in the absence of inhibitors. The mean ± standard deviation of binding inhibition (Determined as noted for FIG. 9) of replicate wells is shown. Control peptide B was used in this study. The competitor peptides in FIGS. 15A and 15B are those described herein. Competitor peptide $V_L$A6 is identical to $V_L$ except that alanine is substituted for asparagine at position 6. The competitor peptides inhibited binding of reovirus type 3 particles to 9BG5.

$V_L$ Peptide Inhibits Binding of Reovirus Type 3 and variant K to L Cells

L cells were suspended at 10$^6$ ml in 1% BSA in PBS with 0.1% NaN$_3$, and 50 µl (5×10$^4$) cells) added to each well of a 96-well microtiter plate, and preincubated with inhibitors at the concentrations noted for 45–60 minutes at 23° C. Equivalent input CPM of radioiodinated reovirus type 3, type or variant K particles were added in 50 µl (700,000 to 1,250,000 CPM/well) and incubated for 45 minutes. The cells were washed three times in 1% BSA in PBS with 0.1% NaN$_3$ and specific CPM bound determined, as noted in FIG. 9. As shown in FIGS. 11A and 11B, $V_L$ peptide inhibits binding of reovirus type 3 and variant K to L cells. The mean ± S.D. percent inhibition of binding from replicate wells is shown versus the final concentration of competitor. As shown in FIGS. 11C and 11D, $V_L$ variant peptides also inhibit binding of reovirus type 3 to murine L cells.

Immunization with Peptides Induces Reovirus-Binding Antibodies

Having established that the $V_L$ and reo peptides contain the epitope involved in the interaction between type 3 reovirus and its specific cellular receptor, it was decided to test if immunization with these peptides would induce antibodies capable of interacting with reovirus type 3 and blocking infection. Groups of Balb/c mice were immunized with these synthetic peptides as noted in the experimental procedures section. Groups of 4 mice received either control peptide in adjuvant, $V_L$ peptide coupled to chicken serum albumin ($V_L$-CSA) in adjuvant, $V_H$ and $V_L$ peptide coupled to CSA ($V_H$+$V_L$-CSA) in adjuvant, reo peptide in adjuvant or reo peptide without adjuvant. As a positive control, an additional group of mice was injected with reovirus type 3. As indicated below, pre-immune serum from these mice disclosed no reovirus neutralizing antibodies indicating no prior exposure to virus.

Radioimmunoassay indicated a strong response to the immunizing antigen in all cases (data not shown). Binding of immune serum (day 60) to reovirus type 1 and type 3 is shown in FIGS. 12A–C. Specific binding was determined by subtracted CPM bound on a blank plate from CPM bound on a virus coated plate. As a further control, specific binding of normal mouse serum to virus coated plates was also subtracted. To simplify interpretation, specific binding is shown for four groups of animals: those immunized with 1) the control peptide, 2) $V_L$-CSA, 3) $V_H$+$V_L$-CSA (all with adjuvant), and 4) reo peptide without adjuvant. Mice immunized with reo peptide plus adjuvant made a response similar to those immunized with $V_L$-CSA, $V_H$+$V_L$-CSA plus adjuvant. Mice immunized with type 3 reovirus made a strong response to type 3 virus (specific CPM at a 10$^{-3}$ dilution of serum of 10,428±807) with significant cross-reactivity with type 1 virus (specific CPM at a 10$^{-3}$ dilution of 6,976±915). As shown in FIGS. 12A–C, serum from mice immunized with control peptide bound poorly to type 1 or type 3 virus coated plates at any of the serum dilutions used. In contrast, significant binding of immune serum to type 1 and type 3 virus coated plates is demonstrated from mice immunized with $V_L$-CSA, $V_H$+$V_L$-CSA or reo peptide. As was expected, binding to type 3 virus was significantly higher than binding to type 1 virus, although some cross-reactivity is seen. The binding of type 1 virus was likely to have been due to some areas of primary sequence similarity between the peptides used here and the type 1 sigma 1a protein (Manemitsu, S. M. et al., Biochem. Biophys. Res. Commun., 140:501–510, 1986).

These results indicate that priming mice with peptides modeled from the putative neutralizing epitope of type 3 reovirus or the corresponding epitope from the anti-receptor monoclonal antibody induces reovirus binding antibodies.

Neutralization of Viral Infectivity by Immune Serum from Peptide Immunized Mice

Serum from peptide immune animals was assayed at three time points to evaluate its effects on viral infectivity of L-cells. Two assays were used to detect neutralization of infectivity. One was a direct cytotoxicity assay measuring the effect of serum on viral lysis of L-cells grown adherent to the wells of 96-well microtiter plates by vital staining, and the other was by measuring inhibition of plaque formation by serum, with virus and L-cells in soft agar. Results from the direct cytotoxicity assay are shown in FIGS. 13A and 13D. Pre-immune serum from all of the animals used was assayed and no significant effect on type 1 or type 3 viral lysis of L-cells was demonstrated. As a positive control, neutralization of L-cell lysis by reovirus was demonstrated by serum from mice immunized with reovirus type 3. This serum produced potent inhibition of lysis by both type 3 and type 1 virus, although a preferential effect on type 3 viral lysis was noted, with neutralization titers of 1:512 for type 3 virus on days 20 and 60, and titers of 1:342 and 1:256 for type 1 virus on days 20 and 50 respectively. Serum from control peptide immunized animals had no effect on L-cell lysis by reovirus type 1 or type 3. Serum from mice immunized with $V_L$-CSA, $V_H$+$V_L$-CSA or reo peptide with or without adjuvant specifically neutralized L-cell lysis by reovirus type 3 but not type 1 (FIG. 13a versus 13b). As results were similar for serum from animals immunized with reo peptide in the presence or absence of adjuvant, results only from the latter group is shown. This effect was also seen when serum from these mice was assayed for inhibition of plaque formation. In FIGS. 14A and 14B, the reciprocal serum titer producing 50% of greater plaque inhibition is shown for type 1 and type 3 virus from the groups immunized with $V_L$-CSA, $V_H$+$V_L$-CSA or reo peptide without adjuvant. Again, specific inhibition of plaque formation by type 3 but not type 1 virus is seen. Since peptide-immune serum specifically inhibits type 3 but not type 1 viral infectivity, these peptides define the neutralizing epitope present on reovirus type 3.

Elicitation of Delayed-Tyne Hypersensitivity (DTH) to Reovirus Type by Immunization with Peptides Prior studies have demonstrated that the specificity of DTH responses to reovirus infection involved the sigma 1 polypeptide (Weiss, H. L. et al., J. Immunol. 125:278–282, 1980. It was therefore determined if immunization of mice with these peptides would elicit DTH responses to intact reovirus. As shown in FIGS. 15A and 15B, significant DTH responses to reovirus type 3 were induced by immunization with $V_L$ peptide. This response was type specific as these animals did not demonstrate significant DTH responses to reovirus type 1. Use of reassortant viruses maps the response to the sigma 1 protein. In addition, priming animals with type 3 virus results in significant DTH to the $V_L$ peptide. A type specific proliferative response to reovirus type 3 in spleen cells from mice immunized with reo peptide was also demonstrated. These data indicate that $V_L$ and reo peptide define an important epitope involved in T cell-mediated immunity to reovirus type 3.

DISCUSSION

It has thus been demonstrated that synthetic peptides defined by areas of corresponding sequences between the reovirus type 3 sigma 1 polypeptide and a monoclonal anti-receptor antibody 87.92.6 define the epitope on the virus and on the antibody involved in interacting with neutralizing antibody 9BG5, elicit neutralizing antibodies and induce T-cell mediated immunity. In addition it has been shown that one of these peptides, $V_L$, competes with binding of 87.92.6 to the reovirus type 3 receptor on R1.1 cells. Since 87.92.6 competes with reovirus type 3 binding to R1.1 cells (Kauffman, R. S., et al. (1983) supra), it is hypothesized that this epitope in the virus is involved in directly interacting with the type 3 reovirus receptor. This is confirmed by the ability of $V_L$ peptide to inhibit binding of reovirus type 3 to cells. Binding of reovirus type 1 (which utilizes a distinct receptor) is not inhibited, indicating a specific interaction with the reovirus type 3 receptor.

Since this epitope encompasses amino acids 317–332 of the sigma 1 polypeptide, this finding would seem at odds with other reports which have implicated amino acid 419 of the hemagglutinin in viral resistance to neutralizing antibodies (Bassel-Duby, R. et al., J. Virol. 60:64–67, 1986), and in tissue tropism of the virus (Kaye, K. M. et al., J. Virol. 59:90–97, 1986). In those studies, viruses were selected for by growth in the presence of neutralizing antibodies (Spriggs, D. R., and Fields, B. N., Nature (London), 297:68–70, 1982), and those resistant to neutralization by the antibodies had their amino acid sequence determined (Bassel-Duby, R., et al, 1986, supra).

Several possibilities might account for the disparity in these results. It is possible that the mutations involving the amino acids 419 induce an allosteric effect on the conformation of amino acids 317–332 which allows interaction with the viral receptor in the presence of the neutralizing antibodies. In this scenario, amino acids 317–332 would be directly involved in binding to the viral receptor and to neutralizing antibody. The mutation at amino acid 419 would induce an allosteric alteration in the confirmation of this region that would allow binding to the viral receptor in the presence of neutralizing antibody. Another possibility is that both regions are involved in binding the viral receptor. In this case both regions would be in close proximity in the tertiary structure of the sigma 1 polypeptide. This is possible as both are predicted to be in the "globular head" region of the hemagglutinin by computer modeling (Bassel-Duby, R., et al, 1985, supra). The mutation of 419 would strengthen the interaction of this area of the hemagglutinin with the receptor, thereby overcoming the blockage of receptor binding by the neutralizing antibodies binding to residues 317–332. While other possibilities exist, clarification of these issues awaits more detailed knowledge of the tertiary structure of the sigma 1 protein.

These studies have direct implications for vaccine development. It would be greatly desirable to be able to delineate the neutralizing epitopes present on microorganisms to aid in development of synthetic vaccines that would effectively protect individuals from infection, without the risks involved in the use of whole organisms. This would be particularly useful in situations where there is marked antigenic heterogeneity in the structure of a pathogen, but the binding site for specific cellular receptors is conserved. A variety of strategies can be and have been employed to determine sites involved in receptor-pathogen interactions including site-directed mutagenesis and immunization of animals with sequential peptides derived from the sequences of pathogen products (Elder, J. H., et al, 1987, supra). Site directed mutagenesis, while yielding specific information about sequence variations that lead to differences in biological effects, suffers from the disadvantage that allosteric effects resulting from the sequence differences could account for the effects induced. In this situation, sequence variation in a region of a gene product may alter the biologic properties of a distant site and yield misleading information. Analysis of the effects of antibodies elicited by immunization with sequential peptides derived from pathogen products, while a definitive approach yielding specific information, is time-consuming and may require analysis of a large number of peptides before a neutralizing immune response is detected.

The above experiments thus demonstrate a method for producing a synthetic biologically active peptide comprising a sequence corresponding to a peptide sequence found in corresponding regions of both an antigen and in an anti-idiotypic antibody for that antigen. By demonstrating corresponding sequences in the sigma 1 cell attachment protein of reovirus type 3 and monoclonal anti-receptor antibody 87.92.6 the neutralizing epitope of reovirus type 3 was localized. These studies confirm that the epitope implicated is the one involved in viral binding to the cellular reovirus type 3 receptor and in the elicitation of neutralizing antibodies. Once the shared region has been defined, other biologically active peptides can be prepared by modifying this peptide sequence. These modifications are directed to the region believed to be involved in binding of the antigen to the receptor. Gly(13) and hydroxyl groups from positions 11(Tyr), 12(Ser), 14(Ser) and 15(Thr) are believed to be involved in directly interacting with the reovirus type 3 receptor. Peptide dimers comprising the shared peptide sequence also have biological activity and can be shown to have greater affinity than monomers.

As the studies herein indicate, modification of the $V_L$ peptide can lead to development of variant peptides with both increased and decreased biological activity. Peptide $V_L A12$ has reduced binding to neutralizing monoclonal antibody, reduced binding to the reovirus type 3 receptor and reduced biologic activity. Peptide $V_L A15$ has increased binding to neutralizing monoclonal antibody, decreased binding to the reovirus type 3 receptor and decreased biological activity. Variant peptides such as $V_L A12$, if used as immunogens, might prevent an effective immune response. However, this might be clinically useful in some instances. $V_L$ peptide itself, if used as an immunogen, might elicit an effective immune response, but direct effects of the $V_L$ peptide on the retrovirus type 3 receptor might be deleterious to the host. In this case, a variant peptide such as $V_L A15$, which binds to neutralizing antibodies, but has reduced biologic activity, might be ideal as an immunogen as it would elicit neutralizing antibodies but would not be expected to have significant direct effects on the retrovirus type 3 receptor and would not be expected to be deleterious to the host. The present approach of defining a shared peptide region of both an antigen and an anti-idiotypic antibody (anti-receptor antibody) for that antigen and subsequently modifying this peptide to produce peptides having more or less biological activity is believed to be generally applicable to other receptor-ligand interactions.

The present approach further demonstrates a method of immunizing a host mammal against an infectious organism having a site which binds specifically to a receptor site on a host cell. This method allowed for the relatively rapid determination of the neutralizing epitope on reovirus type 3 and is believed to be generally applicable to other pathogens for which neutralizing immune responses can be demonstrated.

In the present instance, the reovirus type 3 is known to selectively bind to a structure which is antigenically and structurally similar to the mammalian beta-adrenergic receptor. If attachment of a pathogen to specific cellular receptors is important in the pathogenesis of infection by that pathogen, the approach outlined here should result in the ability to determine the oligopeptide epitope involved in the pathogen-receptor interaction. This should also be applicable to other receptor-ligand interactions in a more general sense, and in the case of polypeptide ligands, should allow the determination of the binding epitopes involved. It is believed that this strategy will lead to the development of biologically active compounds that will interact with specific receptors in predictable ways. Accordingly, a method is disclosed which is useful for synthesizing biologically active compounds using pathogen gene products, such as the reovirus 3, which is known to bind to a physiologic receptor of mammalian cells. Where, as with the mammalian reovirus type 3 receptor, the result of such selective binding is to affect the growth or other metabolic function of the subject cell, the subject method may be used for altering the growth of the mammalian cell by administering the synthetic peptide containing the subject shared peptide sequence or biologically active modification thereof for that purpose.

The strategy of utilizing shared primary structure and molecular mimicry to define interacting oligopeptide epitopes thus should have a wide range of applications in the biological sciences to both define areas of specific interaction between molecules, and to aid in the development of compounds with predictable biologic activity.

Those of ordinary skill in this art recognize that various modifications can be made in the compounds of the invention without departing from the scope hereof. For example, peptides of the same class (i.e., conservative substitution as described by Chu et al, "Conformational Parameters For Amino Acids in Helical, Beta Sheet, and Random Coil Regions Calculated from Proteins", Biochemistry, 13(2):211, 1974, which is incorporated herein by reference) may be substituted in the sequence shared between the antibody and antigen, provided the activity of the resulting peptide is not adversely affected. Similarly, it is contemplated that molecular modeling techniques will permit compounds of quite different primary and secondary structures to be substituted for the peptides of this invention, provided equivalent tertiary structures, as determined using the methods of this invention are employed. Additionally, other antibodies, such as other anti-receptor antibodies to the reovirus type 3 receptor or anti-idiotypic antibodies to neutralizing antibodies may also contact the receptor using CDR regions. Peptides derived from these regions having biologic activity similar to that described herein for $V_L$ peptide are also within the scope of the invention.

Example 2

The present approach also provides an alternative route for the development and production of biologically active peptides. As shown in FIG. 16, antibodies 15 specific for a receptor 11 of the antigen (or ligand) 5 also mimic the antigen 5 in the same way as an anti-idiotype antibody 9 of the antigen mimics the antigen 5.

In pathway I, an antibody 7 contains an epitope designated generally 21 complementary to the neutralizing epitope designated generally 19 of antigen 5. This antibody 7 is then used to produce other antibodies, or anti-idiotype antibodies 9. These anti-idiotype antibodies 9 will have a region designated generally 23 mimicking the neutralizing epitope 19 of the antigen 5. In pathway II, the receptor 11 on cell surface 13 contains an epitope designated generally complementary to the neutralizing epitope 19 of the antigen 5; the antibody specific for the receptor 15 will thus contain a region designated generally 27 mimicking the neutralizing epitope 19 of the antigen 5. The anti-receptor antibody 15 is the equivalent of anti-idiotype antibody 9, since both contain regions (23 and 27) mimicking the neutralizing epitope 19 of the antigen 5. Anti-receptor antibodies 15 can be used as an alternative, or in addition to, anti-idiotype antibodies 9 in the methods described herein to develop and produce biologically active peptides 17 with properties of the antigen or ligand.

Because antigens such as viruses generally contain multiple antigenic epitopes, it may be necessary to screen the antibodies produced in response to the inoculation with the ligand, receptor or anti-ligand antibody to select antibodies having specificity for the neutralizing epitope of the antigen. Screening can be done by competitive assays that determine the antibody's ability to inhibit binding of the antigen to the receptor of the cell, those antibodies having a greater ability to inhibit binding of the antigen containing or mimicking the neutralizing epitope. Other screening methods include those as described herein in which a biological function, such as inhibition of DNA synthesis, is triggered. Suitable screening methods include those described herein, and in Burstin, S. J., et al., Hemagglutinin Virology 117:146–155. It will be obvious to those skilled in the art that various changes to reagents may need to be made in the competitive assays when different antigen and receptor pairs are used.

As demonstrated herein, neutralizing antibody 9BG5, having a specificity for the antigen HA3 on the reo virus, was used to make anti-idiotype antibodies having anti-receptor activity. These anti-idiotype antibodies also bind to the reovirus type 3 receptor. The antibodies were screened to identify antibodies that competed or inhibited binding of the neutralizing antibody with the receptor which would indicate they contained epitopes that mimic HA3, the antigen. The variable region of one antibody having this activity was compared with the sequence of the antigen HA3 to determine corresponding regions that define the interaction site of HA3 and the receptor.

Instead of using an anti-receptor antibody that was produced as an anti-idiotype antibody, the receptor itself is also suitable for producing antibodies that have epitopes mimicking the antigen. To produce antibodies by this route, receptor bearing cells are used as an immunogen, as for example in Drebin, et al., Nature (1984) 321:545–547 and Drebin, et al., Cell (1985) 41:695–706. Alternatively, purified receptor can be used, as for example in Williams, et al., 1989 J. Neurochem 53:362–369 and Meyers et al., 1992 Receptor 2:1–16, both of which are incorporated herein by reference. These two immunogens can be used to make antibodies, usually monoclonal antibodies, by conventional techniques. An animal such as a mouse is first injected with the receptor, its spleen cells are removed and fused with myeloma cells to form hybridoma cells, the latter are cloned in a serum-containing medium and the monoclonal antibodies are separated from the medium. The antibodies are then screened by neutralization assay, as described above, to select those antibodies which specifically bind to the receptor site at the neutralizing epitope. This can be coupled with a screen that examines the biological effects of receptor binding, for example the inhibition of DNA synthesis assay described herein. In the example, both the reovirus and the antibody cause some effect.

The strategy of utilizing shared primary structure and molecular mimicry to define interacting oligopeptide epitopes thus should have a wide range of applications in the biological sciences to both define areas of specific interaction between molecules, and to aid in the development of compounds with predictable biologic activity.

Those of ordinary skill in this art recognize that various modifications can be made in the peptides and compounds of the invention without departing from the scope hereof. For example, peptides of the same class (i.e., conservative substitution as described by Chu et al, Biochemistry, 13(2):211, 1974, which is incorporated herein by reference) may be substituted in the sequence shared between the antibody and antigen, provided the activity of the resulting peptide is not adversely affected. Similarly, it is contemplated that molecular modeling techniques will permit compounds of quite different primary and secondary structures to be substituted for the peptides of this invention, provided equivalent tertiary structures, as determined using the methods of this invention are employed. Additionally, other antibodies, such as other anti-receptor antibodies to the reovirus type 3 receptor or anti-idiotypic antibodies to neutralizing antibodies may also contact the receptor using CDR regions. Peptides derived from these regions having biologic activity similar to that described herein for $V_L$ peptide are also within the scope of the invention.

Example 3: Design of Immunogenic Human Immunodeficiency Virus Peptide

HIV, the AIDS virus, enters its target cell in a series of steps. The first event in this sequence is the attachment of the viral envelope gp120 protein to CD4 on the surface of the target cell. In one embodiment of the invention, gp120 is the protein of interest, that is, the pathogen antigen. Computer graphics and comparative molecular modelling may be used to study the potential conformational properties of the CD4 binding site on gp120.

In the comparative modelling approach, the structure of an unknown protein is deduced from sequence similarities between portions of crystallographically known proteins and the protein fragment to be modelled (Greer et al., 1989, Prog. Clin. Biol. Res. 289:385–397). This approach has been used in the modelling of a wide range of proteins including antibodies and T-cell receptors (De la Paz et al., 1986, EMBO J. 5:415–425; Chothia et al., 1988, EMBO J. 7:3745–3755). It has been hypothesized that retroviruses are evolving towards structurally mimicking epitopes of the immunoglobulin (Ig) superfamily (Oldstone, M. B. A., 1987, Cell 50:819–820) that interact with normal immune structures like CD4.

Structural examination of antigen combining regions of T cell receptors and antibodies indicates that the recognition sites of this particular superfamily class are organized reverse turns or loops. For MHC molecules, molecular recognition areas are highly α helical Bjorkman et al., 1987, Nature 329:506–512). Structural analysis of an anti-receptor antibody that mimics the cell attachment site of reovirus hemagglutinin affirms the possibility of shared β-type conformation as one underlying recognition feature bestowing mimicking properties on antibodies (Williams et al., 1988, Proc. Natl. Acad. Sci. USA, 85:6488–6492). In this context, an anti-CD4 antibody that competes with gp120 for the same CD4 binding site is considered an anti-receptor (anti-idiotypic) antibody that mimics gp120 (McDougal et al., 1986, Immunol. 137:2937–2944).

In the deduction of the possible topography for the CD4 binding site, one may first-examine the Protein Sequence Database (Devereux et al., 1984, Nucl. Acids Res. 12:387–395) using overlapping sequences of the BH10 isolate of HIV from residue 343 through 511. Optimal sequence alignment of the putative cell attachment site of gp120 with members of the Ig superfamily imply a degree of similarity between the site and antibody complementarity determining regions (CDRs) (FIG. 18).

The degree of similarity between the 383–455 region and CDR loops implies only that contact regions between gp120 and CD4 may exhibit β turns or loops, and not that gp120 itself folds like an immunoglobulin. This is evident because the intervening residues between the perceived β loops in gp120 are very different from those in antibodies. The disulfide bridge connecting residues 418 and 445 may preserve the anti-parallel β strands with a reverse turn geometry. In antibody structures, CDR1 and CDR3 of light chains pack against each other and are stabilized by a disulfide bond. If this type of structure exists in gp120, then the β loop comprising residues 419–429 would be packed with the β loop comprising residues 446–454; this packing may be stabilized by the disulfide bridge formed between amino acids 418 and 445. In this model, residues 430–438, representative of a β structure, would still be exposed for contacting CD4.

A molecular model for the region 413–455 (FIG. 19) may be constructed based upon these structural concepts, utilizing a light-chain antibody structure known as REI (Bernstein et al., 1977, Mol. Biol. 112:535–542) as a template for the first and third hypervariable region, in which the cysteines in gp120 at positions 418 and 445 form a disulfide bridge. The cysteines are positionally conserved with respect to each other as in the light chain. The model may be energy optimized using molecular mechanics and dynamics. The model depicted in FIG. 18 indicates that the residues 421–438 define a central turn region of the domain that may be surface exposed for interaction with CD4. Neutralizing antibodies have been shown to be directed toward this site (Sun et al., 1989, J. Virol. 63:3579–3585). The in vitro biological activity of the 421–438 peptide fragment in modulating CD4-depending cellular function and this fragment's ability to induce an anti-HIV response is as described below. This peptide was shown to block virus binding and appears to exhibit cellular regulatory functions such as immunosuppression that parallels gp120.

The putative CD4 binding domain of the human molecule (Lasky et al., 1987, Cell 50:975–985) was modelled after an immunoglobulin variable region. A topography of the purported gp120 binding site for CD4 was obtained based upon a comparative modelling approach utilizing corresponding sequences with the immunoglobulin superfamily (Kieber-Emmons et al., 1989, Biochem. Biophys. Acta 989:281–300). Molecular modeling of the 415–456 region of gp120 suggested that a disulfide bond can be formed by the cysteine residues at positions 418 and 445. The model indicates that the residues 421–438 define a central turn of the domain that is surface-exposed for possible interaction with CD4. Monoclonal antibodies that map to the 421–437 region have recently been shown to have anti-HIV neutralizing ability (Sun et al., 1989, J. Virol. 63: 3579–3585). The 421–438 linear peptide termed B138 (Tables II and III) was synthesized, purified, and assayed for its immunoreactivity with human sera and its ability to induce an anti-HIV response.

The reactivity of linear B138 with sera (1:4 dilution) from healthy HIV-seronegative and seropositive study subjects has been assessed. Low levels of reactivity to B138 were detected using sera from nineteen HIV-seropositive, asymptomatic individuals, with only 2 of 18 (11%) generating levels of anti-B138 antibodies that were significantly different ($p<0.003$) from HIV-seronegative controls. Thirty-three percent (7 of 21) of ARC patients and 10% (2 of 20) of AIDS patients had significant levels of antibodies that bound B 138. Only one HIV-infected individual, an ARC patient, had levels of anti-B138 antibodies that were significantly different from HIV-seronegative individuals at 1:32 dilutions of serum ($p<0.003$). These results demonstrate that HIV-1 does not stimulate the production of antibodies that bind B138 in most infected individuals. Furthermore, in the few individuals that had detectable levels of anti-B138 antibodies, these antibodies occurred at relatively low titers and did not correlate with neutralizing or protective activities.

The immunogenicity of B138 was determined by subcutaneous immunization of mice and rabbits. Mouse antisera to B138 was shown to preferentially bind to $HIV_{HTLVIIIB}$-infected H9 cells as assessed by flow cytometry analysis. Rabbit anti-B138 sera could immunoprecipitate purified recombinant glycosylated gp120 as assessed by radiolabelled immunoprecipitations, albeit weakly.

However, the immunogenicity of B138 increased dramatically when the B138 was made into the cyclic peptide, 1005–45 (Tables II and III) by cysteine bond formation. Molecular dynamic calculations of the linear 421–438 segment and the cyclic 418–445 fragment suggested that the conformational populations available to the 421–438 region under the cyclic constraints were restricted and more similar to our predicted geometry of the gp120 putative CD4 binding epitope. Radiolabelled immunoprecipitations (RIPs) of rabbit anti-sera against the cyclic peptide showed significant specificity towards recombinant glycosylated gp120 (FIG. 20). The reactivity is similar to that of the immunoreactivity of polyclonal human HIV positive sera reactive with gp120. Infectivity assays with rabbit anti-B138 and rabbit anti-1005/45 sera showed that both peptides could elicit neutralizing antibodies.

FIG. 21 shows the results of experiments in which rabbits were immunized with various gp120-derived peptides (see Table II) conjugated to Keyhole limpet hemocyanin (KLH) by glutaraldehyde fixation. Antisera was obtained and tested for binding to recombinant HIV-1 gp120 peptide-coated radioimmunoassay plates (using 1 μg/ml gp120 at 50 μl/well, in 0.1 M $NaHCO_3$ and incubating overnight at 4° C.). The indicator antibody was $^{125}I$-labelled anti-rabbit immunoglobulin antibody. FIG. 21 indicates that the highest levels of bound antibody were associated with antisera produced by animals immunized with 1005–45 cyclic peptide as compared to lower levels of bound antibody associated with antisera produced by animals immunized with linear B138. Higher bound levels of antibody could result from a generally greater immune response and/or the production of antibodies that have a higher affinity for gp120.

The invention is not limited in scope by the embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the scope of the appended claims.

Example 4 As an alternative example, CD4 may be the protein of interest.

Interestingly, the CD4 receptor is only one of a small number of viral receptors that have been cloned (White et al., 1989, Cell 56:725–728). An examination of the DNA sequence and the exon/intron organization of the nucleotides which encode the CD4 glycoprotein strongly suggests that this gene has evolved from a primordial Ig gene (see Littman, D. R., 1987, Annu. Rev. Immunol. 5:561–584 for review). Similarity profiles of the CD4 amino-acid sequence also reflect this relatedness to members of the Ig superfamily (FIG. 22; for reviews of the superfamily see Hood et al., 1985, Cell 40:225–229 and Williams et al., 1988, Annu. Rev. Immunol. 6:381–405). The most striking similarity between the CD4 protein and the Ig superfamily occurs between the first 84 amino acids of the CD4 glycoprotein and the Ig light chain variable domain (FIG. 22). Although other CD4 regions also show similarity, secondary structure predictions generated from this domain of CD4 are also extraordinarily similar to those observed for the Ig light chain variable domains. Membership of the CD4 protein in the superfamily implies that the structure of the Ig-like domains of this protein should exhibit the classical "Ig-fold" (Schiffer et al., 1973, Biochemistry 12:4620–4631; Poljak et al., 1973, Proc. Natl. Acad. Sci. U.S.A. 70:3305–3310; Amzel et al., 1979, Annu. Rev. Biochem. 48:961–997). Therefore the alignment of CD4 with members of the Ig superfamily indicates tertiary structural similarities when residues, identified by X-ray diffraction studies of antibody hypervariable regions, are aligned on the premise that the basic building-block structure and interaction have been conserved (FIG. 23).

The sequence relationship between CD4 and immunoglobulins allows for general conceptions about the structure of CD4 to be formulated and correlated with CD4 epitope mapping studies. Analysis of Ig structure to delineate possible unique epitopes may therefore be used to examine gp120 binding to CD4. Structural analysis of epitope locations on the surfaces of antibodies suggests that there are separate or non-overlapping (epitope) recognition sites that involve both classical CDR and framework regions (Kieber-Emmons et al., 1986, Immunol. Rev. 90:29–48; FIG. 23). Such regions have been referred to as idiotype determining regions (IDR) (Kieber-Emmons et al., 1986, Immunol. Rev. 90:29–48). Each of these epitope (putative recognition) sites may have unique functional properties. By inference, the CD4/Ig superfamily sequence alignment implies that HIV, MHC class II, ancillary proteins such as CD3, and T cell receptors may bind to CD4 in noncompetitive ways.

Example 5 Design of a Cyclic Peptide which binds to the Cellular Reovirus Receptor and can block the interaction between Reovirus and its Target Cells In this embodiment of the invention, the protein of interest is an immunoglobulin molecule, and the method of the invention comprises identifying a region of the molecule which is similar to the CDR of another immunoglobulin, synthesizing peptides which comprise portions of the identified CDR, and then modifying the peptide such that it has biological activity. This example presents a nonlimiting working example of an embodiment in which a cyclic peptide is designed to resemble a CDR of an anti-virus receptor antibody.

MATERIALS AND METHODS

Peptides

All peptides were synthesized by solid phase methods, deprotected and released from the resin utilizing anhydrous HF. Peptides were lyophilized and further purified by high performance liquid chromatography utilizing a TSK 3000 column and lyophilized. Purity was assessed by high performance liquid chromatography utilizing a C-6 column and a 0–70% acetonitrile gradient. All peptides were greater than 90% pure. Peptides (containing internal cysteine residues) were cyclized for experiments by dissolving them at 2 mg/ml in distilled water, and stirring them overnight exposed to the air. The peptides had no free sulfhydrlys following this procedure by Ellman determination.

Reovirus

Purified reovirus type 3 was prepared and radioiodinated using methods set forth in Williams et al., 1988, Proc. Natl. Acad. Sci. USA 85:6488–6492, which is incorporated herein by reference.

Monoclonal Antibodies

Monoclonal antibodies 9BG5, which binds to reovirus type 3 hemagglutinin, and 87.92.6, which mimics the reovirus type 3 hemagglutinin by binding to both 9BG5 as well as the reovirus type 3 receptor, are as described in Williams et al., 1989, Proc. Natl. Acad. Sci. U.S.A. 86:5537–5541, which is incorporated herein by reference.

Determination of Free Sulfhydryls in Peptides (Ellman Determination)

Peptides dissolved in $dH_2O$ at 2 mg/ml were added at 5, 10, or 20 $\mu$l to 10 mM $NaPO_4$ pH 7.0 for a final volume of 1 ml. To this was added 6 $\mu$l of 2,2'-bis azidothiobenzoic acid (ATBS, Sigma Chemical Co., St. Louis, Mo.) in 50 mM $NaPO_4$ pH 8.0. This was allowed to react for greater than 3 minutes and the optical density (OD) at 420 nm was subsequently determined.

Radioimmunoassay (RIA)

RIA plates (Dynatech Laboratories, Alexandria, Va.) were coated with peptides by evaporation of varying amounts of peptides in distilled water overnight at 37° C. The wells were washed with PBS, blocked with 2% bovine serum albumin (BSA) in PBS with 0.1% $NaN_3$, and washed with PBS. Partially purified 9BG5 [$(NH_4)_2SO_4$ precipitate] was added at varying dilutions for greater than 1 hour at 37° C. The wells were washed in PBS and 50,000–100,000 counts per minute of $^{125}$I-labelled goat anti-mouse light chain (anti-k & anti-[Sigma] iodinated by chloramine T) was added per well in 1% BSA in PBS for 1–2 hours at 37° C. The wells were decanted, washed extensively, and CPM bound determined. Specific CPM bound was determined by subtracting the CPM bound to uncoated wells from the CPM bound to peptide coated wells.

Competitive RIA

RIA plates were coated with Staphylococcus protein A (Sigma Chemical Co., St. Louis, Mo.) by incubation of 50 $\mu$l per well of a 5 $\mu$g/ml solution overnight at 4° C. The wells were washed with PBS, blocked with 2% BSA/PBS/0.1%$NaN_3$, and purified 9BG5 or isotype matched control monoclonal (All) adsorbed to the wells by incubation of 50 $\mu$l of a 10 $\mu$g/ml solution (purified antibody) in 1% BSA/PBS/$NaN_3$ for 1–2 hours at 37° C. The wells were washed, and competitors were added at various concentrations in 100 $\mu$l of 0.5% BSA/0.45% NaCl/0/05% phosphate buffer pH 7.2 for 1 hour at 37° C. 125I-labelled reovirus type 3 (5–10×$10^5$ CPM per well) or unlabelled antibody (87.92.6 or isotype matched monoclonal E4.49.2) at a 1:100 dilution of ascites in 1% BSA/PBS/0.1% $NaN_3$) was added for an additional 30–45 minutes at 23° C. For wells incubated with 87.92.6, the wells were washed in PBS, and $^{125}$I-labelled goat anti-mouse Ig added for an additional 60 minutes at 37° C. The wells were washed extensively, and CPM bound determined. For reovirus binding, specific CPM bound was determined by subtracting CPM bound to All coated wells from CPM bound to 9BG5 coated wells. For 87.92.6 binding, specific binding was determined by subtracting CPM bound following incubation with E4.49.2 ascites from CPM bound following 87.92.6 incubation. % inhibition binding was determined by the formulae: [(Specific CPM bound w/o Inhibitor) - (Specific CPM bound with inhibitor)×100] / Specific CPM bound without inhibitor. That is, the amount of specific CPM bound w/o Inhibitor minus the amount of specific CPM bound with inhibitor, the total amount remaining being multiplied by 100, the product of which is divided by specific CPM bound without inhibitor.

Inhibition of Viral Binding to Cells

The cells were centrifuged and washed twice in 1% BSA/PBS/0.1% $NaN_3$. 5×$10^4$ cells or 1.25×$10^6$ R1.1 cells in 50 $\mu$l were distributed in 2% BSA/PBS/$NaN_3$ blocked RIA wells. For peptide studies, 50 $\mu$l of inhibitor was added in $dH_2O$ to the cells. Following a 30 minute incubation, L cells and $^{125}$I-labelled reovirus type 3 were combined for an additional 30 minutes at 37° C. The cells were spun, washed three times in ice cold PBS, and specific CPM bound was determined as noted above. Percent inhibition of binding was calculated by the formulae above.

Flow Cytometry Analysis

The ability of peptides to inhibit antibody binding to cells was determined by preincubation of the cells with varying amounts of inhibitor (in 100 $\mu$l $dH_2O$) for between 30 minutes and 1 hour at 23° C. Cells (either L cells or R1.1 cells) were washed in 1% BSA/PBS/0.1% $NaN_3$, and resuspended at $10^7$/ml. 100 µl of cells were then added in 1% BSA/PBS/0.1% $NaN_3$, and the incubation continued for 20–30 minutes. Antibodies (5 or 10 µl were added for an additional 20 minutes at 23° C. Ice cold 1% BSA/PBS/0.1% $NaN_3$, was added, the cells centrifuged and washed prior to counterstaining with a 1:100 dilution of FITC goat anti-mouse Ig (Fisher Scientific) in 1% BSA/PBS/0.1% $NaN_3$. The cells were washed twice and fluorescence intensity determined. Inhibition of binding was calculated as noted above with mean channel number utilized in place of CPM.

Coupling of Peptides to KLH and Immunization

Peptides were coupled by glutaraldehyde fixation or specific coupling through a heterobifunctional cross-linker (MBS, Pierce Chemical Co.) (Romano et al., 1989, J. Neurochem. 53:362–369). Immunization was as described in Romano et al., supra.

RESULTS AND DISCUSSION

Peptide Cyclization

One measure of the optimal folding conformation of $V_L$ peptide is reflected by the ability of cysteine-containing variates to cyclize. If the cysteine residues are placed in various positions in one or the other side of a predicted reverse turn, the residues placed in the most energetically favorable locations for assuming a reverse turn structure should also cyclize most rapidly. This can be established utilizing several cysteine containing peptides as outlined in Table III.

These peptides were subjected to oxidation by agitating a solution (2 mg.ml in 0.1 M $NaHCO_3$) at 37° C. for varying periods of time exposed to air. The disappearance of free sulfhydryls was quantitated by Ellman determination as above, and % loss of sulfhydryls with time calculated. The results are shown in FIG. 23.

Peptides (Table III) were agitated at 37° C. for varying periods of time and loss of sulfhydryls quantitated. As noted, $V_LC_6C_{16}$ and $V_LC_9C_{16}$ had the most rapid loss of sulfhydryls in this assay, while $V_LC_{10}C_{16}$ peptide forms intramolecular disulfide bridges more slowly than the other two peptides, and implies that the corresponding cyclic conformation of $V_LC_{10}C_{16}$ may be energetically more costly to assume than that of $V_LC_8C_{16}$ or $V_{LC9}C_{16}$.

The oxidation of these peptides did not necessarily imply that cyclic peptide formation was taking place, as intermolecular disulfide bridges also might have been forming. This issue was also examined by examining reduced (2-mercaptoethanol treated) and non-reduced variates of these peptides by size-exclusion chromatography utilizing a Sephadex G-10 superfine column. These studies indicated that both $V_LC_8C_{16}$ and $V_LC9C16$ peptides remained chiefly as monomers following oxidation, while a sizeable proportion of $V_LC_{10}C_{16}$ migrated more rapidly following oxidation. This indicates that the $V_LC_8C_{16}$ is forming intermolecular disulfide bridges, with subsequent formation of higher molecular weight forms. In contrast, $V_LC_8C_{16}$ and $V_LC_9C_{16}$ did not form intermolecular disulfide bridges, indicating that these peptides more readily fold into an appropriate conformation for intramolecular disulfide bond formation.

Binding of 9B.G5 to Peptides

To assess the optimal conformation for binding of the $V_L$ peptide analogs, they were utilized to coat radioimmunoassay (RIA) plates, and 9B.G5 bound by standard RIA procedures. The results are shown in FIG. 24.

As can be seen, binding to $V_LC_9C_{16}$ peptide was higher than binding to the other cyclic $V_L$ peptide analogs. This indicates that $V_LC_9C_{16}$ peptide has enhanced binding to 9B.G5 on solid phase RIA in comparison with the other cyclic peptides. Inhibition of 9B.G5 - 87.92.6 Interaction by Peptides While the solid phase RIA indicates a higher affinity of 9B.GS to $V_LC_9C16$ peptide compared to the other cyclic peptides, it does not address the affinity of this interaction in solution. To investigate the optimal solution conformation for 9B.G5 binding, the peptides were utilized to inhibit 9B.G5 - 87.92.6 interaction in a liquid phase assay. As shown in FIG. 25, the results of this assay indicate the $V_LC9C16$ peptide again demonstrates a higher affinity of interaction compared with the other cyclic peptide variants. When compared with a linear analog of $V_L$ peptide (FIG. 26), $V_LC_9C_{16}$ peptide displays an increased affinity of binding (40 fold higher affinity). This indicates that the increased conformational stability of this cyclic peptide increases its binding affinity for 9B.G4. It is also demonstrated that a peptide derived from the 81.92.6 heavy chain variable region CDR II ($V_H$ peptide) is able to inhibit the 87.92.6 - 9B.G5 interaction. While this peptide inhibits the idiotype- anti-idiotype interaction, it does not significantly interact with the reovirus type 3 receptor (Reo3R). Inhibition of 9B.GS-Reovirus type 3 Interaction by Peptides To confirm that $V_LC_9C_{16}$ peptide represents an optimal conformation for 9B.G5 binding in solution phase it was utilized to inhibit binding of $^{125}$I-labelled reovirus type 3 to 9B.G5 in a similar assay. The results are shown in FIG. 27. As can be seen, $V_LC_9C_{16}$ peptide also exhibited higher affinity than the other cyclic peptides in this assay. When compared with linear $V_L$ peptide and dimeric $V_L$SH peptide (FIG. 28), $V_LC_9C_{16}$ peptide demonstrates higher affinity than linear $V_L$ peptide, and similar affinity on a molar basis as dimeric $V_L$SH peptide.

Inhibition of REO3R-87.92.6 Interaction by Peptides

To assess the affinity of the cyclic peptides for the reovirus type 3 receptor (Reo3R), they were utilized in a series of assays to inhibit binding of 87.92.6 or control antibodies to specific receptors. As shown in FIG. 29, $V_LC_9C_{16}$ peptide inhibited binding of 87.92.6 to murine L cells and R1.1 thymoma cells. In contrast, linear $V_H$ peptide had no effect on 87.92.6 binding, while $V_L$ peptide is a less effective competitor on L cells, and ineffectual on R1.1 cells. The inhibition by $V_LC_9C_{16}$ peptide was specific as binding of isotype matched monoclonal H013.4 to Thy2 molecules was not inhibited by $V_LC_9C_{16}$ peptide (FIG. 30). Thus, $V_LC_9C_{16}$ peptide is a specific Reo3R ligand with enhanced affinity compared with its linear analog.

Inhibition of REO3R-Reovirus type 3 Interaction by Peptides

To further evaluate the interaction of $V_LC_9C_{16}$ peptide with the Reo3R, the peptide was utilized to compete with $^{125}$I-labelled reovirus type 3 for binding to the Reo3R. As indicated in FIG. 31, $V_LC_9C_{16}$ peptide demonstrated higher affinity for the Reo3R than $V_LC_8C_{16}$ peptide or $V_LC_{10}C_{16}$ peptide. When compared with linear $V_L$ peptide (FIG. 30), $V_LC_9C_{16}$ peptide demonstrated 40 fold higher affinity for the Reo3R, and similar affinity to dimeric $V_L$SH peptide.

This confirms that cyclic analogs of $V_L$ peptide demonstrate higher affinity of binding to the Reo3R than the linear peptide analogs. This strategy should be applicable to peptides derived from other antibody variable regions, and defines an overall strategy for determining the optimal conformation for binding of these peptides.

TABLE I

Synthetic Peptides Comprising Corresponding Sequences of
87.92.6 and the Reovirus Type 3 Hemagglutinin

| | | | | | | | | | | | | | | | | | | |
|---|---|---|---|---|---|---|---|---|---|---|---|---|---|---|---|---|---|---|
| $V_H$ | Gln | Gly | Leu | Glu | Trp | Ile | Gly | Arg | Ile | Asp | Pro | Ala | Asn | Gly | | | | |
| Reo | Gln | Ser | Met | --- | Trp | Ile | Gly | Ile | Val | Ser | Tyr | Ser | Gly | Ser | Gly | Leu | Asn | |
| $V_L$ | Lys | Pro | Gly | Lys | Thr | Asn | Lys | Leu | Leu | Ile | Tyr | Ser | Gly | Ser | Thr | Leu | Gln | |
| Control | Lys | Ser | Gly | Asn | Ala | Ser | Thr | Pro | Gln | Gln | Leu | Gln | Asn | Leu | Thr | Leu | Asp | Ile | Arg | Gln | Arg |

TABLE II

| Peptide Number | Sequence |
|---|---|
| 466 | FRPGGGDMRDNWSEL |
| 1005-45 | CRIKQFINMWQEVGKAMYAPPISGQIRC |
| B138 | KQFINMWQEVGKAMYAPP |

TABLE III

Peptides Utilized in These Studies

| Designation | Sequence |
|---|---|
| $V_L$: | Lys Pro Gly Lys Thr Asn Lys Leu Leu Ile Tyr Ser Gly Ser Thr Leu Gln |
| $V_L$SH: | <u>Cys</u> Lys Pro Gly Lys Thr Asn Lys Leu Leu Ile Tyr Ser Gly Ser Thr Leu Gln |
| $V_L C_8 C_{16}$: | Lys Pro Gly Lys Thr Asn Lys <u>Cys</u> Leu Ile Tyr Ser Gly Ser Thr <u>Cys</u> Gln |
| $V_L C_9 C_{16}$: | Lys Pro Gly Lys Thr Asn Lys Leu <u>Cys</u> Ile Tyr Ser Gly Ser Thr <u>Cys</u> Gln |
| $V_L C_{10} C_{16}$: | Lys Pro Gly Lys Thr Asn Lys Leu Leu <u>Cys</u> Tyr Ser Gly Ser Thr <u>Cys</u> Gln |
| B138: | Lys Gln Phe Ile Asn Met Trp Gln Glu Val Gly Lys Ala Met Tyr Ala Pro Pro |
| 1005/45: | Cys Arg Ile Lys Gln Phe Ile Asn Met Trp Gln Glu Val Gly Lys Ala Met Tyr Ala Pro Pro Ile Ser Gly Gln Ile Arg Cys |

What is claimed is:

1. A method of constructing a biologically active peptide comprising the steps of:
   (a) comparing amino acid sequences of complementarity-determining regions of an anti-receptor antibody that mimics or blocks a biologically active protein that binds said receptor with the amino acid sequence of said biologically active protein;
   (b) identifying an amino acid sequence of at least 6 amino acids in a complementarity-determining region of said anti-receptor antibody that corresponds to an amino acid sequence of said biologically active protein; and
   (c) synthesizing a peptide which comprises said amino acid sequence of said anti-receptor antibody that corresponds to the amino acid sequence of said biologically active protein; wherein said peptide binds to said receptor and mimics said biologically active protein or blocks said biologically active protein from binding to said receptor.

2. A method of constructing a biologically active peptide comprising the steps of:
   (a) comparing the amino acid sequences of complementarity-determining regions of an anti-receptor antibody that mimics or blocks an antigen which binds said receptor with the amino acid sequence of said antigen;
   (b) identifying an amino acid sequence of at least 6 amino acids in a complementarity-determining region of said anti-receptor antibody that corresponds to an amino acid sequence of said antigen; and
   (c) synthesizing a peptide which comprises said amino acid sequence of said anti-receptor antibody that corresponds to the amino acid sequence of said antigen; wherein said peptide binds to said receptor and mimics said biologically active protein or blocks said biologically active protein from binding to said receptor.

* * * * *